US011931348B2

(12) United States Patent
Poirier et al.

(10) Patent No.: US 11,931,348 B2
(45) Date of Patent: *Mar. 19, 2024

(54) METHODS OF TREATING ELEVATED PLASMA CHOLESTEROL

(71) Applicant: Montréal Heart Institute, Montréal (CA)

(72) Inventors: Steve Poirier, Montréal (CA); Brent Richard Stranix, Pointe-Claire (CA); Gaétan Mayer, Montréal (CA)

(73) Assignee: Montréal Heart Institute, Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/750,698

(22) Filed: May 23, 2022

(65) Prior Publication Data

US 2023/0088095 A1    Mar. 23, 2023

Related U.S. Application Data

(63) Continuation of application No. 16/759,815, filed as application No. PCT/CA2018/051377 on Oct. 30, 2018, now Pat. No. 11,400,082.

(60) Provisional application No. 62/578,872, filed on Oct. 30, 2017.

(51) Int. Cl.
 *A61K 31/44* (2006.01)
 *A61K 31/40* (2006.01)
 *A61K 31/436* (2006.01)
 *A61P 3/06* (2006.01)

(52) U.S. Cl.
 CPC ............. *A61K 31/44* (2013.01); *A61K 31/40* (2013.01); *A61K 31/436* (2013.01); *A61P 3/06* (2018.01)

(58) Field of Classification Search
 CPC .................................................... A61K 31/44
 USPC ......................................................... 514/302
 See application file for complete search history.

(56) References Cited

U.S. PATENT DOCUMENTS

| 5,288,716 | A | 2/1994 | Speck |
| 6,066,659 | A | 5/2000 | Speck |
| 8,283,366 | B2 | 10/2012 | Stranix et al. |
| 8,742,123 | B2* | 6/2014 | Stranix ............... C07D 213/81 546/323 |
| 11,400,082 | B2 | 8/2022 | Poirier et al. |

FOREIGN PATENT DOCUMENTS

| CA | 2613860 A1 | 1/2007 |
| WO | WO-2008/040651 A1 | 4/2008 |
| WO | WO-2009/146555 A1 | 12/2009 |

OTHER PUBLICATIONS

Bartlett "Exploiting Chemical Diversity for Drug Discovery" Edited by Paul A Bartlett and Michael Entzeroth, the Royal Society of Chemistry, 2006, pp. 113-118.*
"Find ETDs Home » Thesis Resources » Find ETDs" Online: "https://ndltd.org/thesis-resources/find-etds/" Accessed Jan. 31, 2023.*
Irwin "Zinc—A Free Database of Commercially Available Compounds for Virtual Screening" J. Chem. Inf. Model. 2005, 45, 177-182.*
Kim "PubChem in 2021: new data content and improved web interfaces" Nucleic Acids Research, 2021, vol. 49, Database issue Published online Nov. 5, 2020.*
STN Registry/Zregistry (CAS Registrysm) Sep. 2016 2 pages.*
Brattström et al., "Pyridoxine reduces cholesterol and low-density lipoprotein and increases antithrombin III activity in 80-year-old men with low plasma pyridoxal 5-phosphate," Scand J Clin Lab Invest. 50(8):873-7 (1990).
International Search Report and Written Opinion for International Application No. PCT/CA2018/051377, dated Jan. 16, 2019 (8 pages).
Extended European Search Report for European Patent Application No. 18874508.7, dated May 13, 2022 (6 pages).

* cited by examiner

*Primary Examiner* — Nizal S Chandrakumar
(74) *Attorney, Agent, or Firm* — Clark & Elbing LLP

(57) ABSTRACT

The present invention relates to compounds of Formula I, pharmaceutically acceptable salts, solvates or formulations thereof. Compounds of Formula I increase significantly low density lipoprotein receptor and are useful for preventing and treating of elevated cholesterol.

17 Claims, 20 Drawing Sheets

Specification includes a Sequence Listing.

METHODS OF TREATING ELEVATED PLASMA CHOLESTEROL

FIELD OF THE INVENTION

The present invention is directed to pyridoxine derived compounds of Formula I, pharmaceutically acceptable salts or solvates thereof, pharmaceutical formulations including one or more compounds of Formula I, methods synthesizing or manufacturing a compound of Formula 1, and use the compounds as modulators (e.g., enhancers) of low-density lipoprotein receptor (LDLR). Compounds of the present invention are useful for prophylaxis, treatment of elevated plasma cholesterol, delay in the onset, or delay in the progression of atherosclerotic cardiovascular diseases (ASCVD).

BACKGROUND OF THE INVENTION

A disease of the arteries, atherosclerosis, is recognized to be the leading cause of death in Europe, Canada, and the United States. The sequence of events leading to atherosclerosis and occlusive heart disease pathology is well known. The earliest stage in this sequence is the formation of lesions, "fatty streaks," in the major blood vessels. It is postulated that most of the cholesterol found within the fatty streaks, in turn, gives rise to development of the "fibrous plaque," cells plus matrix protein form a fibrous cap that covers a deeper deposit of cell debris and extracellular lipids. Epidemiological investigation has firmly established hyperlipidemia (i.e., high plasma lipids) as a primary risk factor in causing cardiovascular disease (CVD) due to atherosclerosis. The most important factor leading to atherogenesis is longstanding hypercholesterolemia, high circulating levels of low-density lipoprotein (LDL) that result in cholesterol depositions in arterial vessels.

Leaders of the medical profession have placed renewed emphasis recently on lowering plasma cholesterol levels, and LDL-cholesterol, as an essential step in prevention of ASCVD. Western populations are at a high risk. Additional risk factors include: being of the male sex, postmenopausal women, hypertension, glucose intolerance, insulin resistance, tobacco use, physical inactivity, stress, and left ventricular hypertrophy. Successful treatment of hyperlipidemia in the general population, and in diabetic subjects, is of exceptional medical importance.

Plasma LDL particles, which carry the majority of total circulating cholesterol, are cleared by binding to hepatic LDL receptors (LDLR), being endocytosed, and being catabolized.

SUMMARY OF THE INVENTION

The compounds of the present invention are useful for enhancing low-density lipoprotein receptor (LDLR) activity and, in particular, for inducing low-density lipoprotein receptor production, and for treating elevated plasma cholesterol and related conditions. The present invention relates to a series of low-density lipoprotein receptor inducers derived from pyridoxine and pharmaceutically acceptable derivatives thereof (e.g., salts and solvates) described in U.S. Pat. No. 8,742,123 B2, which is hereby incorporated by reference.

The compounds of the present invention are useful for enhancing LDLR activity and, in particular, for inducing LDLR production, and for treating elevated plasma cholesterol and related conditions. The present invention relates to a series of LDLR inducers derived from pyridoxine and pharmaceutically acceptable derivatives thereof (e.g., salts and solvates) described in U.S. Pat. No. 8,742,123, which is hereby incorporated by reference.

Accordingly, in the first aspect, the invention features a method of lowering low-density lipoprotein (LDL)-cholesterol level in the bloodstream of a subject. This method includes administering to the subject a LDL-lowering amount of a compound having the formula:

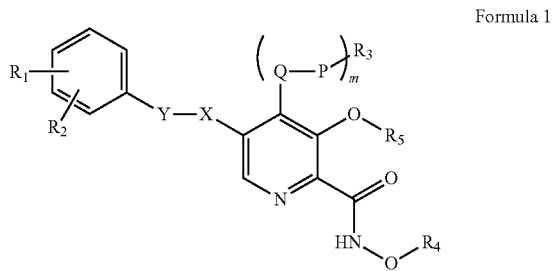

Formula 1 where Y—X is —C($R_7$)($R_{7a}$)N(R')C(O)—; —C($R_7$)($R_{7a}$)OC(O)—; —C($R_7$)($R_{7a}$)N(R')C($R_6$)($R_{6a}$)—; —C($R_7$)($R_{7a}$)S(O)$_2$C($R_6$)($R_{6a}$)—; —S(O)$_2$C($R_6$)($R_{6a}$)—; —C($R_7$)($R_{7a}$)C($R_6$)($R_{6a}$)—; —O—C($R_6$)($R_{6a}$)—; —N(R')C($R_6$)($R_{6a}$)—; or —C($R_7$)($R_{7a}$)OC($R_6$)($R_{6a}$)—, where each of $R_6$, $R_{6a}$, $R_7$, and $R_{7a}$, is, independently, selected from H, $C_{1-6}$ alkyl, $C_{1-6}$ fluoroalkyl, benzyl, phenyl, and heterocycle, R' is selected from H, $C_{1-6}$ alkyl, benzyl, S(O)$_2$R'', and C(O)R'', and R'' is selected from $C_{1-6}$ alkyl, $C_{1-6}$ fluoroalkyl, benzyl, phenyl, and heterocycle; when Q is H, P and $R_3$ are absent; when Q is CH$_3$, P and $R_3$ are absent; Q is CH$_2$, or C(O); when P is H, $R_3$ is absent; P is —O—, —N($R_8$)($R_{8a}$), or is absent, where the $R_8$ and $R_{8a}$ are selected independently from H, $C_{1-6}$ alkyl, $C_{1-6}$ fluoroalkyl, benzyl, phenyl, and heterocycle; $R_1$ is absent, $C_{1-6}$ alkyl, $C_{1-6}$ branched alkyl, $C_{1-6}$ alkene, halogen (F, Cl, Br, I), OH, —O—($C_{1-6}$ alkyl), —O—($C_{1-6}$ branched alkyl), —C(O)($R_9$), —C(O)O($R_9$), —C(O)N($R_9$)($R_{9a}$), or —S(O)$_2$N($R_9$)($R_{9a}$), where $R_9$ and $R_{9a}$ are selected independently from H, $C_{1-6}$ alkyl, $C_{1-6}$ fluoroalkyl, benzyl, phenyl, and heterocycle; $R_2$ is absent, $C_{1-6}$ alkyl, $C_{1-6}$ branched alkyl, $C_{1-6}$ alkene, halogen (F, Cl, Br, I), OH, —O—($C_{1-6}$ alkyl), —O—($C_{1-6}$ branched alkyl), —C(O)($R_{10}$), —C(O)O($R_{10}$), or —C(O)N($R_{10}$)($R_{10a}$), where $R_{10}$ and $R_{10a}$ are selected independently from H, $C_{1-6}$ alkyl, $C_{1-6}$ fluoroalkyl, benzyl, phenyl, and heterocycle; or $R_1$ and $R_2$ are ortho substituents that together form a carbocyclic or heterocyclic ring system; $R_3$ is H, $C_{1-6}$ alkyl, $C_{1-6}$ fluoroalkyl, benzyl, phenyl, heterocycle, or is absent; $R_5$ is H, $C_{1-6}$ alkyl, $C_{1-6}$ fluoroalkyl, benzyl, phenyl, or heterocycle; or $R_3$ and $R_5$ combine to form a heterocyclic ring system; $R_4$ is H, $C_{1-6}$ alkyl, $C_{1-6}$ fluoroalkyl, benzyl, phenyl, or heterocycle, and m is 0 or 1; or a pharmaceutically acceptable salt or solvate thereof.

In some embodiments of the first aspect of the invention, Q is CH$_2$, P is —O—, $R_3$ is H, Y—X is —CH$_2$NHCH$_2$— or —CH$_2$NHC(O)—, $R_1$ is selected from a halogen, —OH or —OCH$_3$, $R_2$ is absent or selected from —OH and a halogen, $R_4$ is H or benzyl, and $R_5$ is H or benzyl, or a pharmaceutically acceptable salt or solvate thereof.

In other embodiments of the first aspect of the invention, Q is CH$_2$, P is —O—, $R_3$ is CH$_3$, Y—X is —CH$_2$OCH$_2$—, $R_1$ is selected from a halogen, —OH or —OCH$_3$, $R_2$ is absent or selected from —OH and a halogen, $R_4$ is H or benzyl, and $R_5$ is H or benzyl or a pharmaceutically acceptable salt or solvate thereof.

In an embodiment of the first aspect of the invention, the compound is 5-[(4-fluoro-phenylamino)-methyl]-3-hydroxy-4-hydroxymethyl-pyridine-2-carboxylic acid hydroxyamide. In one embodiment, 5-[(4-fluoro-phenylamino)-methyl]-3-hydroxy-4-hydroxymethyl-pyridine-2-carboxylic acid hydroxyamide is administered in combination with a statin (e.g., atorvastatin).

In another embodiment of the first aspect of the invention, the compound is 5-(4-fluoro-phenoxymethyl)-3-hydroxy-4-hydroxymethyl-pyridine-2-carboxylic acid hydroxyamide. In one embodiment, 5-(4-fluoro-phenoxymethyl)-3-hydroxy-4-hydroxymethyl-pyridine-2-carboxylic acid hydroxyamide is administered in combination with a statin (e.g., atorvastatin).

In a further embodiment of the first aspect of the invention, the compound is 5-[2-(4-fluoro-phenyl)-ethyl]-3-hydroxy-4-hydroxymethyl-pyridine-2-carboxylic acid hydroxyamide. In one embodiment, 5-[2-(4-fluoro-phenyl)-ethyl]-3-hydroxy-4-hydroxymethyl-pyridine-2-carboxylic acid hydroxyamide is administered in combination with a statin (e.g., atorvastatin).

In additional embodiments of the first aspect of the invention, the subject has been diagnosed with atherosclerosis, hypercholesterolemia, hypertriglyceridemia, diabetic complications, dyslipidemia, hyperlipidemia, hypoalphalipoproteinemia, metabolic syndrome, stroke, vascular dementia, chronic kidney disease, coronary heart disease, coronary artery disease, retinopathy, inflammation, thrombosis, peripheral vascular disease or congestive heart failure. In some embodiments, the hypercholesterolemia is heterozygous familial hypercholesterolemia, and in other embodiments, the hypercholesterolemia is homozygous familial hypercholesterolemia.

In some embodiments of the first aspect of the invention, the subject has been diagnosed with atherosclerosis. In some embodiments of the first aspect of the invention, the subject has been diagnosed with hypercholesterolemia. In some embodiments of the first aspect of the invention, the subject has been diagnosed with hypertriglyceridemia. In some embodiments of the first aspect of the invention, the subject has been diagnosed with diabetic complications. In some embodiments of the first aspect of the invention, the subject has been diagnosed with dyslipidemia. In some embodiments of the first aspect of the invention, the subject has been diagnosed with hyperlipidemia. In some embodiments of the first aspect of the invention, the subject has been diagnosed with hypoalphalipoproteinemia. In some embodiments of the first aspect of the invention, the subject has been diagnosed with metabolic syndrome. In some embodiments of the first aspect of the invention, the subject has been diagnosed with stroke. In some embodiments of the first aspect of the invention, the subject has been diagnosed with vascular dementia. In some embodiments of the first aspect of the invention, the subject has been diagnosed with chronic kidney disease. In some embodiments of the first aspect of the invention, the subject has been diagnosed with coronary heart disease. In some embodiments of the first aspect of the invention, the subject has been diagnosed with coronary artery disease. In some embodiments of the first aspect of the invention, the subject has been diagnosed with retinopathy. In some embodiments of the first aspect of the invention, the subject has been diagnosed with inflammation. In some embodiments of the first aspect of the invention, the subject has been diagnosed with thrombosis. In some embodiments of the first aspect of the invention, the subject has been diagnosed with peripheral vascular disease. In some embodiments of the first aspect of the invention, the subject has been diagnosed with congestive heart failure In a second aspect, the invention features a method of treating atherosclerosis, hypercholesterolemia, hypertriglyceridemia, diabetic complications, dyslipidemia, hyperlipidemia, hypoalphalipoproteinemia, metabolic syndrome, stroke, vascular dementia, chronic kidney disease, coronary heart disease, coronary artery disease, retinopathy, inflammation, thrombosis, peripheral vascular disease or congestive heart failure. This method includes administering to a subject in need thereof, a therapeutically effective amount of a compound having the formula:

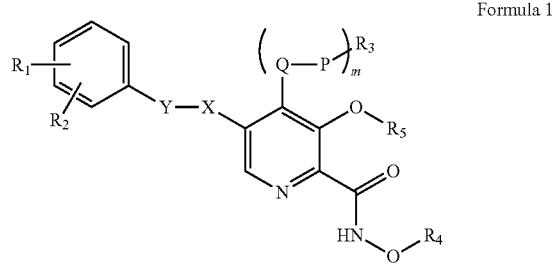

Formula 1 where Y—X is —C($R_7$)($R_{7a}$)N(R')C(O)—; —C($R_7$)($R_{7a}$)OC(O)—; —C($R_7$)($R_{7a}$)N(R')C($R_6$)($R_{6a}$)—; —C($R_7$)($R_{7a}$)S(O)$_2$C($R_6$)($R_{6a}$)—; —S(O)$_2$C($R_6$)($R_{6a}$)—; —C($R_7$)($R_{7a}$)C($R_6$)($R_{6a}$)—; —O—C($R_6$)($R_{6a}$)—; —N(R')C($R_6$)($R_{6a}$)—; or —C($R_7$)($R_{7a}$)OC($R_6$)($R_{6a}$)—, where each of $R_6$, $R_{6a}$, $R_7$, and $R_{7a}$, is, independently, selected from H, $C_{1-6}$ alkyl, $C_{1-6}$ fluoroalkyl, benzyl, phenyl, and heterocycle, R' is selected from H, $C_{1-6}$ alkyl, benzyl, S(O)$_2$R", and C(O)R", and R" is selected from $C_{1-6}$ alkyl, $C_{1-6}$ fluoroalkyl, benzyl, phenyl, and heterocycle; when Q is H, P and $R_3$ are absent; when Q is CH$_3$, P and $R_3$ are absent; Q is CH$_2$, or C(O); when P is H, $R_3$ is absent; P is —O—, —N($R_8$)($R_{8a}$), or is absent, where $R_8$ and $R_{8a}$ are selected independently from H, $C_{1-6}$ alkyl, $C_{1-6}$ fluoroalkyl, benzyl, phenyl, and heterocycle; $R_1$ is absent, $C_{1-6}$ alkyl, $C_{1-6}$ branched alkyl, $C_{1-6}$ alkene, halogen (F, Cl, Br, I), OH, —O—($C_{1-6}$ alkyl), —O—($C_{1-6}$ branched alkyl), —C(O)($R_9$), —C(O)O($R_9$), —C(O)N($R_9$)($R_{9a}$), or —S(O)$_2$N($R_9$)($R_{9a}$), where $R_9$ and $R_{9a}$ are selected independently from H, $C_{1-6}$ alkyl, $C_{1-6}$ fluoroalkyl, benzyl, phenyl, and heterocycle; $R_2$ is absent, $C_{1-6}$ alkyl, $C_{1-6}$ branched alkyl, $C_{1-6}$ alkene, halogen (F, Cl, Br, I), OH, —O—($C_{1-6}$ alkyl), —O—($C_{1-6}$ branched alkyl), —C(O)($R_{10}$), —C(O)O($R_{10}$), or —C(O)N($R_{10}$)($R_{10a}$), where $R_{10}$ and $R_{10a}$ are selected independently from H, $C_{1-6}$ alkyl, $C_{1-6}$ fluoroalkyl, benzyl, phenyl, and heterocycle; or $R_1$ and $R_2$ are ortho substituents that together form a carbocyclic or heterocyclic ring system; $R_3$ is H, $C_{1-6}$ alkyl, $C_{1-6}$ fluoroalkyl, benzyl, phenyl, heterocycle, or is absent; $R_5$ is H, $C_{1-6}$ alkyl, $C_{1-6}$ fluoroalkyl, benzyl, phenyl, or heterocycle, or $R_3$ and $R_5$ combine to form a heterocyclic ring system; $R_4$ is H, $C_{1-6}$ alkyl, $C_{1-6}$ fluoroalkyl, benzyl, phenyl, or heterocycle, and m is 0 or 1; or a pharmaceutically acceptable salt or solvate thereof.

In some embodiments of the second aspect of the invention, the method treats atherosclerosis. In some embodiments of the second aspect of the invention, the method treats hypercholesterolemia. In some embodiments of the second aspect of the invention, the method treats hypertriglyceridemia. In some embodiments of the second aspect of the invention, the method treats diabetic complications. In some embodiments of the second aspect of the invention, the method treats dyslipidemia. In some embodiments of the second aspect of the invention, the method treats hyperlipidemia. In some embodiments of the second aspect of the invention, the method treats hypoalphalipoproteinemia. In some embodiments of the second aspect of the invention, the method treats metabolic syndrome. In some embodiments of the second aspect of the invention, the method treats stroke. In some embodiments of the second aspect of the invention, the method treats vascular dementia. In some embodiments of the second aspect of the invention, the method treats chronic kidney disease. In some embodiments of the second aspect of the invention, the method treats coronary heart disease. In some embodiments of the second aspect of the invention, the method treats coronary artery disease. In some embodiments of the second aspect of the invention, the method treats retinopathy. In some embodiments of the second aspect of the invention, the method treats inflammation. In some embodiments of the second aspect of the invention, the method treats thrombosis. In some embodiments of the second aspect of the invention, the method treats peripheral vascular disease. In some embodiments of the second aspect of the invention, the method treats congestive heart failure.

In some embodiments of the second aspect of the invention, Q is $CH_2$, P is —O—, $R_3$ is H, Y—X is —$CH_2NHCH_2$— or —$CH_2NHC(O)$—, $R_1$ is selected from a halogen, —OH or —$OCH_3$, $R_2$ is absent or selected from —OH and a halogen, $R_4$ is H or benzyl, and $R_5$ is H or benzyl, or a pharmaceutically acceptable salt or solvate thereof.

In other embodiments of the second aspect of the invention, Q is $CH_2$, P is —O—, $R_3$ is $CH_3$, Y—X is —$CH_2OCH_2$—, $R_1$ is selected from a halogen, —OH or —$OCH_3$, $R_2$ is absent or selected from —OH and a halogen, $R_4$ is H or benzyl, and $R_5$ is H or benzyl or a pharmaceutically acceptable salt or solvate thereof.

In a particular embodiment of the second aspect of the invention, the compound is 5-[(4-fluoro-phenylamino)-methyl]-3-hydroxy-4-hydroxymethyl-pyridine-2-carboxylic acid hydroxyamide. In one embodiment, 5-[(4-fluoro-phenylamino)-methyl]-3-hydroxy-4-hydroxymethyl-pyridine-2-carboxylic acid hydroxyamide is administered in combination with a statin (e.g., atorvastatin).

In another embodiment of the second aspect of the invention, the compound is 5-(4-fluoro-phenoxymethyl)-3-hydroxy-4-hydroxymethyl-pyridine-2-carboxylic acid hydroxyamide. In one embodiment, 5-(4-fluoro-phenoxymethyl)-3-hydroxy-4-hydroxymethyl-pyridine-2-carboxylic acid hydroxyamide is administered in combination with a statin (e.g., atorvastatin).

In a further embodiment of the second aspect of the invention, the compound is 5-[2-(4-fluoro-phenyl)-ethyl]-3-hydroxy-4-hydroxymethyl-pyridine-2-carboxylic acid hydroxyamide. In one embodiment, 5-[2-(4-fluoro-phenyl)-ethyl]-3-hydroxy-4-hydroxymethyl-pyridine-2-carboxylic acid hydroxyamide is administered in combination with a statin (e.g., atorvastatin).

In an embodiment of the second aspect of the invention, the hypercholesterolemia is heterozygous familial hypercholesterolemia, and in another embodiment of the second aspect of the invention, the hypercholesterolemia is homozygous familial hypercholesterolemia.

In additional embodiments of the first aspect or the second aspect of the invention, a pharmaceutical composition including the compound or the salt or solvate thereof is administered to the subject.

In a third aspect, the invention features a method of inducing low density lipoprotein receptor (LDLR) expression in a cell. This method includes contacting the cell with an effective amount of a compound having the formula:

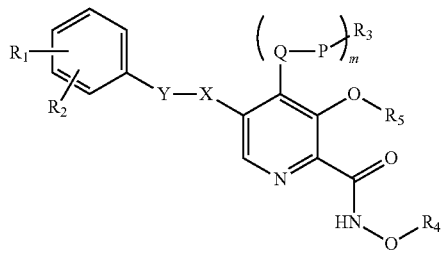

Formula 1 where Y—X is —$C(R_7)(R_{7a})N(R')C(O)$—; —$C(R_7)(R_{7a})OC(O)$—; —$C(R_7)(R_{7a})N(R')C(R_6)(R_{6a})$—; —$C(R_7)(R_{7a})S(O)_2C(R_6)(R_{6a})$—; —$S(O)_2C(R_6)(R_{6a})$—; —$C(R_7)(R_{7a})C(R_6)(R_{6a})$—; —O—$C(R_6)(R_{6a})$—; —$N(R')C(R_6)(R_{6a})$—; or —$C(R_7)(R_{7a})OC(R_6)(R_{6a})$—, where each of $R_6$, $R_{6a}$, $R_7$, and $R_{7a}$, is, independently, selected from H, $C_{1-6}$ alkyl, $C_{1-6}$ fluoroalkyl, benzyl, phenyl, and heterocycle, R' is selected from H, $C_{1-6}$ alkyl, benzyl, $S(O)_2R''$, and $C(O)R''$, and R'' is selected from $C_{1-6}$ alkyl, $C_{1-6}$ fluoroalkyl, benzyl, phenyl, and heterocycle; when Q is H, P and $R_3$ are absent; when Q is $CH_3$, P and $R_3$ are absent; Q is $CH_2$, or C(O); when P is H, $R_3$ is absent; P is —O—, —$N(R_8)(R_{8a})$, or is absent, where $R_8$ and $R_{8a}$ are selected independently from H, $C_{1-6}$ alkyl, $C_{1-6}$ fluoroalkyl, benzyl, phenyl, and heterocycle; $R_1$ is absent, $C_{1-6}$ alkyl, $C_{1-6}$ branched alkyl, $C_{1-6}$ alkene, halogen (F, Cl, Br, I), OH, —O—($C_{1-6}$ alkyl), —O—($C_{1-6}$ branched alkyl), —$C(O)(R_9)$, —$C(O)O(R_9)$, —$C(O)N(R_9)(R_{9a})$, or —$S(O)_2N(R_9)(R_{9a})$, where $R_9$ and $R_{9a}$ are selected independently from H, $C_{1-6}$ alkyl, $C_{1-6}$ fluoroalkyl, benzyl, phenyl, and heterocycle; $R_2$ is absent, $C_{1-6}$ alkyl, $C_{1-6}$ branched alkyl, $C_{1-6}$ alkene, halogen (F, Cl, Br, I), OH, —O—($C_{1-6}$ alkyl), —O—($C_{1-6}$ branched alkyl), —$C(O)(R_{10})$, —$C(O)O(R_{10})$, or —$C(O)N(R_{10})(R_{10a})$, where $R_{10}$ and $R_{10a}$ are selected independently from H, $C_{1-6}$ alkyl, $C_{1-6}$ fluoroalkyl, benzyl, phenyl, and heterocycle; or $R_1$ and $R_2$ are ortho substituents that together form a carbocyclic or heterocyclic ring system; $R_3$ is H, $C_{1-6}$ alkyl, $C_{1-6}$ fluoroalkyl, benzyl, phenyl, heterocycle, or is absent; $R_5$ is H, $C_{1-6}$ alkyl, $C_{1-6}$ fluoroalkyl, benzyl, phenyl, or heterocycle; or $R_3$ and $R_5$ combine to form a heterocyclic ring system; $R_4$ is H, $C_{1-6}$ alkyl, $C_{1-6}$ fluoroalkyl, benzyl, phenyl, or heterocycle; and m is 0 or 1; or a pharmaceutically acceptable salt or solvate thereof.

In an embodiment of the third aspect of the invention, Q is $CH_2$, P is —O—, $R_3$ is H, Y—X is —$CH_2NHCH_2$— or —$CH_2NHC(O)$—, $R_1$ is selected from a halogen, —OH or —$OCH_3$, $R_2$ is absent or selected from —OH and a halogen, $R_4$ is H or benzyl, and $R_5$ is H or benzyl, or a pharmaceutically acceptable salt or solvate thereof.

In another embodiment of the third aspect of the invention, Q is $CH_2$, P is —O—, $R_3$ is $CH_3$, Y—X is —$CH_2OCH_2$—, $R_1$ is selected from a halogen, —OH or —$OCH_3$, $R_2$ is absent or selected from —OH and a halogen, $R_4$ is H or benzyl, and $R_5$ is H or benzyl or a pharmaceutically acceptable salt or solvate thereof.

In a particular embodiment of the third aspect of the invention, the compound is 5-[(4-fluoro-phenylamino)-methyl]-3-hydroxy-4-hydroxymethyl-pyridine-2-carboxylic acid hydroxyamide. In one embodiment, 5-[(4-fluoro-phenylamino)-methyl]-3-hydroxy-4-hydroxymethyl-pyridine-2-carboxylic acid hydroxyamide is administered in combination with a statin (e.g., atorvastatin).

In another embodiment of the third aspect of the invention, the compound is 5-(4-fluoro-phenoxymethyl)-3-hydroxy-4-hydroxymethyl-pyridine-2-carboxylic acid hydroxyamide. In one embodiment, 5-(4-fluoro-phenoxymethyl)-3-hydroxy-4-hydroxymethyl-pyridine-2-carboxylic acid hydroxyamide is administered in combination with a statin (e.g., atorvastatin).

In a further embodiment of the third aspect of the invention, the compound is 5-[2-(4-fluoro-phenyl)-ethyl]-3-hydroxy-4-hydroxymethyl-pyridine-2-carboxylic acid hydroxyamide. In one embodiment, 5-[2-(4-fluoro-phenyl)-ethyl]-3-hydroxy-4-hydroxymethyl-pyridine-2-carboxylic acid hydroxyamide is administered in combination with a statin (e.g., atorvastatin).

In an additional embodiment of the third aspect of the invention, the cell is a cardiovascular system cell, and in another embodiment of the third aspect of the invention, the cell is in a tissue, and in a further embodiment, the cell or the tissue is in a subject.

In a fourth aspect, the invention features a method of modulating LDLR mRNA activity in a cell. This method includes contacting the cell with an effective amount of a compound having the formula:

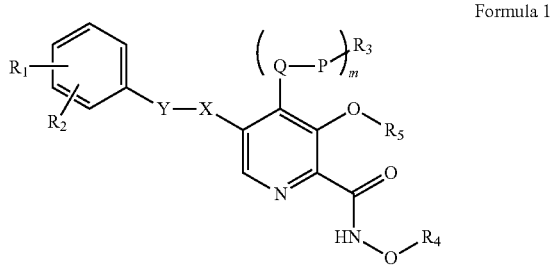

Formula 1 where Y—X is —C($R_7$)($R_{7a}$)N(R')C(O)—; —C($R_7$)($R_{7a}$)OC(O)—; —C($R_7$)($R_{7a}$)N(R')C($R_6$)($R_{6a}$)—; —C($R_7$)($R_{7a}$)S(O)$_2$C($R_6$)($R_{6a}$)—; —S(O)$_2$C($R_6$)($R_{6a}$)—; —C($R_7$)($R_{7a}$)C($R_6$)($R_{6a}$)—; —O—C($R_6$)($R_{6a}$)—; —N(R')C($R_6$)($R_{6a}$)—; or —C($R_7$)($R_{7a}$)OC($R_6$)($R_{6a}$)—, where each of $R_6$, $R_{6a}$, $R_7$, and $R_{7a}$, is, independently, selected from H, $C_{1-6}$ alkyl, $C_{1-6}$ fluoroalkyl, benzyl, phenyl, and heterocycle, R' is selected from H, $C_10.6$ alkyl, benzyl, S(O)$_2$R", and C(O)R", and R" is selected from $C_{1-6}$ alkyl, $C_{1-6}$ fluoroalkyl, benzyl, phenyl, and heterocycle; when Q is H, P and $R_3$ are absent; when Q is CH$_3$, P and $R_3$ are absent; Q is CH$_2$, or C(O); when P is H, $R_3$ is absent; P is —O—, —N($R_8$)($R_{8a}$), or is absent, where the $R_5$ and $R_{8a}$ are selected independently from the group consisting of H, $C_{1-6}$ alkyl, $C_{1-6}$ fluoroalkyl, benzyl, phenyl, and heterocycle, $R_1$ is absent, $C_{1-6}$ alkyl, $C_{1-6}$ branched alkyl, $C_{1-6}$ alkene, halogen (F, Cl, Br, I), OH, —O—($C_{1-6}$ alkyl), —O—($C_{1-6}$ branched alkyl), —C(O)($R_9$), —C(O)O($R_9$), —C(O)N($R_9$)($R_{9a}$), or —S(O)$_2$N($R_9$)($R_{9a}$), where $R_9$ and $R_{9a}$ are selected independently H, $C_{1-6}$ alkyl, $C_{1-6}$ fluoroalkyl, benzyl, phenyl, and heterocycle, $R_2$ is absent, $C_{1-6}$ alkyl, $C_{1-6}$ branched alkyl, $C_{1-6}$ alkene, halogen (F, Cl, Br, I), OH, —O—($C_{1-6}$ alkyl), —O—($C_{1-6}$ branched alkyl), —C(O)($R_{10}$), —C(O)O($R_{10}$), or —C(O)N($R_{10}$)($R_{10a}$), where $R_{10}$ and $R_{10a}$ are selected independently from H, $C_{1-6}$ alkyl, $C_{1-6}$ fluoroalkyl, benzyl, phenyl, and heterocycle; or $R_1$ and $R_2$ are ortho substituents that together form a carbocyclic or heterocyclic ring system; $R_3$ is H, $C_{1-6}$ alkyl, $C_{1-6}$ fluoroalkyl, benzyl, phenyl, heterocycle, or is absent; $R_5$ is H, $C_{1-6}$ alkyl, $C_{1-6}$ fluoroalkyl, benzyl, phenyl, or heterocycle; or $R_3$ and $R_5$ combine to form a heterocyclic ring system; $R_4$ is H, $C_{1-6}$ alkyl, $C_{1-6}$ fluoroalkyl, benzyl, phenyl, or heterocycle; and m is 0 or 1; or a pharmaceutically acceptable salt or solvate thereof.

In some embodiments of the fourth aspect of the invention Q is CH$_2$, P is —O—, $R_3$ is H, Y—X is —CH$_2$NHCH$_2$— or —CH$_2$NHC(O)—, $R_1$ is selected from a halogen, —OH or —OCH$_3$, $R_2$ is absent or selected from —OH and a halogen, $R_4$ is H or benzyl, and $R_5$ is H or benzyl, or a pharmaceutically acceptable salt or solvate thereof.

In other embodiments of the fourth aspect of the invention Q is CH$_2$, P is —O—, $R_3$ is CH$_3$, Y—X is —CH$_2$OCH$_2$—, $R_1$ is selected from a halogen, —OH or —OCH$_3$, $R_2$ is absent or selected from —OH and a halogen, $R_4$ is H or benzyl, and $R_5$ is H or benzyl or a pharmaceutically acceptable salt or solvate thereof.

In a particular embodiment of the fourth aspect of the invention, the compound is 5-[(4-fluoro-phenylamino)-methyl]-3-hydroxy-4-hydroxymethyl-pyridine-2-carboxylic acid hydroxyamide. In one embodiment, 5-[(4-fluoro-phenylamino)-methyl]-3-hydroxy-4-hydroxymethyl-pyridine-2-carboxylic acid hydroxyamide is administered in combination with a statin (e.g., atorvastatin).

In another embodiment of the fourth aspect of the invention, the compound is 5-(4-fluoro-phenoxymethyl)-3-hydroxy-4-hydroxymethyl-pyridine-2-carboxylic acid hydroxyamide. In one embodiment, 5-(4-fluoro-phenoxymethyl)-3-hydroxy-4-hydroxymethyl-pyridine-2-carboxylic acid hydroxyamide is administered in combination with a statin (e.g., atorvastatin).

In a further embodiment of the fourth aspect of the invention, the compound is 5-[2-(4-fluoro-phenyl)-ethyl]-3-hydroxy-4-hydroxymethyl-pyridine-2-carboxylic acid hydroxyamide. In one embodiment, 5-[2-(4-fluoro-phenyl)-ethyl]-3-hydroxy-4-hydroxymethyl-pyridine-2-carboxylic acid hydroxyamide is administered in combination with a statin (e.g., atorvastatin).

In other embodiment of the fourth aspect of the invention, modulating includes inducing LDLR mRNA activity, and in another embodiment of the fourth aspect of the invention modulating includes stabilizing LDLR mRNA activity.

In additional embodiments of the first aspect of the invention, the method includes administering a second cholesterol lowering agent to the subject. In some embodiments the second cholesterol lowering agent is a lipase inhibitor, a 3-hydroxy-3-methyl-glutaryl-coenzyme A (HMG CoA) reductase inhibitor, a HMG CoA synthase inhibitor, a cholesteryl ester transfer protein (CETP) inhibitor, a bile acid absorption inhibitor, a cholesterol absorption inhibitor, a cholesterol synthesis inhibitor, a squalene synthetase inhibitor, a squalene epoxidase or cyclase inhibitor or a combination of both, a microsomal triglyceride transfer protein (MTP)/Apolipoprotein B (ApoB) secretion inhibitor, a fibrate, niacin alone or in combination with lovastatin, an ion-exchange resin, an antioxidant, an acyl-coenzyme A: cholesterol acyltransferase (ACAT) inhibitor and a bile acid sequestrant, an HMG-CoA reductase gene expression inhibitor, an HMG-CoA synthase gene expression inhibitor, a proprotein convertase subtilisin kexin type 9 (PCSK9) inhibitor. In one embodiment, 5-(4-fluoro-phenoxymethyl)-3-hydroxy-4-hydroxymethyl-pyridine-2-carboxylic acid hydroxyamide is administered in combination with a statin (e.g., in combination with atorvastatin).

In further embodiments of the first aspect or the second aspect of the invention, the subject, prior to administration of the compound of Formula 1, was treated with a lipase inhibitor, a 3-hydroxy-3-methyl-glutaryl-coenzyme A (HMG CoA) reductase inhibitor, a HMG CoA synthase inhibitor, a cholesteryl ester transfer protein (CETP) inhibitor, a bile acid absorption inhibitor, a cholesterol absorption inhibitor, a cholesterol synthesis inhibitor, a squalene synthetase inhibitor, a squalene epoxidase or cyclase inhibitor or a combination of both, a microsomal triglyceride transfer protein (MTP)/Apolipoprotein B (ApoB) secretion inhibitor, a fibrate, niacin alone or in combination with lovastatin, an ion-exchange resin, an antioxidant, an acyl-coenzyme A: cholesterol acyltransferase (ACAT) inhibitor and a bile acid sequestrant, an HMG-CoA reductase gene expression inhibitor, an HMG-CoA synthase gene expression inhibitor, or a proprotein convertase subtilisin kexin type 9 (PCSK9) inhibitor. In some embodiments, the prior administration did not effectively lower the cholesterol level in the bloodstream of the subject.

In a fifth aspect, the invention features a use of a compound having the formula:

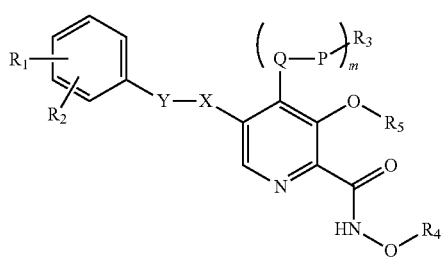

Formula 1 where Y—X is —C($R_7$)($R_{7a}$)N(R')C(O)—; —C($R_7$)($R_{7a}$)OC(O)—; —C($R_7$)($R_{7a}$)N(R')C($R_6$)($R_{6a}$)—; —C($R_7$)($R_{7a}$)S(O)$_2$C($R_6$)($R_{6a}$)—; —S(O)$_2$C($R_6$)($R_{6a}$)—; —C($R_7$)($R_{7a}$)C($R_6$)($R_{6a}$)—; —O—C($R_6$)($R_{6a}$)—; —N(R')C($R_6$)($R_{6a}$)—; or —C($R_7$)($R_{7a}$)OC($R_6$)($R_{6a}$)—, where each of $R_6$, $R_{6a}$, $R_7$, and $R_{7a}$, is, independently, selected from H, $C_{1-6}$ alkyl, $C_{1-6}$ fluoroalkyl, benzyl, phenyl, and heterocycle, R' is selected from H, $C_{1-6}$ alkyl, benzyl, S(O)$_2$R", and C(O)R", and R" is selected from $C_{1-6}$ alkyl, $C_{1-6}$ fluoroalkyl, benzyl, phenyl, and heterocycle; when Q is H, P and $R_3$ are absent; when Q is CH$_3$, P and $R_3$ are absent; Q is CH$_2$, or C(O); when P is H, $R_3$ is absent; P is —O—, —N($R_8$)($R_{8a}$), or is absent, where $R_5$ and $R_{8a}$ are selected independently from H, $C_{1-6}$ alkyl, $C_{1-6}$ fluoroalkyl, benzyl, phenyl, and heterocycle, $R_1$ is absent, $C_{1-6}$ alkyl, $C_{1-6}$ branched alkyl, $C_{1-6}$ alkene, halogen (F, Cl, Br, I), OH, —O—($C_{1-6}$ alkyl), —O—($C_{1-6}$ branched alkyl), —C(O)($R_9$), —C(O)O($R_9$), —C(O)N($R_9$)($R_{9a}$), or —S(O)$_2$N($R_9$)($R_{9a}$), where $R_9$ and $R_{9a}$ are selected independently from H, $C_{1-6}$ alkyl, $C_{1-6}$ fluoroalkyl, benzyl, phenyl, and heterocycle, $R_2$ is absent, $C_{1-6}$ alkyl, $C_{1-6}$ branched alkyl, $C_{1-6}$ alkene, halogen (F, Cl, Br, I), OH, —O—($C_{1-6}$ alkyl), —O—($C_{1-6}$ branched alkyl), —C(O)($R_{10}$), —C(O)O($R_{10}$), or —C(O)N($R_{10}$)($R_{10a}$), where $R_{10}$ and $R_{10a}$ are selected independently from H, $C_{1-6}$ alkyl, $C_{1-6}$ fluoroalkyl, benzyl, phenyl, and heterocycle, or $R_1$ and $R_2$ are ortho substituents that together form a carbocyclic or heterocyclic ring system; $R_3$ is H, $C_{1-6}$ alkyl, $C_{1-6}$ fluoroalkyl, benzyl, phenyl, heterocycle, or is absent; $R_5$ is H, $C_{1-6}$ alkyl, $C_{1-6}$ fluoroalkyl, benzyl, phenyl, or heterocycle; or $R_3$ and $R_5$ combine to form a heterocyclic ring system; $R_4$ is H, $C_{1-6}$ alkyl, $C_{1-6}$ fluoroalkyl, benzyl, phenyl, or heterocycle; and m is 0 or 1; or a pharmaceutically acceptable salt or solvate thereof, in the production of a medicament for lowering the cholesterol level in the bloodstream of a subject, for treating atherosclerosis, hypercholesterolemia, hypertriglyceridemia, diabetic complications, dyslipidemia, hyperlipidemia, hypoalphalipoproteinemia, metabolic syndrome, stroke, vascular dementia, chronic kidney disease, coronary heart disease, coronary artery disease, retinopathy, inflammation, thrombosis, peripheral vascular disease or congestive heart failure, for inducing low density lipoprotein receptor (LDLR) expression in a cell or a tissue, or for inducing or stabilizing LDLR mRNA activity in a cell or a tissue.

In a particular embodiment of the fifth aspect of the invention, the compound is 5-[(4-fluoro-phenylamino)-methyl]-3-hydroxy-4-hydroxymethyl-pyridine-2-carboxylic acid hydroxyamide.

In another particular embodiment of the fifth aspect of the invention, the compound is 5-(4-fluoro-phenoxymethyl)-3-hydroxy-4-hydroxymethyl-pyridine-2-carboxylic acid hydroxyamide.

In a further particular embodiment of the fifth aspect of the invention, the compound is 5-[2-(4-fluoro-phenyl)-ethyl]-3-hydroxy-4-hydroxymethyl-pyridine-2-carboxylic acid hydroxyamide.

Definitions

The term "coronary artery disease," as used herein, encompasses atherosclerotic plaque (e.g., prevention, regression, stabilization), vulnerable plaque (e.g., prevention, regression, stabilization), vulnerable plaque area (reduction), arterial calcification (e.g., calcific aortic stenosis), increased coronary artery calcium score, dysfunctional vascular reactivity, vasodilation disorders, coronary artery spasm, first myocardial infarction, myocardia re-infarction, ischemic cardiomyopathy, stent restenosis, PTCA restenosis, arterial restenosis, coronary bypass graft restenosis, vascular bypass restenosis, decreased exercise treadmill time, angina pectoris/chest pain, unstable angina pectoris, exertional dyspnea, decreased exercise capacity, ischemia (reduce time to), silent ischemia (reduce time to), increased severity and frequency of ischemic symptoms, and reperfusion after thrombolytic therapy for acute myocardial infarction.

The term "hypertension" encompasses lipid disorders with hypertension, systolic hypertension, and diastolic hypertension.

The term "peripheral vascular disease", as used herein, encompasses peripheral vascular disease and claudication.

The term "diabetes," as used herein, refers to any of a number of diabetogenic states including type I diabetes, type II diabetes, Syndrome X, Metabolic syndrome, lipid disorders associated with insulin resistance, impaired glucose tolerance, non-insulin dependent diabetes, microvascular diabetic complications, reduced nerve conduction velocity, reduced or loss of vision, diabetic retinopathy, increased risk of amputation, decreased kidney function, kidney failure, insulin resistance syndrome, pluri-metabolic syndrome, central adiposity (visceral)(upper body), diabetic dyslipidemia, decreased insulin sensitization, diabetic retinopathy/neuropathy, diabetic nephropathy/micro and macro angiopathy and micro/macro albuminuria, diabetic cardiomyopathy, diabetic gastroparesis, obesity, increased hemoglobin glycoslation (including HbAI C), improved glucose control, impaired renal function (dialysis or end stage), and impaired hepatic function (mild, moderate, or severe).

"Metabolic syndrome," also known as "Syndrome X," refers to a common clinical disorder that is defined as the presence of increased insulin concentrations in association with other disorders including hyperlipidemia, dyslipidemia, viceral obesity, hyperglycemia, hypertension, and potentially hyperuricemis and renal dysfunction.

The term "Vitamin $B_6$" as used herein refers to one or more of three compounds that are commonly referred to as vitamin $B_6$ namely pyridoxal, pyridoxamine, and pyridoxine. Pyridoxine differs from pyridoxamine by the substituent at the '4' position. Pyridoxine based on a pyridine ring, with hydroxyl, methyl, and hydroxymethyl substituents and is converted in vivo to pyridoxal 5-phosphate, the biologically active form of pyridoxine.

The terms "comprising" and "including" as used herein, are used in their open, non-limiting sense.

The term "$C_{1-6}$ alkyl," as used herein, means saturated monovalent hydrocarbon radicals having straight or branched moieties and containing from 1 to 6 carbon atoms. The $C_{1-6}$ alkyl group may be substituted or unsubstituted. Examples of such groups include, but are not limited to, methyl, ethyl, propyl, isopropyl, n-butyl, isobutyl, and tertbutyl. The term "$C_{1-6}$ fluoroalkyl" refers to a $C_{1-6}$ alkyl substituted with one or more fluorine atoms. Exemplary $C_{1-6}$ fluoroalkyl groups include, without limitation, fluoromethyl, trifluoromethyl, and pentafluoroethyl. The term "$C_1$-6 branched alkyl" refers to alkyl group that include one or more tertiary or quaternary carbon atoms.

By "$C_{1-6}$ alkenyl" is meant a branched or unbranched hydrocarbon group containing one or more double bonds and having from 1 to 6 carbon atoms. For example, $C_2$ alkenyl may optionally include monocyclic or polycyclic rings, in which each ring desirably has from three to six members. The $C_{2-4}$ alkenyl group may be substituted or unsubstituted.

By "carbocyclic group" or "carbocyclic ring" is meant a monocyclic or polycyclic ring system which is saturated, partially unsaturated, or unsaturated (aromatic), and which consists of 3 to 8 carbon atoms (unless otherwise specified). Carbocyclic groups include alkyl groups substituted with such a monocyclic or polycyclic ring system. Exemplary cyclic groups include phenyl, benzyl, cyclopropyl, cyclobutyl, cyclopentyl, 2-phenylcyclopropane, and cyclohexyl. The carbocyclic group may be substituted or unsubstituted.

The terms "heterocycle" and "heterocyclic ring," as used herein, mean aromatic or non-aromatic, monocyclic, bicyclic, tricyclic, tetracyclic, or spirocyclic group, having a total of from 3 to 10 atoms in its ring system, and containing from 2 to 9 carbon atoms and from one to four heteroatoms each independently selected from O, S, and N and with the proviso that the ring of the group does not contain two adjacent O atoms or two adjacent S atoms. Furthermore, such heterocycle groups may contain an oxo substituent at any available atom that will result in a stable compound. For example, such a group may contain an oxo atom at an available carbon or nitrogen atom. Such a group may contain more than one oxo substituent if chemically feasible. In addition, it is to be understood that when such a heterocycle group contains a sulfur atom, the sulfur atom may be oxidized with one or two oxygen atoms to afford either a sulfoxide or sulfone. An example of a 4-membered heterocyclic group is azetidinyl (derived from azetidine). An example of a 5-membered heterocyclic group is thiazolyl, and an example of a 10-membered heterocyclic group is quinolinyl. Further examples of such heterocycle groups include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, and quinolizinyl. The heterocycle group may be substituted or unsubstituted.

As used herein, the terms "benzyl" and "phenyl" refer to both substituted and unsubstitued benzyl and phenyl groups, respectively.

As used herein, the term "substituted" refers to a group (e.g., a "$C_{1-6}$ alkyl," "$C_{1-6}$ alkenyl," "$C_{1-6}$ fluoroalkyl," "benzyl," "phenyl," "heterocycle," or "carbocyclic group") in which one or more hydrogen atoms in the group are, independently, replaced with a substituent selected from, for example, methyl, ethyl, n-propyl, isopropyl, hydroxy, methoxy, ethoxy, fluorine, chlorine, bromine, iodine, cyano, nitro, amino, alkylamino, dialkylamino, carboxy, chloromethyl, trichloromethyl, trifluoromethyl, methoxyethyl, —$CH_2C(O)NH_2$, —$C(O)CH_2N(CH_3)_2$, —$CH_2CH_2OH$, —$CH_2OC(O)NH_2$, —$CH_2CH_2NH_2$, —$CH_2CH_2$ $CH_2NEt2$, —$CH_2OCH_3$, —$C(O)NH_2$, —$C(NH)NH_2$, —$C(=NH)OEt$, —$C(O)NH$-cyclopropyl, —$C(O)NHCH_2CH_2OCH_3$, —$C(O)CH_2CH_2NHCH_3$, —$CH_2CH_2F$, or —$CH_2C(O)NHCH_3$.

The term "solvate," as used herein, means a pharmaceutically acceptable solvate form of a compound of the present invention that retains the biological effectiveness of such compound. Examples of solvates include, but are not limited to, compounds of the invention in combination with water, isopropanol, ethanol, methanol, dimethylsulfoxide (DMSO), ethyl acetate, acetic acid, ethanolamine, or mixtures thereof. It is specifically contemplated that in the present invention one solvent molecule can be associated with one molecule of the compounds of the present invention, such as a hydrate. Furthermore, it is specifically contemplated that in the present invention, more than one solvent molecule may be associated with one molecule of the compounds of the present invention, such as a dihydrate. Additionally, it is specifically contemplated that in the present invention less than one solvent molecule may be associated with one molecule of the compounds of the present invention, such as a hemihydrate. Furthermore, solvates of the present invention are contemplated as solvates of compounds of the present invention that retain the biological effectiveness of the non-hydrate form of the compounds.

A "pharmaceutically acceptable salt" as used herein means a salt that retains the biological effectiveness of the free acids and bases of the specified derivative, containing pharmacologically acceptable anions or cations, and is not biologically or otherwise undesirable. Examples of pharmaceutically acceptable salts include, but are not limited to, acetate, acrylate, benzenesulfonate, benzoate (such as chlorobenzoate, methylbenzoate, dinitrobenzoate, hydroxybenzoate, and methoxybenzoate), bicarbonate, bisulfate, bisulfite, bitartrate, borate, bromide, butyne-1, 4-dioate, calcium edetate, camsylate, carbonate, chloride, caproate, caprylate, clavulanate, citrate, decanoate, dihydrochloride, dihydrogenphosphate, edetate, edislyate, estolate, esylate, ethylsuccinate, formate, fumarate, gluceptate, gluconate, glutamate, glycollate, glycollylarsanilate, heptanoate, hexyne-1,6-dioate, hexylresorcinate, hydrabamine, hydrobromide, hydrochloride, hydroxybutyrate, iodide, isobutyrate, isothionate, lactate, lactobionate, laurate, malate, maleate, malonate, mandelate, mesylate, metaphosphate, methane-sulfonate, methylsulfate, monohydrogenphosphate, mucate, napsylate, naphthalene-1-sulfonate, naphthalene-2-sulfonate, nitrate, oleate, oxalate, pamoate (embonate), palmitate, pantothenate, phenylacetates, phenylbutyrate, phenylpropionate, phthalate, phospate/diphosphate, polygalacturonate, propanesulfonate, propionate, propiolate, pyrophosphate, pyrosulfate, salicylate, stearate, subacetate, suberate, succinate, sulfate, sulfonate, sulfite, tannate, tartrate, teoclate, tosylate, triethiodode, valerate salts, and cations, such as sodium, potassium, calcium, magnesium, ammonium, and tetraalkylammonium, among others.

The term "therapeutically effective amount," as used herein, means an amount of a compound of the present invention, or a pharmaceutically acceptable salt or solvate thereof, that, when administered to a mammal in need of such treatment, is sufficient to effect treatment, as defined herein.

An "effective amount" refers to an amount effective, at dosages and for periods of time necessary, to achieve the desired result, e.g., increase of LDLR levels in a cell or increase expression of a functional LDLR receptor in a cell. The increase of LDLR levels or increase in expression of a functional LDLR receptor may be one and a half-fold, two-fold, three-fold, four-fold, five-fold, six-fold, seven-fold, eight-fold, nine-fold, ten-fold, eleven-fold, twelve-fold, or fifteen-fold relative to the level prior to contacting the cell with a compound of the present invention or a pharmaceutically acceptable salt or solvate thereof.

The term "LDL-lowering amount," as used herein, refers to an amount of a compound of the present invention, or a pharmaceutically acceptable salt or solvate thereof, that, when administered to a mammal in need of such treatment, lowers the serum LDL level as compared to the serum LDL level prior to treatment. The serum LDL level may be one and a half-fold, two-fold, three-fold, four-fold, five-fold, six-fold, seven-fold, eight-fold, nine-fold, ten-fold, eleven-fold, twelve-fold, or fifteen-fold lower relative to the serum LDL level prior to treatment. The serum LDL level may be measured using standard methods, e.g., a lipid panel.

The term "tissue," as used herein, refers to a group or layer of similarly specialized cells that together perform certain special functions. Examples of tissues include liver, blood, adipose tissue, fatty tissue, subcutaneous tissue, and muscular tissue.

The term "organ," as used herein, refers to a group of tissues in a living organism, e.g., mammal, that have been adapted to perform a specific function. In mammals, for example, organs are grouped into organ systems, e.g., the esophagus, stomach, and liver are organs of the digestive system.

The term "cardiovascular system cell," as used herein, refers to a cell that is a part of the cardiovascular system that conveys blood through vessels to and from all parts of the body, carrying nutrients and oxygen to tissues and removing carbon dioxide and other wastes. A cardiovascular system cell may be part of a blood vessel or may be part of the blood itself.

The term "heterozygous familial hypercholesterolemia," as used herein, refers to a genetic condition that causes high low-density lipoprotein (LDL) cholesterol, where the subject has one familial hypercholesterolemia gene mutated on one allele.

The term "homozygous familial hypercholesterolemia," as used herein, refers to a genetic condition that causes high low-density lipoprotein (LDL) cholesterol, where the subject has one familial hypercholesterolemia gene mutated on both alleles.

Polygenic familial hypercholesterolemia and polygenic hypercholesterolemia refer to a genetic condition that causes high low-density lipoprotein (LDL) cholesterol, where the subject has several genes contributing to the disease.

The term "pharmaceutically acceptable formulation," as used herein, means a combination of a compound of the invention, or a pharmaceutically acceptable salt or solvate thereof, and a carrier, diluent, and/or excipients that are compatible with a compound of the present invention, and is not deleterious to the recipient thereof. Pharmaceutical formulations can be prepared by procedures known to those of ordinary skill in the art. For example, the compounds of the present invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as povidone, sodium starch glycolate, sodium carboxymethylcellulose, agar, calcium carbonate, and sodium bicarbonate; agents for retarding dissollution such as paraffin; resorption accelerators such as quaternary ammonium compounds; surface active agents such as cetyl alcohol, glycerol monostearate; adsorptive carriers such as keolin and bentonite; and lubricants such as talc, calcium and magnesium stearate and solid polyethylene glycols. Final pharmaceutical forms may be pills, tablets, powders, lozenges, saches, cachets, or sterile packaged powders, and the like, depending on the type of excipient used. Additionally, it is specifically contemplated that pharmaceutically acceptable formulations of the present invention can contain more than one active ingredient. For example, such formulations may contain more than one compound according to the present invention. Alternatively, such formulations may contain one or more compounds of the present invention and one or more additional cholesterol modulating agents. A pharmaceutically acceptable formulation may also include but is not limited to compounds, other than the compounds of formula I, having a structure such that, upon administration to a recipient or patient, a compound of this invention, active metabolite, or residue thereof is directly or indirectly provided.

The terms "treat," "treating," and "treatment" include: (i) preventing a disease or condition from occurring in a subject which may be predisposed to the condition, such that the treatment constitutes prophylactic treatment for the pathologic condition; (ii) modulating or inhibiting a disease or condition, i.e., arresting its development; (iii) relieving a disease or condition, i.e., causing regression of the disease or condition; or (iv) relieving and/or alleviating a disease or condition or the symptoms resulting from the disease or condition, e.g., relieving an inflammatory response without addressing the underlying disease or condition.

The terms "co-administration," "co-administering," "co-administer," "co-administered," or "combination therapy," as used herein, refer to the administration of a combination of at least a first agent and a second agent or two or more agents according to the present invention. Such co-administration can be performed such that two or multiple agents are part of the same composition or part of the same unitary dosage form. Co-administration also; includes administering a first agent and a second agent, or more than two agents separately and as part of the same therapeutic regimen. The agents, if administered separately, need not necessarily be administered at essentially the same time, although they can be if so desired. Thus co-administration includes, for example, administering a first agent and a second agent as separate dosages or dosage forms, but at the same time. Co-administration also includes separate administration at different times and in any order.

The term "compound of the present invention," refers to any of the above-mentioned compounds, as well as those in the Examples that follow, and include those generically described or those described as species. The term also refers to pharmaceutically acceptable salts or solvates of these compounds.

The abbreviations used herein refer to the following:

| Abbreviation | Definition |
| --- | --- |
| AcOH | Acetic acid |
| Ar | Argon |
| BSA | Bovine serum albumin |
| DMF | Dimethylformamide |
| DNA | Deoxyribonucleic acid |
| EtOH | Ethyl alcohol, ethanol |
| g | Gram |
| HPLC | High pressure liquid chromatography |
| M | Molar |
| MeOH | Methyl alcohol, methanol |
| mg | Milligram |
| mp | Melting point |
| min | Minute |
| mL | Milliliter |
| mmol | Millimole |
| nM | Nanomolar |
| RNA | Ribonucleic acid |
| THF | Tetrahydrofuran |
| LDLR | Low density lipoprotein receptor |
| LDL | Low density lipoprotein |
| UM | micromolar |
| nM | nanomolar |

DETAILED DESCRIPTION

Figure 1:
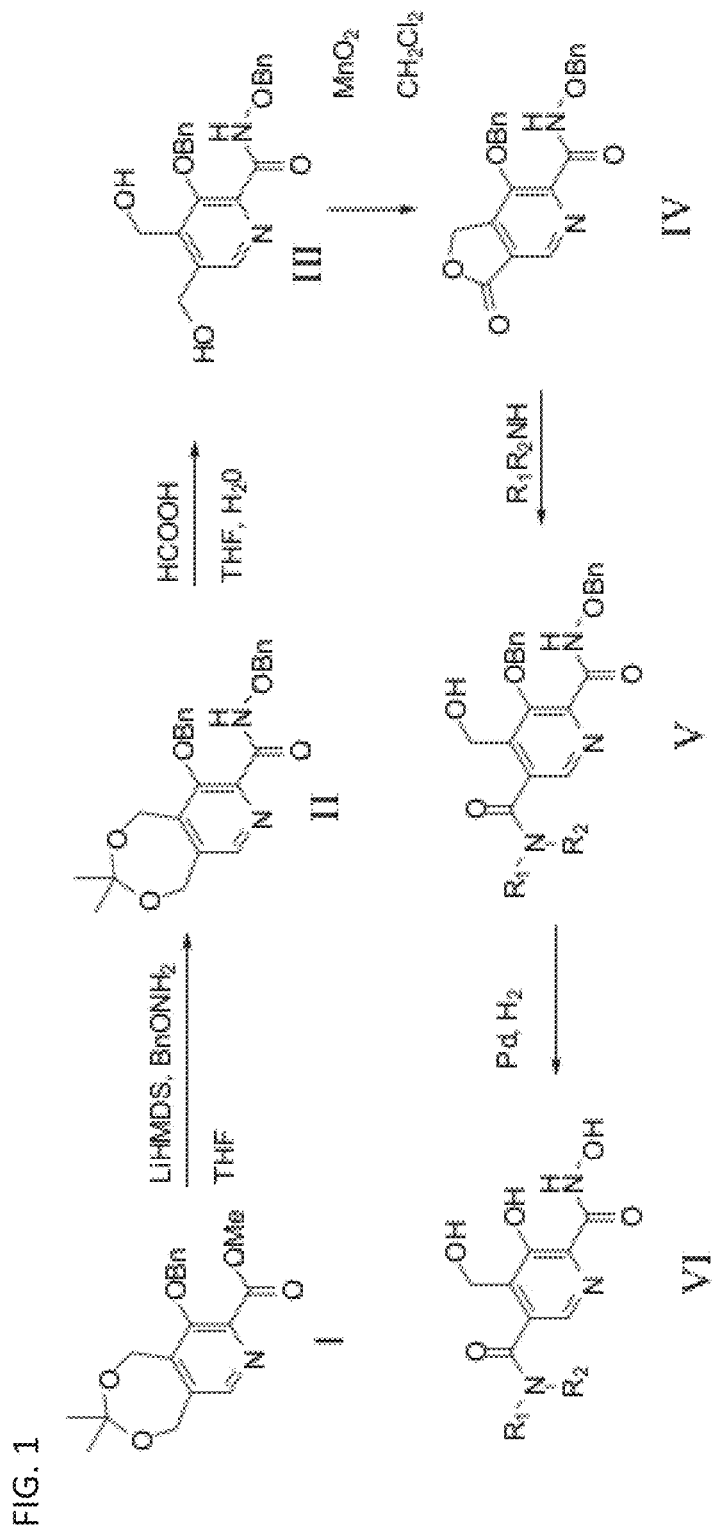
FIG. 1 is a synthetic scheme showing the synthesis of compound VI.

The present disclosure describes methods for lowering LDL-cholesterol level in a subject. The methods can include administering to the subject a LDL-lowering amount of a compound of Formula I. Further, methods are provided for inducing low density lipoprotein receptor (LDLR) expression in a cell, e.g., a cell in a tissue or an organ), and for modulating LDLR mRNA or protein expression and LDLR activity in a cell by administering compound of Formula I.

Screening of available compound libraries yielded potent inducers of low-density lipoprotein receptor (LDLR) in hepatic cells, selected from compounds described in U.S. Pat. No. 8,742,123 $B_2$.

Compounds

One aspect of the invention provides a compound having the Formula I, or a pharmaceutically acceptable salt thereof:

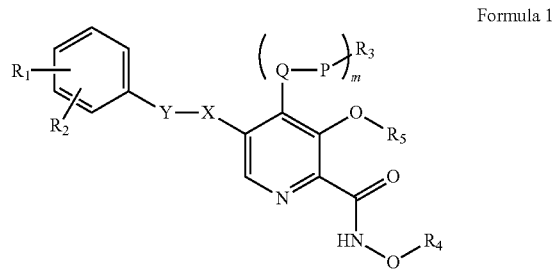

Formula 1

In some embodiments, Y—X is —C($R_7$)($R_{7a}$)N(R')C(O)—; —C($R_7$)($R_{7a}$)OC(O)—; —C($R_7$)($R_{7a}$)N(R')C($R_6$)($R_{6a}$)—; —C($R_7$)($R_{7a}$)S(O)$_2$C($R_6$)($R_{6a}$)—; —S(O)$_2$C($R_6$)($R_{6a}$)—; —C($R_7$)($R_{7a}$)C($R_6$)($R_{6a}$)—; —O—C($R_6$)($R_{6a}$)—; —N(R')C($R_6$)($R_{6a}$)—; or —C($R_7$)($R_{7a}$)OC($R_6$)($R_{6a}$)—. Each of $R_6$, $R_{6a}$, $R_7$, and $R_{7a}$, can be, independently, selected from H, $C_{1-6}$ alkyl, $C_{1-6}$ fluoroalkyl, benzyl, phenyl and heterocycle, R' can be selected from H, $C_{1-6}$ alkyl, benzyl, S(O)$_2$R", and C(O)R", and R" may be selected from $C_{1-6}$ alkyl, $C_{1-6}$ fluoroalkyl, benzyl, phenyl, and heterocycle;

In some embodiments, when Q is H, P and $R_3$ are absent. In other embodiments, when Q is $CH_3$, P and $R_3$ are absent. In some embodiments, Q is $CH_2$, or C(O).

In some embodiments, when P is H, $R_3$ is absent. In other embodiments, P is —O—, —N($R_8$)($R_{8a}$), or is absent, where the $R_8$ and $R_{8a}$ are selected independently from the group consisting of H, $C_{1-6}$ alkyl, $C_{1-6}$ fluoroalkyl, benzyl, phenyl, and heterocycle.

In some embodiments, $R_1$ is absent, $C_{1-6}$ alkyl, $C_1$-6 branched alkyl, $C_{1-6}$ alkene, halogen (F, Cl, Br, I), OH, —O—($C_{1-6}$ alkyl), —O—($C_{1-6}$ branched alkyl), —C(O) ($R_9$), —C(O)O($R_9$), —C(O)N($R_9$)($R_{9a}$), or —S(O)$_2$N($R_9$) ($R_{9a}$). $R_9$ and $R_{9a}$ can be selected independently from the group consisting of H, $C_{1-6}$ alkyl, $C_{1-6}$ fluoroalkyl, benzyl, phenyl and heterocycle.

In some embodiments, $R_2$ is absent, $C_{1-6}$ alkyl, $C_{1-6}$ branched alkyl, $C_{1-6}$ alkene, halogen (F, Cl, Br, I), OH, —O—($C_{1-6}$ alkyl), —O—($C_{1-6}$ branched alkyl), —C(O) ($R_{10}$), —C(O)O($R_{10}$), or —C(O)N($R_{10}$)($R_{10a}$). $R_{10}$ and $R_{10a}$ can be selected independently from the group consisting of H, $C_{1-6}$ alkyl, $C_{1-6}$ fluoroalkyl, benzyl, phenyl, and heterocycle, or $R_1$ and $R_2$ can be ortho substituents that together form a carbocyclic or heterocyclic ring system.

In some embodiments, $R_3$ is H, $C_{1-6}$ alkyl, $C_{1-6}$ fluoroalkyl, benzyl, phenyl, heterocycle, or is absent.

In some embodiments, $R_5$ is H, $C_{1-6}$ alkyl, $C_{1-6}$ fluoroalkyl, benzyl, phenyl, or heterocycle; or $R_3$ and $R_5$ combine to form a heterocyclic ring system.

In some embodiments, $R_4$ is H, $C_{1-6}$ alkyl, $C_{1-6}$ fluoroalkyl, benzyl, phenyl, or heterocycle.

In some embodiments, m is 0 or 1.

In some embodiments, Q is $CH_2$, P is —O—, $R_3$ is H, Y—X is —$CH_2NHCH_2$— or —$CH_2NHC(O)$—. In some embodiments, $R_1$ is selected from a halogen, —OH or —$OCH_3$, $R_2$ is absent or selected from —OH and a halogen. In some embodiments, $R_4$ is H or benzyl, and $R_5$ is H or benzyl, or a pharmaceutically acceptable salt or solvate thereof.

In some embodiments, Q is $CH_2$, P is —O—, $R_3$ is $CH_3$, Y—X is —$CH_2OCH_2$—. In some embodiments, $R_1$ is selected from a halogen, —OH or —$OCH_3$, $R_2$ is absent or selected from —OH and a halogen. In some embodiments, $R_4$ is H or benzyl, and $R_5$ is H or benzyl or a pharmaceutically acceptable salt or solvate thereof.

In some embodiments, the compound of Formula I is 5-[(4-fluoro-phenylamino)-methyl]-3-hydroxy-4-hydroxymethyl-pyridine-2-carboxylic acid hydroxyamide. In some embodiments, the compound of Formula I is 5-(4-fluoro-phenoxymethyl)-3-hydroxy-4-hydroxymethyl-pyridine-2-carboxylic acid hydroxyamide. In some embodiments, the compound of Formula I is 5-[2-(4-fluoro-phenyl)-ethyl]-3-hydroxy-4-hydroxymethyl-pyridine-2-carboxylic acid hydroxyamide.

Pharmaceutical Compositions

Pharmaceutical compositions contemplated herein include at least one compound of the present invention, and pharmaceutically acceptable salts, solvate or formulation thereof, with a pharmaceutically acceptable carrier, adjuvant, or vehicle. Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethyleneglycol, sodium carboxymethylcellulose, polyacrylates, waxes, polyethylene-polyoxypropylene-block polymers, polyethylene glycol, liposomes, and wool fat.

Compounds of the present invention that are basic may be prepared as a salt using suitable methods known in the art, including treatment of the free base with an inorganic acid, such as hydrochloric acid; hydrobromic acid; sulfuric acid; nitric acid; phosphoric acid; and the like, or with an organic acid, such as acetic acid; maleic acid; succinic acid; mandelic acid; fumaric acid; malonic acid; pyruvic acid; oxalic acid; glycolic acid; salicylic acid; pyranosidyl acid, such as glucuronic acid or galacturonic acid; alpha-hydroxy acid, such as citric acid or tartaric acid; amino acid, such as aspartic acid or glutamic acid; aromatic acid, such as benzoic acid or cinnamic acid; sulfonic acid, such as p-toluenesulfonic acid or methanesulfonic acid, and the like.

It is understood by those skilled in the art that the compounds of the present invention, salts, or solvates thereof may exist in different crystal or polymorphic forms that are within the scope of the present invention and specified formulas.

Basic compounds of the present invention can form a variety of salts with various inorganic and organic acids. Although such salts must be pharmaceutically acceptable for administration to animals, it is common practice to first isolate the compound of the present invention as a pharmaceutically unacceptable salt and then convert to a free base compound by treatment with an alkaline reagent and subsequently convert the latter free base to a pharmaceutically acceptable acid addition salt. The acid addition salts of the base compounds of this invention can be prepared by treating the base compound with a substantially equivalent amount of the selected mineral or organic acid in an aqueous solvent medium or in a suitable organic solvent, such as methanol or ethanol.

Compounds of the present invention that are acidic may be prepared as a salt using suitable methods known in the art, including treatment of the free acid with an inorganic or organic base, such as an amine (primary, secondary, or tertiary); an alkali metal or alkaline earth metal hydroxide; or the like. Examples of suitable salts include organic salts derived from amino acids such as glycine and arginine; ammonia; primary, secondary, and tertiary amines; and cyclic amines, such as piperidine, morpholine, and piperazine; as well as inorganic salts derived from sodium, calcium, potassium, magnesium, manganese, iron, copper, zinc, aluminum, and lithium.

Acidic compounds of the present invention can form base salts with various pharmacologically acceptable cations. Examples of such salts include the alkali metal or alkaline-earth metal salts and particularly, the sodium and potassium salts, which can be prepared using conventional techniques. The chemical bases suitable as reagents in preparing the pharmaceutically acceptable base salts of this invention are those which form non-toxic base salts with the acidic compounds of the present invention. Such non-toxic base salts include those derived from such pharmacologically acceptable cations as sodium, potassium, calcium, and magnesium, etc. These salts can be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yield of the desired final product.

To treat or prevent diseases or conditions caused or mediated by elevated cholesterol, a pharmaceutical composition, including at least one of the compounds of the present invention, is administered in a pharmaceutically acceptable formulation prepared by combining a therapeutically effective amount of the compound with one or more pharmaceutically suitable carriers including diluents, excipients and auxiliaries that facilitate processing of the active compounds into a pharmaceutically acceptable formulation. Carriers employed may be either solid or liquid. Exemplary solid carriers are lactose, sucrose, talc, gelatin, agar, pectin, acacia, magnesium stearate, stearic acid, and the like. Exemplary liquid carriers are syrup, peanut oil, olive oil, water, and the like. Similarly, the inventive compositions may include time-delay or time-release material known in the art, such as glyceryl monostearate or glyceryl distearate alone or with a wax, ethylcellulose, hydroxypropylmethylcellulose, methylmethacrylate or the like. Further additives or excipients may be added to achieve the desired formulation properties. For example, a bioavailability enhancer, such: as Labrasol® (a nonionic oil-in-water surfactant), Gelucire® (a nonionic water-dispersible surfactant), or the like, or formulator, such as CHIC (carboxy-methylcellulose), PG (propyleneglycol), or PEG (polyethyleneglycol), may be added. Gelucire®, a semi-solid vehicle that protects active ingredients from light, moisture and oxidation, may be added, e.g., when preparing a capsule formulation.

If a solid carrier is used, the preparation can be tableted, placed in a hard gelatin capsule in powder or pellet form, or formed into a troche or lozenge. The amount of solid carrier may vary, but generally will be from about 25 mg to about 1 g. If a liquid carrier is used, the preparation may be in the form of syrup, emulsion, soft gelatin capsule, sterile injectable solution or suspension in an ampoule or vial or non-aqueous liquid suspension. The inventive compositions are prepared in unit-dosage form appropriate for the mode of administration, e.g., parenteral or oral administration.

To obtain a stable water-soluble dose form, a pharmaceutically acceptable salt of a compound of the present invention may be dissolved in an aqueous solution of an organic or inorganic acid, such as 0.3 M solution of succinic acid or citric acid. If a soluble salt form is not available, the agent may be dissolved in a suitable co-solvent or combinations of co-solvents. Examples of suitable co-solvents include alcohol, propylene glycol, polyethylene glycol 300, polysorbate 80, glycerin, and the like, in concentrations ranging from 0-60% of the total volume. In an exemplary embodiment, a compound of the present invention is dissolved in DMSO and diluted with water. The composition may also be in the form of a solution of a salt form of the active ingredient in an appropriate aqueous vehicle such as water or isotonic saline or dextrose solution.

Pharmaceutical preparations for oral use can be obtained using a solid excipient in an admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

The pharmaceutical compositions, including the compounds of the present invention may also contain suitable solid- or gel-phase carriers, or excipients. These carriers and excipients may provide marked improvement in the bioavailability of poorly soluble drugs. Examples of such carriers or excipients include calcium carbonate, calcium, phosphate, sugars, starches, cellulose derivatives, gelatin, and polymers such as polyethylene glycols. Furthermore, additives or excipients such as Gelucire® (a nonionic water-dispersible surfactant), Capryol® (a nonionic water-insoluble surfactant), Labrafil® (a nonionic water-dispersible surfactant), Labrasol® (a nonionic oil-in-water surfactant), Lauroglycol® (a nonionic water-insoluble surfactant), Plurol® (a nonionic water-in-oil emulsifier), Peceol® (an oily liquid vehicle), Transcutol® (a high-purity solvent), and the like, may be used. Further, the pharmaceutical composition may be incorporated into a skin patch for delivery of the drug directly onto the skin.

The compounds of this invention may be modified by appending appropriate functionalities to enhance selective biological properties. Such modifications are known in the art and include those which increase biological penetration into a given biological system (e.g., blood, lymphatic system, central nervous system), increase oral bioavailability, increase solubility to allow administration by injection, alter metabolism or alter rate of excretion (Pharmacokinetic Optimization in Drug Research, Testa, B. et al, 2001, Wiley-VCH, VCHA).

The pharmaceutical compositions of this invention may be administered orally, parenterally, by inhalation spray, topically, rectally, nasally, buccally, vaginally, or via an implanted reservoir and are preferably administered orally or parenterally. The pharmaceutical compositions of this invention may contain any conventional non-toxic pharmaceutically acceptable carriers, adjuvants or vehicles. The term "parenteral" or "parenterally" as used herein includes subcutaneous, intracutaneous, intravenous, intramuscular, intraarticular, intrasynovial, intrasternal, intrathecal, intralesional, and intracranial injection or infusion techniques.

Pharmaceutical compositions of the invention may be in the form of a sterile injectable preparation, for example, as a sterile injectable aqueous or oleaginous suspension. This suspension may be formulated according to techniques known in the art using suitable dispersing or wetting agents (for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solutions. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions.

Pharmaceutical compositions of the invention may be orally administered in any orally acceptable dosage form including, but not limited to, capsules, tablets, and aqueous suspension and solutions. In the case of tablets for oral and carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

Pharmaceutical compositions of the invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax, and polyethylene glycols.

The pharmaceutical compositions of this invention may be administered by nasal aerosol or inhalation. Such compositions are prepared according to techniques well known in the art of pharmaceutical formulation and may be prepared as solutions in saline employing benzyl alcohol or other suitable preservatives, absorption promoters to enhance bioavailability, fluorocarbons, and/or other solubilizing or dispersing agents known in the art.

Dosages

It will be appreciated that the actual dosages of the agents of this invention will vary according to the particular agent being used, the particular composition formulated, the mode of administration, and the particular site, host, and disease being treated. Those skilled in the art using: conventional dosage determination tests in view of the experimental data for a given compound may ascertain optimal dosages for a given set of conditions. For oral administration, an exemplary daily dose generally employed will be from about 0.001 to about 1000 mg/kg of body weight, with courses of treatment repeated at appropriate intervals, preferably between 0.01 and about 25 mg/kg body weight per day, and more preferably between about 0.5 and about 25 mg/kg body weight per day of the active ingredient compound are useful in the prevention and treatment of elevated cholesterol, including high circulating LDL.

Furthermore, the pharmaceutically acceptable formulations of the present invention may contain a compound of the present invention, or a pharmaceutically acceptable salt or solvate thereof, in an amount of about 10 mg to about 2000 mg, or from about 10 mg to about 1500 mg, or from about 10 mg to about 1000 mg, or from about 10 mg to about 750 mg, or from about 10 mg to about 500 mg, or from about 25 mg to about 500 mg, or from about 50 to about 500 mg, or from about 100 mg to about 500 mg. Additionally, the pharmaceutically acceptable formulations of the present invention may contain a compound of the present invention, or a pharmaceutically acceptable salt or solvate thereof, in an amount from about 0.5 w/w % to about 95 w/w %, or from about 1 w/w % to about 95 w/w %, or from about 1 w/w % to about 75 w/w %, or from about 5 w/w % to about 75 w/w %, or from about 10 w/w % to about 75 w/w %, or from about 10 w/w % to about 50 w/w %.

Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the patient treated and the particular mode of administration. A typical preparation will contain from about 5% to about 75% active compound (w/w). Preferably, such preparations contain from about 20% to about 50% active compound.

Upon improvement of a patient's condition, a maintenance dose of a compound, composition or combination of this invention may be administered if necessary. Subsequently, the dosage or frequency of administration, or both, may be reduced, as a function of the symptoms, to a level at which the improved condition is retained. When the symptoms have been alleviated to the desired level, treatment should cease, at least in principle. Patients may, however, require intermittent treatment on a long-term basis, upon any recurrence of disease symptoms, especially for high elevations of cholesterol.

As the skilled artisan will appreciate, precision medicine, lower or higher doses than those recited above may be required. Specific dosage and treatment regimen for any particular patient will depend upon a variety of factors, including the genetic background, activity of the specific compound employed, the age, body weight, general health status, sex, diet, time of administration, rate of excretion, drug combination, the severity and course of the infection, the patient's disposition to the infection and the judgment of the treating physician.

With respect to the compounds of the present invention, the particular pharmaceutical formulation, the dosage, and the number of doses given per day to a mammal requiring such treatment, are all choices within the knowledge of one of ordinary skill in the art and can be determined without undue experimentation.

Treatment

The compounds of this invention are also useful as commercial reagents which effectively lower circulating cholesterol. As commercial reagent, the compounds of this invention, and their derivatives, may be derivatized to bind to a stable resin as a tethered substrate for affinity chromatography applications. These and other uses which characterize commercial cholesterol reducing agents will be evident to those of ordinary skill in the art.

The compounds of the present invention can be used alone (i.e., monotherapy) or administered in combination with one or more other cholesterol reducing agents, in the treatment of, for example, atherosclerosis (lipid-associated cardiovascular disorders, e.g., U.S. Pat. No. 4,891,220), hypercholesterolemia (lipid-associated cardiovascular disorder, e.g., U.S. Pat. No. 4,891,220), hypertriglyceridemia (a high level of triglycerides in the blood, e.g., U.S. Pat. No. 8,293,727), diabetic complications (include, for example, diabetic retinopathy, nephropathy, and neuropathy, resulting from abnormalities in microvascular function, e.g., U.S. Pat. No. 5,281,619), dyslipidemia (an abnormally elevated cholesterol or lipids in the blood, e.g., U.S. Pat. No. 6,630,450), hyperlipidemia (lipid-associated cardiovascular disorder, e.g., U.S. Pat. No. 4,891,220), hypoalphalipoproteinemia (a high-density lipoprotein deficiency, e.g., U.S. Pat. No. 6,147,089), metabolic syndrome (obesity associated with hypertension, glucose intolerance, atherosclerosis, and dyslipidemia, e.g., U.S. 2006/0211020), stroke (damage to the brain from interruption of its blood supply, e.g., U.S. Pat. No. 5,385,940), vascular dementia (brain damage caused by multiple strokes, e.g., U.S. Pat. No. 6,458,807), chronic kidney disease (longstanding disease of the kidneys leading to renal failure, e.g., U.S. 2009/0081713), coronary heart disease (damage or disease in the heart's major blood vessels, e.g., U.S. Pat. No. 6,242,186), coronary artery disease (damage or disease in the heart's major blood vessels, e.g., U.S. Pat. No. 5,036,857), retinopathy (a complication of diabetes that affects the eyes, e.g., U.S. Pat. No. 5,019,591), inflammation (a response triggered by damage to living tissues, e.g., U.S. Pat. No. 6,136,839), thrombosis (formation of a blood clot inside a blood vessel, obstructing the flow of blood through the circulatory system, e.g., U.S. Pat. No. 4,880,788), peripheral vascular disease (a circulatory condition in which narrowed blood vessels reduce blood flow to the limbs, e.g., U.S. Pat. No. 8,143,316), or congestive heart failure (heart's inability to pump blood sufficiently to maintain blood flow to meet the body's needs, e.g., U.S. Pat. No. 5,935,924) in a mammal.

The compounds of this invention may be administered in combination with cholesterol reducing agents which target other steps in the cholesterol metabolism. These agents are, for example, a lipase inhibitor (a substance used to reduce the activity of lipases found in the intestine, e.g., orlistat, e.g., U.S. Pat. No. 6,558,690), a 3-hydroxy-3-methyl-glutaryl-coenzyme A (HMG CoA) reductase inhibitor (a statin that facilitates the prevention of cardiovascular disease by lowering low-density lipoprotein cholesterol, e.g., atorvastatin, fluvastatin, lovastatin; e.g., Hong et al. Healthc. Inform. Res. 2017, 3, 199), a HMG CoA synthase inhibitor (inhibits the HMG-CoA synthase enzyme that is an intermediate in cholesterol synthesis and ketogenesis, e.g., Skaff et al. Biochemistry 2012, 51, 4713), a cholesteryl ester transfer protein (CETP) inhibitor (inhibits the promotion of the transfer of cholesteryl esters from HDL to very low-density lipoprotein and LDL, e.g., anacetrapib, evacetrapib, dalcetrapib; e.g., Kosmas et al. Clin. Med. Insights Cardiol. 2016; 10, 37), a bile acid absorption inhibitor (reduces low density lipoprotein (LDL) cholesterol levels, e.g., cholestyramine, colestipol, colesevelam; e.g., Kramer et at. Curr. Med. Chem. 2006, 13, 997), a cholesterol absorption inhibitor (prevents the uptake of cholesterol from the small intestine into the circulatory system, e.g., ezetimibe; e.g., Dujovne et al. Am. J. Cardiol. 2002, 90, 1092), a cholesterol synthesis inhibitor (HMG-CoA reductase inhibitors, e.g., statins; e.g., Endo Atheroscler. Suppl. 2004, 3, 67), a squalene synthase inhibitor (decreases cholesterol synthesis and plasma triglyceride levels, e.g., zaragozic acids, 2,8-dioxabicyclo[3.2.1]octane derivatives; e.g., Kourounakis et al. Curr. Med. Chem. 2011, 18, 4418), a squalene epoxidase (enzyme that oxidizes squalene to squalene epoxide; e.g., Ryder et al. Biochem.

J. 1985, 230, 765) or cyclase inhibitor (an enzyme that has a diverse role in cell regulation and activity; e.g., Wang et al. Sci. Transl. Med. 2011, 3, 65ra3) or a microsomal triglyceride transfer protein (MTP) inhibitor or Apolipoprotein B (ApoB) secretion inhibitor, or a combination of both (inhibits lipoprotein assembly; e.g., Hussain et al. J. Lipid Res. 2003, 44, 22), a fibrate (a hypolipidemic agent, e.g., choline fenofibrate; e.g., Shepherd Postgrad. Med. J. 1993, 69, S34), niacin (lipid-lowering medication, e.g., Canner et al. J. Am. Col. Cardiol. 1986, 8, 1245) alone or in combination with lovastatin (a statin that treats high cholesterol and triglyceride levels; e.g., Downs et al. JAMA 1998, 279, 1615), an ion-exchange resin (e.g., colestyramine, is a bile acid sequestrant; e.g., Hashim et al. JAMA 1965, 192, 289), an antioxidant (used to reducing the levels of LDL cholesterol; e.g., Anderson et al. N. Engl J. Med. 1995, 332, 488), an acyl-coenzyme A: cholesterol acyltransferase (ACAT) inhibitor (inhibits an intracellular enzyme that catalyzes the formation of cholesterol esters from cholesterol and fatty acyl-coenzyme; e.g., Chang et al. Am. J. Physiol. Endocrinol. Metab. 2009, 297, E1) and a bile acid sequestrant (polymeric resin that serve as ion-exchange resins used to bind components of bile in the gastrointestinal tract, e.g., colestipol; e.g., Ast et al. Clin. Pharmacol. 1990, 30, 99), an HMG-CoA reductase gene expression inhibitor, an HMG-CoA synthase gene expression inhibitor (SREBP2 inhibitors would strongly decrease gene expression of HMG-CoA reductase and synthase; Pandyra et al. Oncotarget. 2015, 6(29): 26909-26921; Pandyra et al. Cancer Res. 2014, 74(17): 4772-82; statins are HMG-CoA reductase inhibitors and, therefore, increase HMG-CoA reductase and synthase gene expression by a feedback mechanism (mediated by the transcription factor SREBP-2) but their major actions are via upregulation of LDLR mRNA (also by SREBP-2); a list of the suitable drugs for combination are listed in Table 1) or a proprotein convertase subtilisin kexin type 9 (PCSK9) inhibitor (decreases LDL blood levels, e.g., alirocumab, evolocumab; e.g., N. Engl. J. Med. 2015, 373, 1588) or combination with other lipid-lowering drugs such as inhibitors of APOCIII, ANGPTL3, ANGPTL4, which increase lipoprotein lipase activity, gemecabene (Gemphire) or bempedoic acid (Esperio).

Combination therapies according to this invention exert an additive or combined effect on elevated cholesterol reduction because each therapeutic agent of the combination acts on a different site of cholesterol metabolism. The use of such combination therapies also advantageously enables a reduction in the dosage of each elevated cholesterol reducing agent, compared to administration of either agent alone as a monotherapy, while providing an equivalent or better therapeutic or prophylactic effect. Administration of lower doses of each therapeutic agent often reduces or even eliminates side effects or toxicity relative to monotherapy. Further, combination therapies reduce the potential for the development of undesired side effects to the agents administered compared to monotherapy.

Administration of the compounds of this invention in combination therapies with other agents to patients may be sequential or concurrent. Further, pharmaceutical or prophylactic compositions of this invention may include a combination of cholesterol reducing agent of this invention and another therapeutic or prophylactic agent. Additional examples of agents useful for treating elevated cholesterol and suitable for combination therapies with the compounds of this invention are listed in Table 1.

TABLE 1

| Drug Type | Generic Name (brand name) | Indication |
| --- | --- | --- |
| De novo cholesterol synthesis inhibitors (statins or HMG-CoA reductase inhibitors) | Atorvastatin (Lipitor ®), Fluvastatin (Lescol ®, Lescol XL), Lovastatin (Mevacor ®, Altropev), Pravastatin (Pravachol ®), Rosuvastatin (Crestor ®), Simvastatin (Zocor ®), Pitavastatin (Livalo ®) | For Management as an adjunct to diet to reduce elevated total-C, LDL-C, apo B and TG levels in patients with primary hypercholesterolemia and mixed dyslipidemia. For primary prevention of coronary heart disease and to slow progression of coronary atherosclerosis in patients with coronary heart disease. |

TABLE 1-continued

| Drug Type | Generic Name (brand name) | Indication |
|---|---|---|
| Inhibitors of intestinal cholesterol absorption (NPC1L1 inhibitors) | Ezetimibe (Zetia ®), Ezetimibe + simvastatin (Vytorin ®) | For use as adjunctive therapy to diet for the reduction of elevated total-C, LDL-C, and Apo B in patients with primary (heterozygous familial and non-familial) hypercholesterolemia |
| PPAR agonists (Fibrates) | Gemfibrozil (Lopid ®), Fenifibrate (Antara ®, Lofibra ®, Tricor ®), Clofibrate (Atromid ®) | For the treatment of primary hyperlipidaemia types IIa, IIb, III, IV, and V (Fredrickson classification) corresponding to groups I, II, and III of the European Atherosclerosis Society guidelines - when diet alone or improvements in lifestyle such as increases exercise or weight reduction do not lead to an adequate response. Also for the treatment of secondary hyperlipidaemias, e.g. severe hypertriglyceridemias, when sufficient improvement does not occur after correction of the underlying disorder (e.g. diabetes mellitus) |
| Bile sequestrants (resins) | Cholestyramine (Questran ®, Prevalite ®), Colestipol (Colestid ®, Flavored Colestid), Colesevelam (Welchol ®) | Indicated as adjunctive therapy to diet for the reduction of elevated serum cholesterol in patients with primary hypercholesterolemia (elevated low density lipoprotein [LDL] cholesterol) who do not respond adequately to diet. Also for the relief of pruritus associated with partial biliary obstruction. |
| PCSK9 inhibitors MTP inhibitors | 1) Monoclonal antibodies: Alirocumab (Praluent ®), Evolocumab (Repatha ®) 2) Gene silencers: ALN-PCSsc (Inclisiran) 3) Vaccines: AT04A Lomitapide (Juxtapid ®) | Indicated as an adjunct to diet and maximally tolerated statin therapy in adults who require additional LDL-cholesterol (LDL-C) lowering due to heterozygous familial hypercholesterolemia or clinical atherosclerotic cardiovascular disease. Used in homozygous familial hypercholesterolemia (HoFH) patients to reduce low-density lipoprotein cholesterol (LDL-C), total cholesterol (TC), apolipoprotein B (apo B), and non-high-density lipoprotein cholesterol (non-HDL-C). |
| ApoB antisense oligonucleotides | Mipomersen (Kynamro ®) | Used in patients with homozygous familial hypercholesterolemia as an adjunct to diet and other lipid-lowering medications. |

Compounds of the present invention may be administered in combination with an additional agent or pharmaceutical composition that increases the bioavailability or slows the metabolism of the compounds. Agents or pharmaceutical compositions that may increase the bioavailability or slow the metabolism of the compounds herein include inhibitors of at least one isoform of the cytochrome P450 (CYP450) enzymes, preferably CYP1A2, CYP2d6, CYP2C$_9$, CYP2C$_{19}$ and CYP3A4. Suitable agents that may be used to inhibit CYP3A4 include, but are not limited to, nefidipine and ritonavir. Such combinations may be administered such that a compound or compounds of the present invention are present in a single formulation or in the form of separate formulations that may be administered sequentially with an appropriate period of time in between or simultaneously. The choice of whether to include the compound or compounds of the present invention in the same formulation as the additional agent or agents is within the knowledge of one of ordinary skill in the art.

Preparation of Intermediates and Compounds

In some embodiments, the first approach (FIG. 1) starts from pyridoxine which is modified to produce Intermediate I using methodologies described in Paul et al. (J. Med. Chem. 1977, 20, 745). Intermediate I may be modified to produce a protected hydroxamic acid (II) by ester displacement. The isopropylidene protecting group of II may be removed by mild hydrolysis with formic acid to give intermediate III. Selective oxidation of the 5-CH$_2$OH group of III ca be performed using manganese dioxide (MnO$_2$) and III can spontaneously cyclize to the corresponding lactone intermediate (IV). In some embodiments, IV is substituted with an amine, producing the corresponding amide V. Protecting groups can be removed using hydrogenolysis giving the desired product VI.

In some embodiments, the second approach (FIG. 2) commences with intermediate VIII. VIII can be obtained from Intermediate I, using steps 2 and 3 of FIG. 1: removal of the isopropylidene protecting group by hydrolysis (as step 2 of FIG. 1), followed by selective oxidation of 5-CH$_2$OH with MnO$_2$ (as step 3 of FIG. 1). VIII may be then hydrolyzed using potassium trimethylsilanoate to generate intermediate VII. VII may be transformed to intermediate IV using O-protected hydroxylamine and aryl sulfonyl halide. In some embodiments, VI is substituted with an amine, producing the corresponding amide V. The protecting groups can be removed by hydrogenolysis (VI). In some embodiments, further hydrogenation yields the desired product IX.

Figure 2:
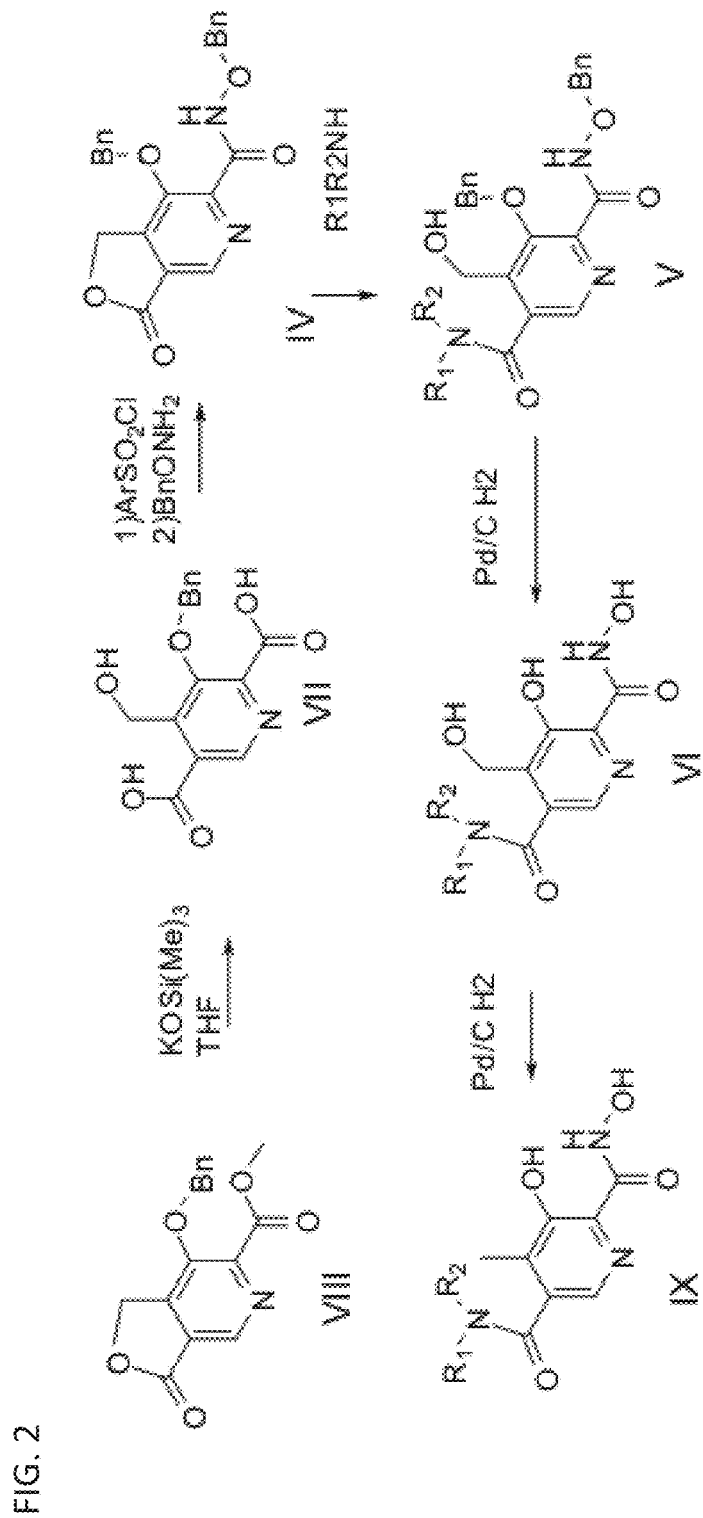
FIG. 2 is a synthetic scheme showing the synthesis of compound IX.
Figure 3:
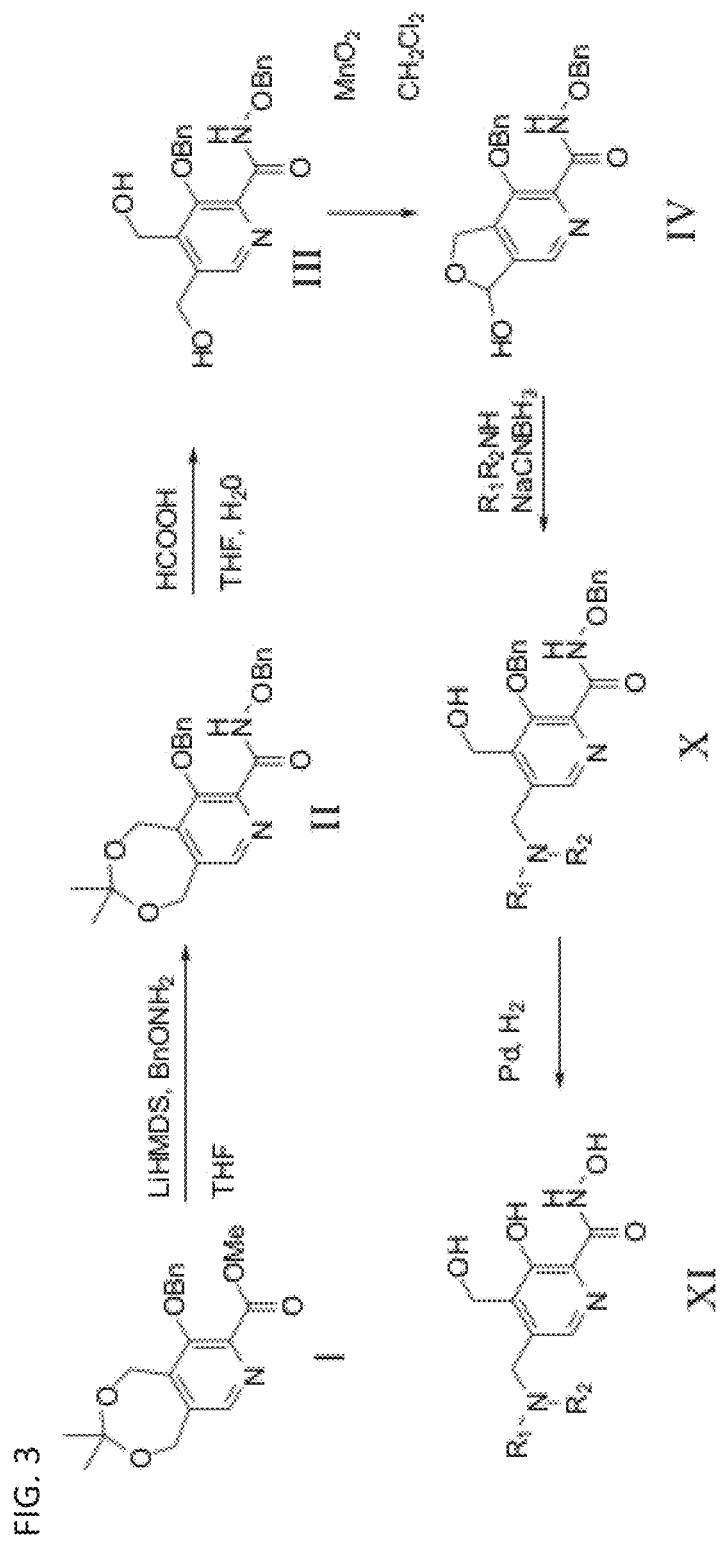
FIG. 3 is a synthetic scheme showing the synthesis of compound XI.

In some embodiments, the third approach (FIG. 3) starts with the protected pyro as in FIG. 1 and generates lactol IV by controlled oxidation with MnO$_2$. The lactol IV can be readily converted to the amine X through reductive amination and further reduction by catalytic hydrogenation generating compound XI.

In some embodiments, the fourth approach (FIG. 4) starts from pyridoxine and generates intermediate XIII in a manner similar to that described in Adamczyk M. et al. (Tetrahedron 2000, 56, 2379). XIII can then be oxidized selectively at the 2 methyl group through an N-oxide intermediate XIV followed by rearrangement to the alcohol XV. Further stepwise oxidation can yield an aldehyde XVI, followed by an ester XVII. In some embodiments, hydrolysis of the isopropylidene of XVII and displacement of the ester XVIII with hydroxylamine yields the desired product compound XIX.

Figure 4:
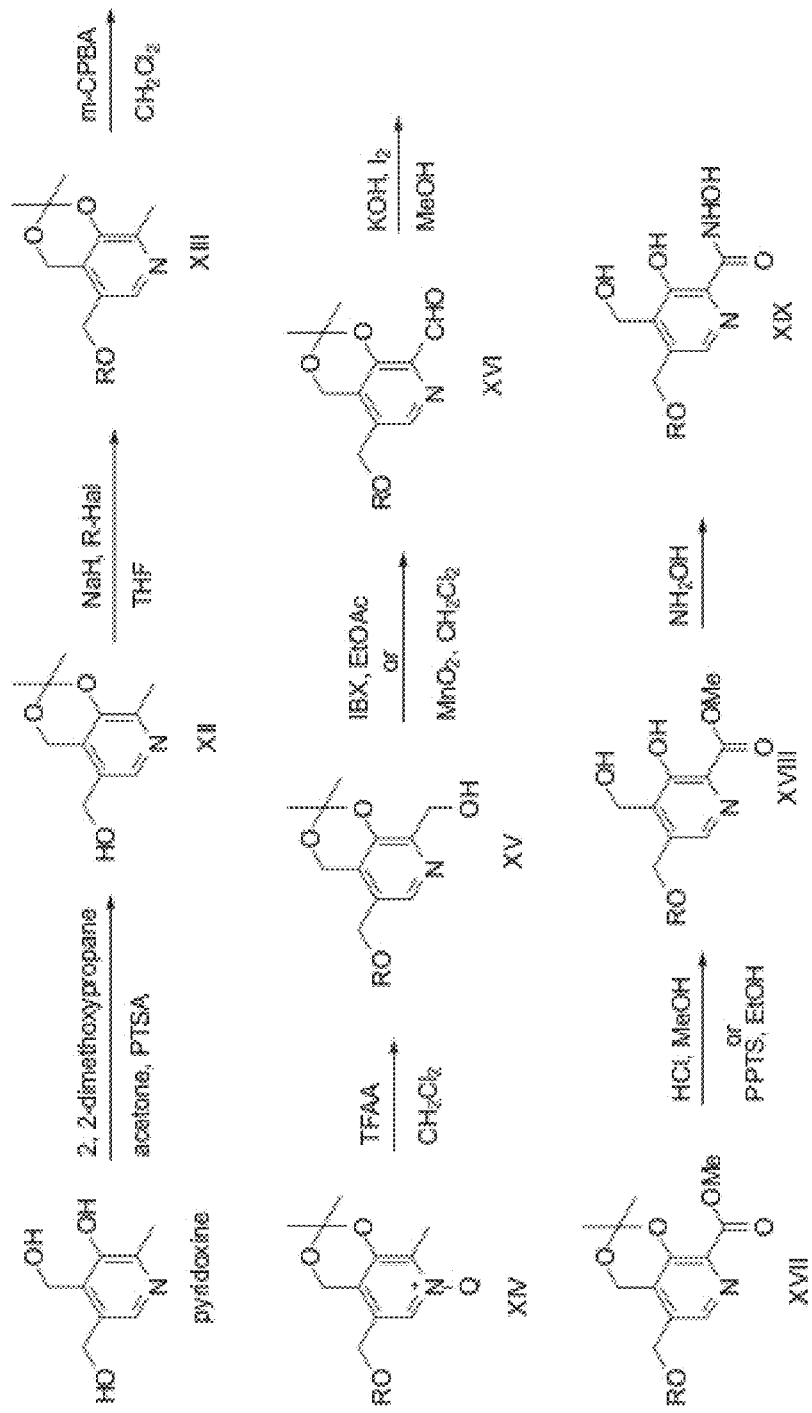
FIG. 4 is a synthetic scheme showing the synthesis of compound XIX.

In some embodiments, the fifth approach (FIG. 5), for synthesis of DENV RdRp inhibitor compounds of invention, starts from the intermediate XVII of FIG. 4. XVII can be hydrolyzed to the acid XX and XX is subsequently coupled to O-benzylhydroxylamine to give XXI. XXI may be subjected to hydrogenation, yielding the product compound XXIII, or to hydrolysis, yielding the product compound XXII.

Figure 6:
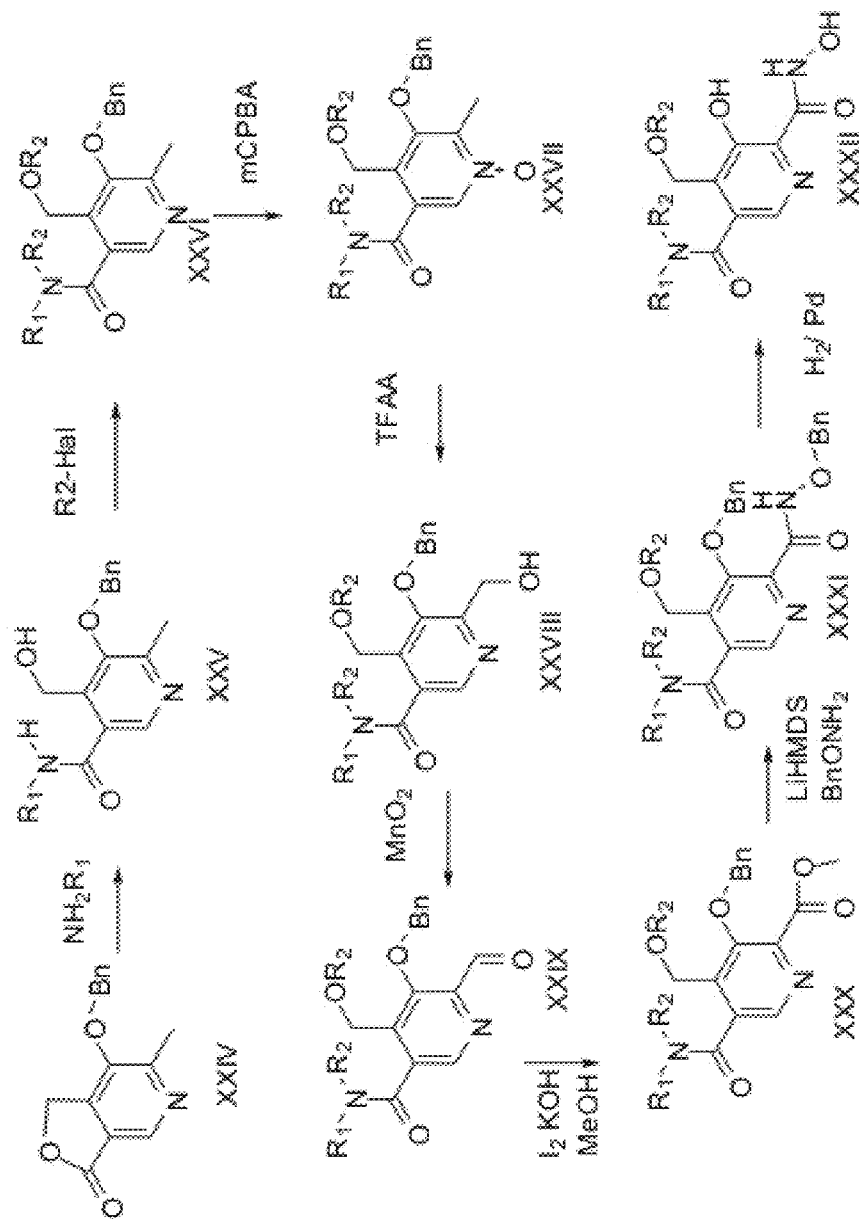
FIG. 6 is a synthetic scheme showing the synthesis of compound XXXII.

In some embodiments, the sixth approach (FIG. 6) begins from 7-(benzyloxy)-6-methylfuro[3,4-c]pyridin-3(1H)-one, intermediate XXIV (Paul, B. et al. J. Het. Chem., 1976, 13, 701). XXIV can be reacted with an amine yielding intermediate XXV. XXV may then be alkylated to XXVI and oxidized selectively at the 2 position through an N-oxide rearrangement, as described in FIG. 4, to yield intermediate XXX. XXX may then be displaced and hydrogenated to yield the desired product compound XXXII.

Figure 5:
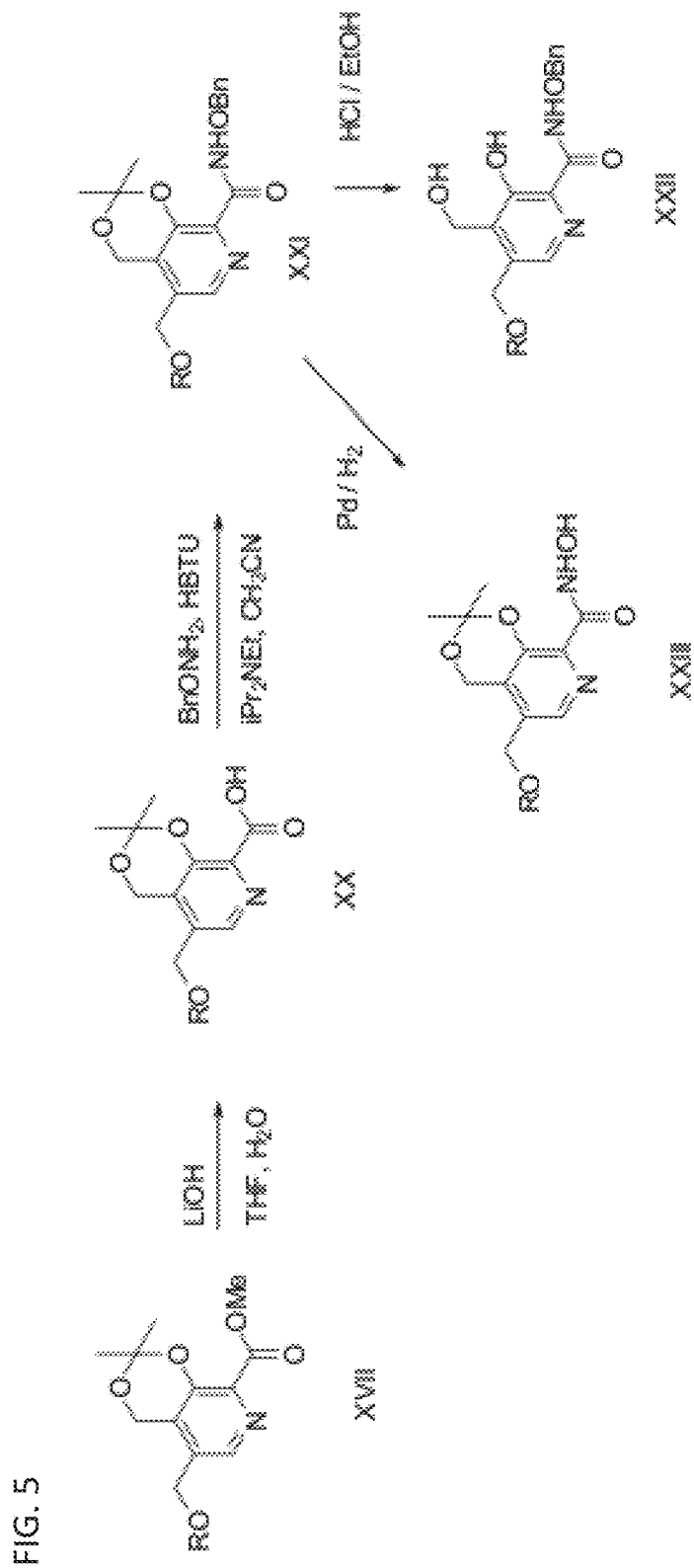
FIG. 5 is a synthetic scheme showing the synthesis of compounds XXII and XXIII.
Figure 7:
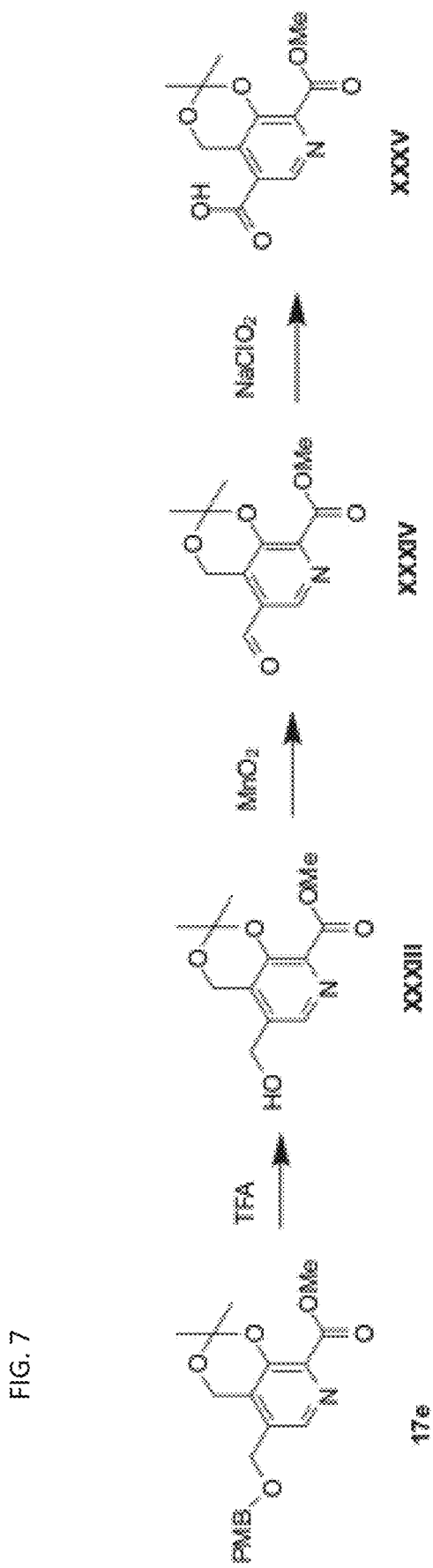
FIG. 7 is a synthetic scheme showing the synthesis of compound XXXV.

In some embodiments, the seventh approach (FIG. 7) begins from an analogue of compound XVII of FIG. 5. 17e may be acidified in anhydrous conditions to yield product XXXIII. This product can be oxidized to give the intermediate aldehyde XXXIV and further oxidized, under controlled conditions, to give the carboxylic acid intermediate XXXV.

Figure 8:
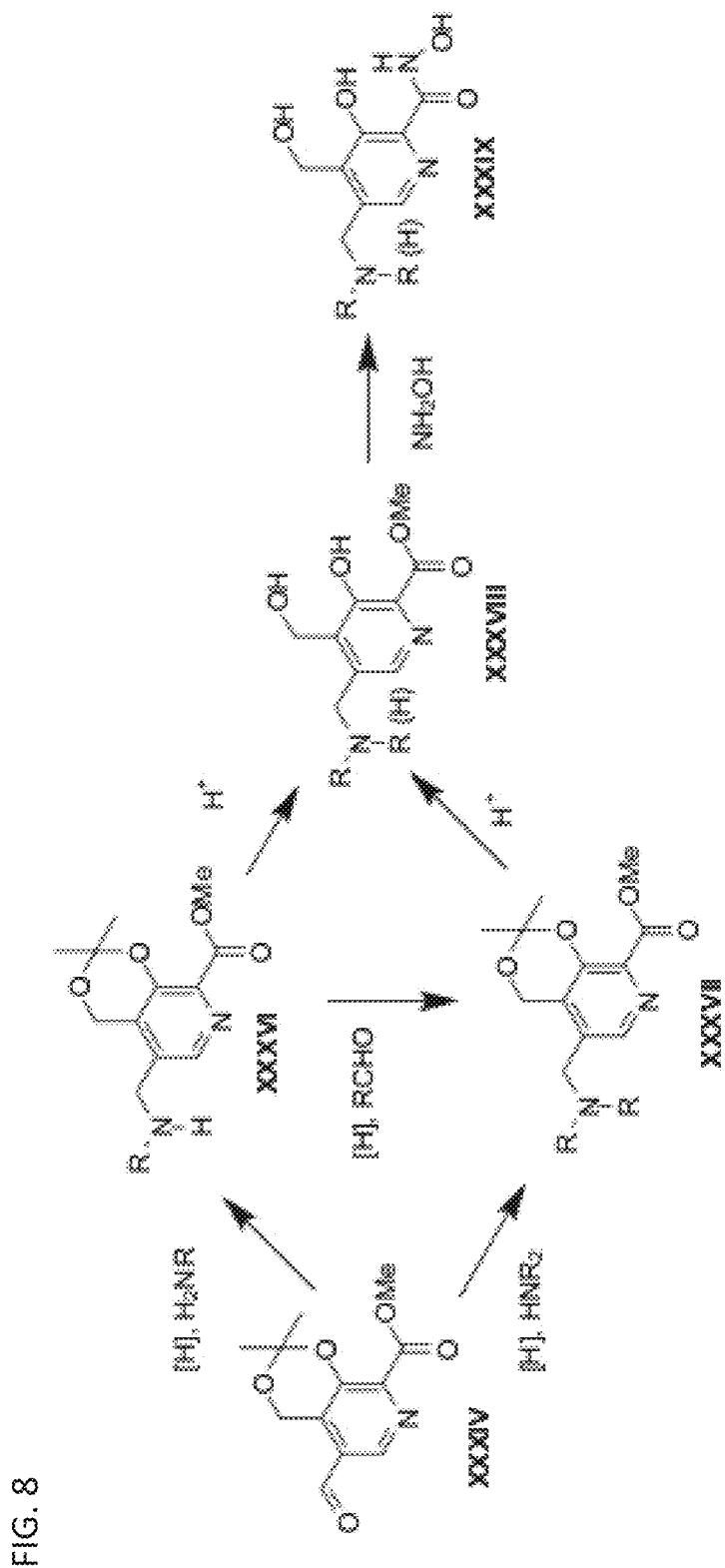
FIG. 8 is a synthetic scheme showing the synthesis of compound XXXIX.

In some embodiments, the eighth approach (FIG. 8) consists of reductive amination of intermediate XXXIV with either a primary or secondary amines to obtain XXXVI or XXXVII respectively. XXXVII analogues may be obtained by another reductive amination of aldehydes with XXXVI. Treatment of XXXVI and XXXVII analogues with aqueous acids can yield the intermediate XXXVIII, which can be further reacted with hydroxylamine solutions to give product XXXIX.

Figure 9:
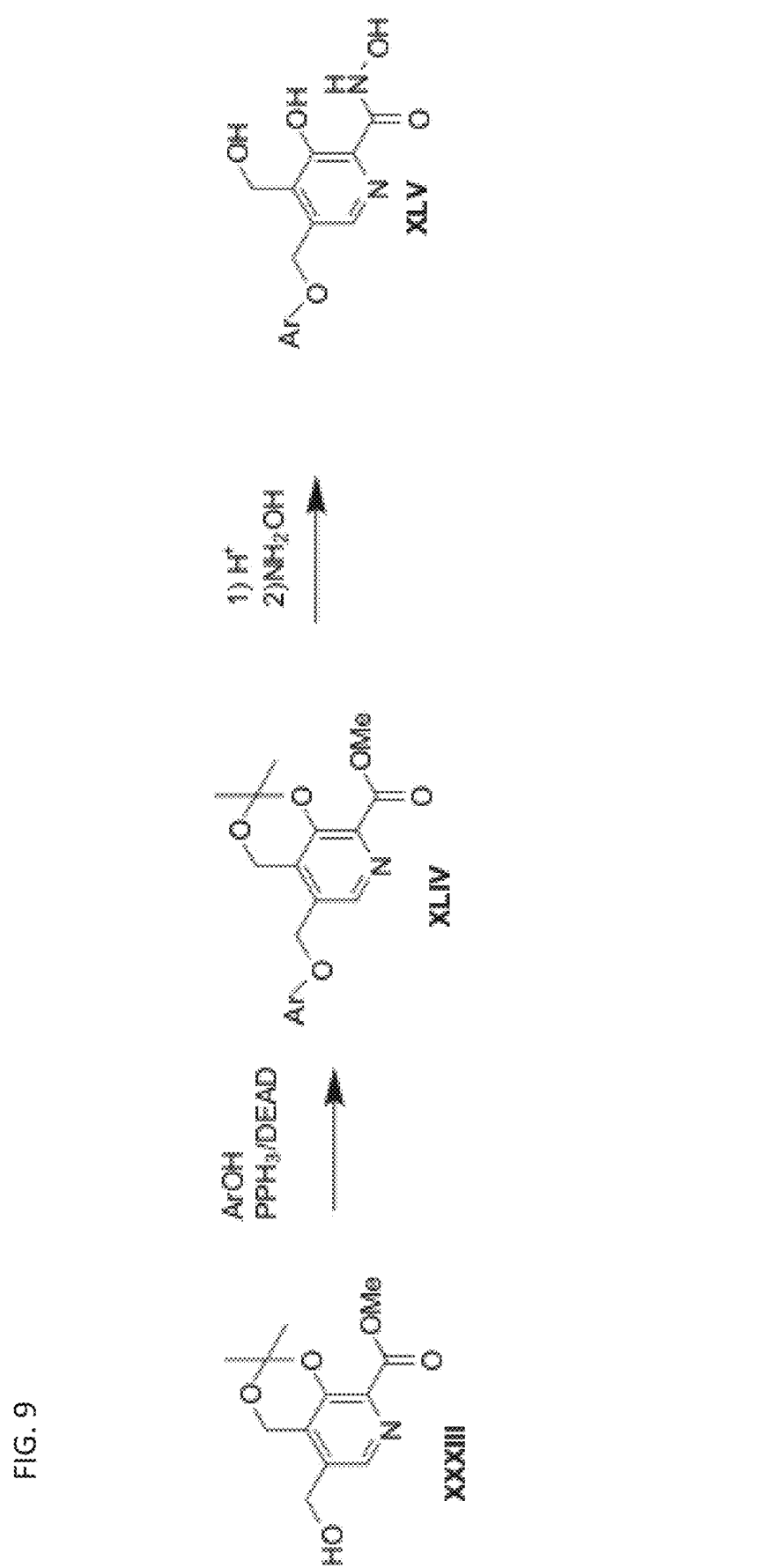
FIG. 9 is a synthetic scheme showing the synthesis of compound XLV.

In some embodiments, the ninth approach (FIG. 9) begins with intermediate XXXIII, which is reacted in a Mitsunobu reaction with phenols to yield ethers XLIV. These ethers may then be exposed to aqueous formic acid, and then reacted with hydroxylamine to yield products XLV.

Figure 10:
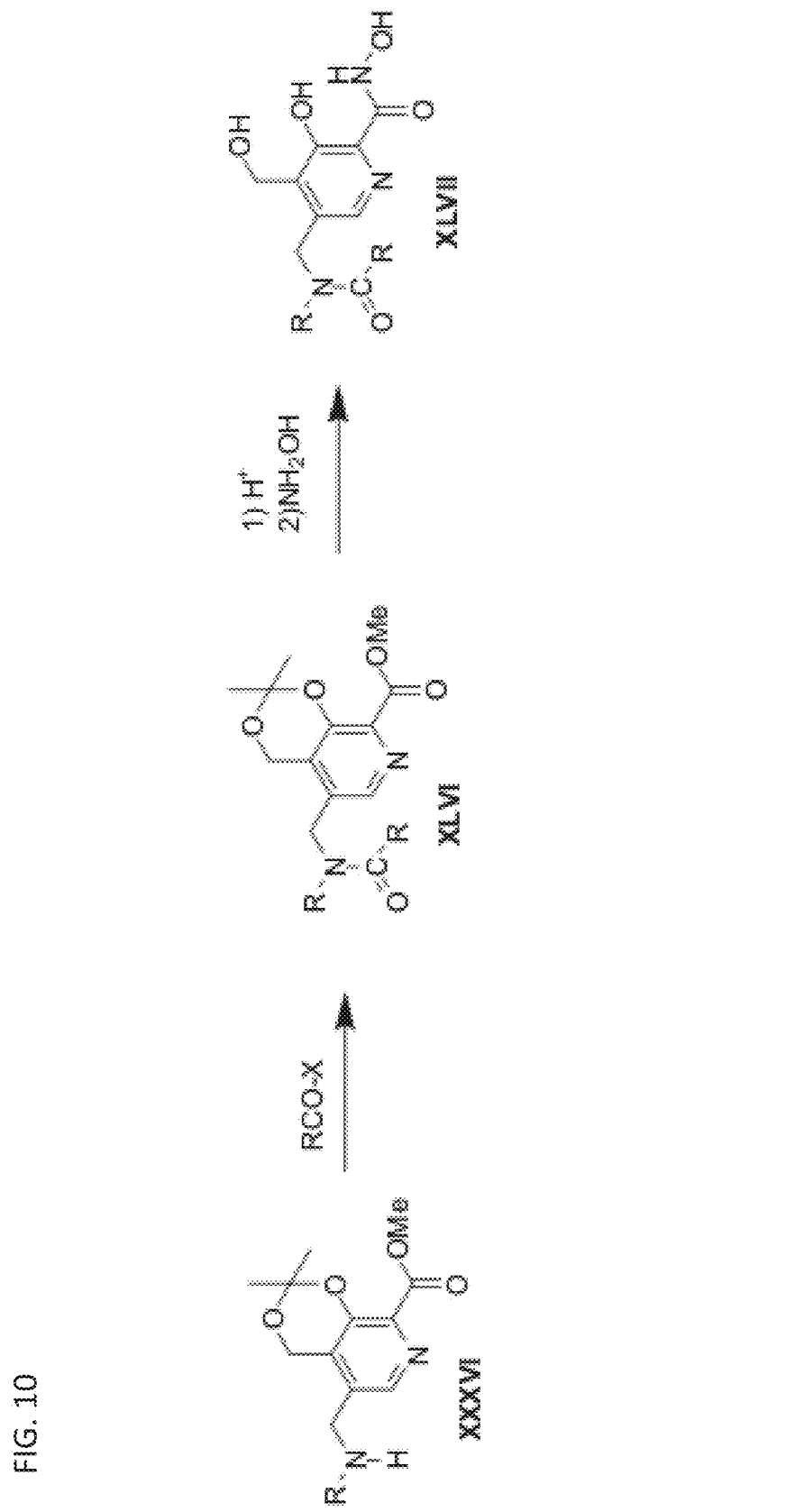
FIG. 10 is a synthetic scheme showing the synthesis of compound XLVII.

In some embodiments, the tenth approach (FIG. 10) consists of acylation of compounds XXXVI by activated carboxylic acids, acyl halides, chloroformates isocyanates, and other electrophiles, to obtain compounds of the form XLVI. XLVI compounds can then be exposed to aqueous formic acid, and reacted with hydroxylamine to yield product XLVII.

Figure 11:
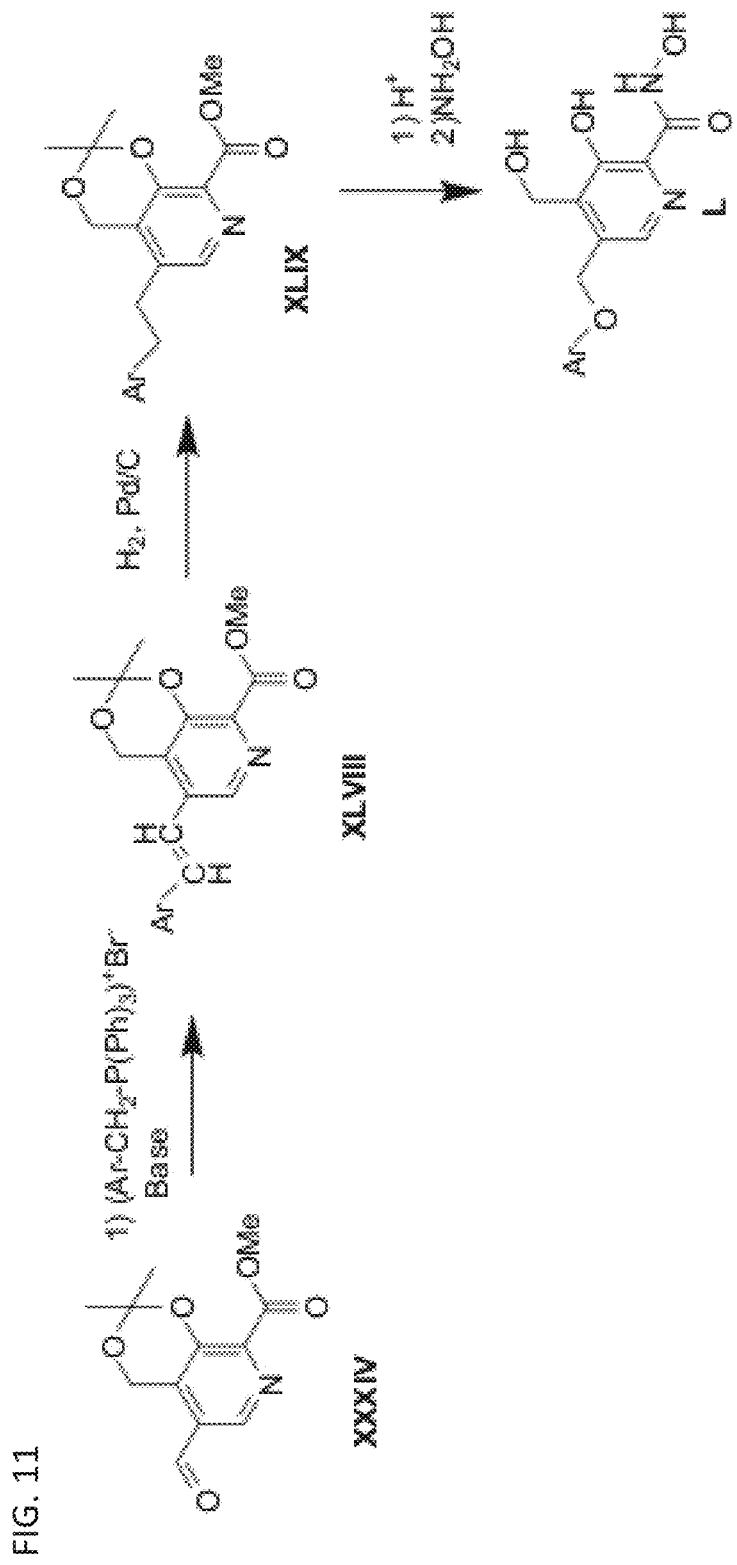
FIG. 11 is a synthetic scheme showing the synthesis of compound L.

In some embodiments, the eleventh approach (FIG. 11) begins with a Wittig reaction of intermediate XXXIV to yield alkenes of the form XLVII. XLVII may then be hydrogenated producing saturated alkanes, then further exposed to aqueous formic acid, and reacted with hydroxylamine to yield products L.

Figure 12:
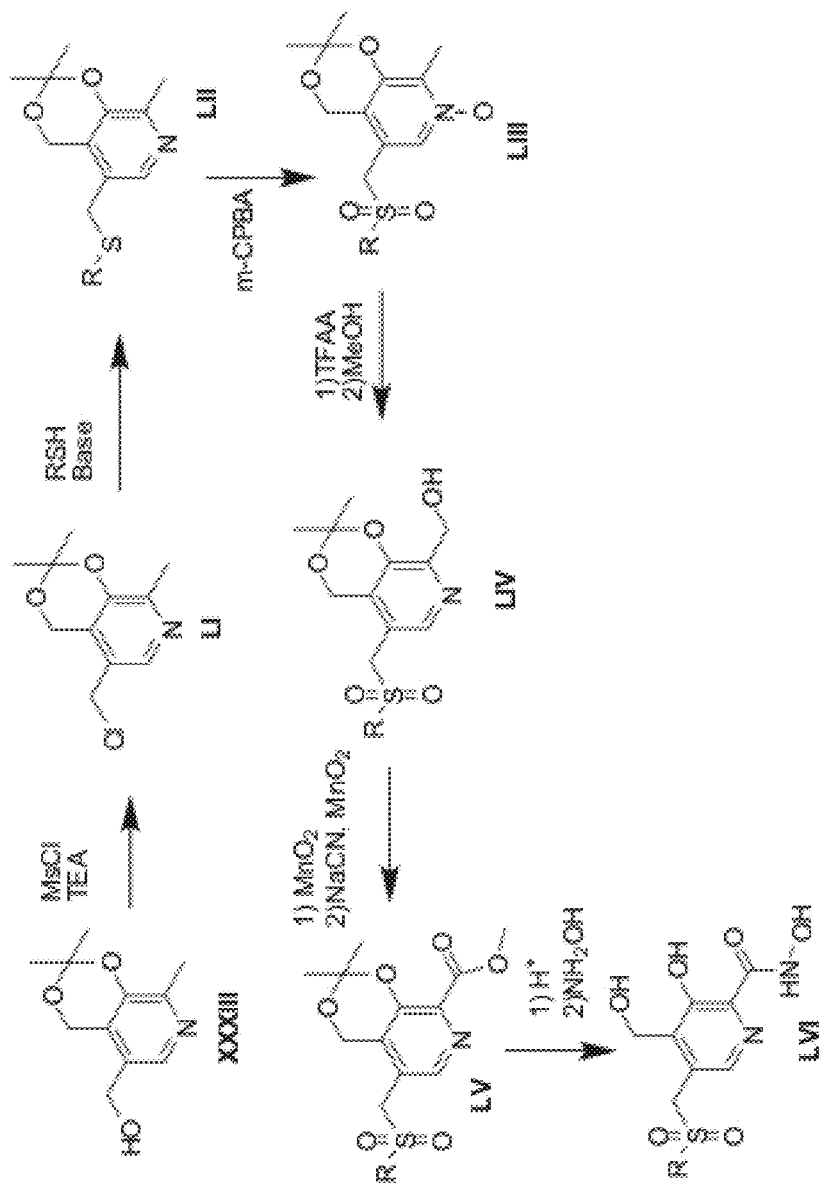
FIG. 12 is a synthetic scheme showing the synthesis of compound LVI.

In some embodiments, the twelfth approach (FIG. 12) begins with intermediate XXXIII and reaction of XXXIII with methane sulfonyl chloride to yield the reactive intermediate alkyl chloride LI. In some embodiments, LI is immediately and cautiously reacted with a mercaptan to yield the thioether LII. Reaction of LII with excess peroxide mCPBA can yield a sulfone-N-oxide intermediate LIII, which upon exposure to trifluoroacetic anhydride can rearrange to products LIV. The intermediate alcohol may then be oxidized in a stepwise manner to LV esters, which are then exposed to aqueous formic acid and reacted with hydroxylamine to yield products LVI.

It can be appreciated by those skilled in the art that the above synthetic schemes are not intended to be a comprehensive list of all means by which the above compounds may be synthesized.

Further methods will be evident to those of ordinary skill in the art.

General Procedures

General procedures can be found as described in U.S. Pat. No. 8,742,123 B$_2$.

EXAMPLES

The following examples are provided to illustrate, but are not limited to, the presently claimed invention.

Example 1. Preparation of 5-[(4-fluoro-phenylamino)-methyl]-3-hydroxy-4-hydroxymethyl-pyridine-2-carboxylic acid hydroxyamide (Compound 1)

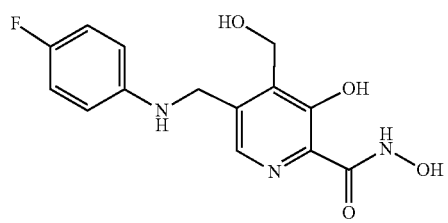 [SMILES: O=C(NO)c1ncc(CNc2ccc(F)cc2)c(CO)c1O]

Step 1a. Preparation of methyl 5-((4-fluorophenyl-amino) methyl)-2,2-dimethyl-4H-[1,3]dioxino[4,5-c]pyridine-8-carboxylate (Compound 1 a): Acetic acid (50 µL, 0.87 mmol) was added to a mixture of 5-formyl-2,2-dimethyl-4H-[1,3]dioxino[4,5-c]pyridine-8-carboxylic acid methyl ester (J. Org. Chem. 1999, 64, 4537) (220 mg, 0.87 mmol) and 4-fluoroaniline (125 µL, 1.3 mmol) in dry methanol (4 mL) and stirred at room temperature for 15 min and sodium cyanoborohydride (72 mg, 1.3 mmol) was added. This mixture was stirred at room temperature for 3 h followed by evaporation of 90% of the methanol volume under reduced pressure. The residue was extracted with dichloromethane (3×25 mL) and the combined organic layers were dried (anh. $Na_2SO_4$), filtered and concentrated under reduced pressure. The crude product was purified by silica gel (methanol/dichloromethane, 0 to 10% methanol) to give 0.290 g of methyl 5-((4-fluorophenylamino)methyl)-2,2-dimethyl-4H-[1,3]dioxino[4,5-c]pyridine-8-carboxylate (Compound 1a) (96%) as a white solid MS-ESI m/z 347 [MI-1]+.

Step 1b. Preparation of 5-((4-fluorophenylamino)methyl)-3-hydroxy-4-(hydroxymethyl)picolinate (Compound 1b): Formic acid (2 mL) was added to methyl 5(4-fluorophenylamino)methyl)-2,2-dimethyl-4H-[1,3]dioxino[4,5-c]pyridine-8-carboxylate (180 mg, 0.5 mmol) at 0° C. and stirred at room temperature for 2 h. Evaporation under reduced pressure afforded a residue 5-((4-fluoropheny-lamino)methyl)-3-hydroxy-4-(hydroxymethyl) picolinate (Compound 1b), which was triturated in acetonitrile. MS-ESI m/z 307 [MH]+.

Step 1c. Preparation of N5-(3,4-difluorobenzyl)-$N^2$,3-dihydroxy-4-(hydroxymethyl)pyridine-2,5-dicarboxamide (Compound 1c): Diisopropylethylamine (142 µL, 0.8 mmol) and hydroxylamine hydrochloride (45 mg, 0.64 mmol) were added to a solution of 5-((4-fluorophenylamino)methyl)-3-hydroxy-4-(hydroxymethyl)picolinate (Compound 1b) (50.0 mg, 0.16 mmol) in methanol (1.0 mL). The reaction mixture was heated to 55° C. for 16 h. The reaction mixture was allowed to cool to room temperature and a saturated solution of ammonium chloride was added. The reaction mixture was extracted with ethyl acetate (3×25 mL) and the combined organic layers were dried (anhydrous $Na_2SO_4$), filtered and concentrated under reduced pressure to give a solid residue which was recrystallized in acetonitrile to give Compound 1.

Example 2. Preparation of 5-(4-fluoro-phenoxymethyl)-3-hydroxy-4-hydroxymethyl-pyridine-2-carboxylic acid hydroxyamide (Compound 2)

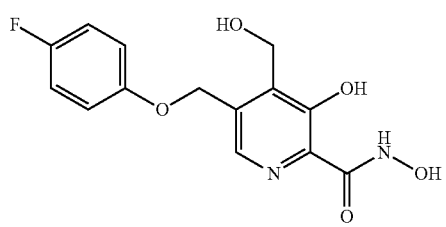 [SMILES: O=C(NO)c1ncc(COc2ccc(F)cc2)c(CO)c1O]

Step 2a. Preparation of methyl 5-((4-fluorophenoxy)methyl)-2,2-dimethyl-4H-[1,3]dioxino[4,5-c]pyridine-8-carboxylate (Compound 2a): Triphenylphosphine (0.105 g, 0.40 mmol), followed by diethyl azodicarboxylate (DEAD) (0.06 mL, 0.40 mmol) were added to a solution of methyl 5-(hydroxymethyl)-2,2-dimethyl-4H-[1,3]dioxino[4,5-c]pyridine-8-carboxylate (0.102 g, 0.40 mmol) in 10 mL of THF, at room temperature under Argon (Ar). The resulting mixture was stirred at room temperature for 6 h and then concentrated. The crude residue was purified by chromatography ($SiO_2$) with hexanes/ethyl acetate (1:1) as eluent to afford the title compound with a contaminant. LC-MS (M+H)+ m/z 348.

Step 2b. Preparation of methyl 5-((4-fluorophenoxy)methyl)-3-hydroxy-4-(hydroxymethyl)picolinate (Compound 2b): A solution of methyl 5-((4-fluorophenoxy)methyl)-2,2-dimethyl-4H-[1,3]dioxino[4,5-c]pyridine-8-carboxylate (Compound 2a) (0.129 g, 0.37 mmol) in 3 mL of formic acid was stirred at 23° C. for 2 h and then it was concentrated. The crude residue was purified by chromatography (SiO2) with hexanes/ethyl acetate (3:7) as eluent to afford the title compound as a white solid: LC-MS (M+H)+ m/z 308; 1H NMR (DMSO-d6): 1.39 (s, 6H), 4.80 (s, 2H), 4.89 (s, 2H), 5.01 (s, 2H), 7.39-7.46 (m, 55 5H), 8.38 (s, 1H), 10.04 (s, 1H).

Step 2c. Preparation of Compound 2: Hydroxylamine hydrochloride (0.045 g, 0.65 mmol) and N,N-diisopropylethylamine (0.14 mL, 0.81 mmol) were added to a solution of methyl 5-((4-fluorophenoxy)methyl)-3-hydroxy-4-(hydroxymethyl)picolinate (Compound 2b) (0.050 g, 0.16 mmol) in MeOH (3 mL) and heated to 70° C. for 5 h. The crude mixture was diluted with EtOAc and washed with saturated aqueous ammonium chloride solution and brine. The organic extract was dried ($Na_2SO_4$), filtered and concentrated in vacuo to afford the title compound (0.048 g, 96% yield): LC-MS $(M+H)^+$ m/z 309.

Example 3. Preparation of 5-(3-chloro-4-fluoro-phenoxymethyl)-3-hydroxy-4-hydroxymethyl-pyridine-2-carboxylic acid hydroxyamide (Compound 3)

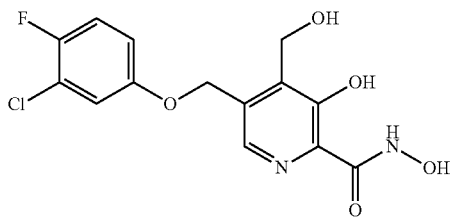 [SMILES: O=C(NO)c1ncc(COc2ccc(F)c(Cl)c2)c(CO)c1O]

Step 3a. Preparation of methyl 5-((3-chloro-4-fluorophenoxy)methyl)-2,2-dimethyl-4H-[1,3]dioxino[4,5-c]pyridine-8-carboxylate (Compound 3a): Using similar procedure as described in the Example 2 of methyl 5-((4-fluorophenoxy)methyl)-2,2-dimethyl-4H-[1,3] dioxino[4,5-c]pyridine-8-carboxylate (Step 2a), obtained compound 3a: ESI-MS $(M+H)^+$ m/z 382.

Step 3b. Preparation of methyl 5-((3-chloro-4-fluorophenoxy)methyl)-3-hydroxy-4(hydroxymethyl) picolinate (Compound 3b): Using similar procedure as described in Example 2, in the preparation of methyl 5-((4-fluorophenoxy)methyl)-3-hydroxy-4-(hydroxymethyl)picolinate (Compound 2b), Compound 3b was obtained as a white solid (63% yield); LC-MS $(M+H)^+$ m/z 342.

Step 3c. Preparation of Compound 3: Using similar procedure as described in the Example 2, in the preparation of 5-((4-fluorophenoxy)methyl)-$N,^3$-dihydroxy-4-(hydroxymethyl)picolinamide, Step 2c, Compound 3 was obtained as a beige solid (98% yield); LC-MS (M+H)+ m/z 342.

Example 4. Preparation of N⁵-(3-chloro-4-fluo-robenzyl)-N²,3-dihydroxy-4-(hydroxymethyl)pyridine-2, 5-dicarboxamide (Compound 4)

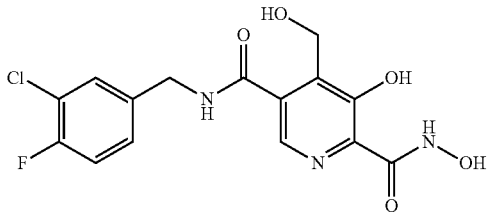 [SMILES: O=C(NCc1ccc(F)c(Cl)c1)c1cnc(C(=O)NO)c(O)c1CO]

N²,3-bis(benzyloxy)-N⁵-(3-chloro-4-fluorobenzyl)-4-(hydroxymethyl)pyridine-2,5-dicarboxamide (0.03 g, 0.330 mmol) and 10% Pd/C catalyst (25 mg) were stirred in methanol (4.0 mL) under an atmosphere of hydrogen for 1 h. The catalyst was filtered and the reaction mixture was concentrated under vacuum yielding 0.015 g of N⁵-(3-chloro-4-fluorobenzyl)N²,3-dihydroxy-4-(hydroxymethyl) pyridine-2,5-dicarboxamide as a white solid; ¹H NMR (400 MHz, DMSO-d6, ppm): δ 13.01 (s, 1H), 12.0 (s, 1H), 9.51 (s 1H), 9.02 (t 1H), 8.11 (s, 1H), 7.60 (d 1H), 7.40 (m, 2H), 4.68 (s, 2H), 4.48 (s, 2H); MS-ESI m/z 370 [MH]⁺.

Example 5. Preparation of 5-{(1-3-chloro-4-fluoro-phenyl)aminomethyl} 2,2-dimethyl-4H-[1,3]dioxino[4,5-c]pyridine-8-carboxylic acid hydroxamide (Compound 5)

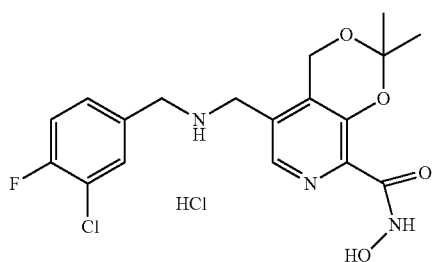 [SMILES: CC1(C)OCc2c(CNCc3ccc(F)c(Cl)c3)cnc(C(=O)NO)c2O1 ; Cl]

251 mg of 5-formyl-2,2-dimethyl-4H-[1,3]dioxino[4,5-c] pyridine-8-carboxylic acid methyl ester (J. Org. Chem. 1999, 64, 4537) (1 mmol) and 3-chloro-4-fluorobenzylamine (125 µL, 1.3 mmol) in dry methanol (4 mL) were stirred at room temperature for 15 min and sodium cyanoborohydride (72 mg, 1.3 mmol) was added. This mixture was stirred at room temperature for 3 h followed by evaporation of 90% of the methanol volume under reduced pressure. The residue was extracted with dichloromethane (3×25 mL) and the combined organic layers were dried (anh. Na₂SO₄), filtered and concentrated under reduced pressure. The crude product was purified by silica gel (methanol/dichloromethane, 0 to 10% methanol) to give 0.300 mg of 5-{(1-3-chloro-4-fluorophenyl)aminomethyl} 2,2-dimethyl-4H-[1,3]dioxino[4,5-c] pyridine-8-carboxylic acid hydroxamide. 50 mg of this compound was then dissolved in dry EtoAc and a solution of HCl in ether was added dropwise until precipitate was no longer seen to form. This precipitate was filtered and dried in a desiccator yielding 40 mg of a slightly hygroscopic material.

Example 6. Preparation of 5-[2-(4-fluoro-phenyl)-ethyl]-3-hydroxy-4-hydroxymethyl-pyridine-2-carboxylic acid hydroxamide (Compound 6)

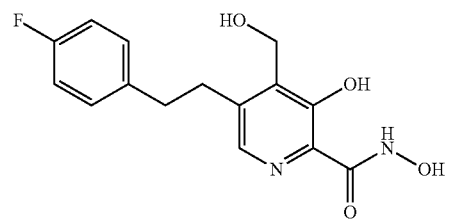

Compound 6 was synthesized by reaction of 5-formyl (0.751 g, 3 mmol) and 1000 mg (3.5 mmol) (4-fluorobenzyl) triphenyphosphonium bromide in THF at –78° C. then stirred overnight at room temperature. The reaction was quenched with NH₄Cl (saturated). The crude product was separated on silica gel to yield 417 mg (31% yield). This product was hydrogenated by catalytic hydrogenation over Pd/C 5% in EtOAc. Silica gel chromatography purification yielded 305 mg, which was reacted with hydroxylamine (excess) in ethanol (2 h, 80° C.). The compound was precipitated 1N HCl, filtered and redissolved in MeOH with the addition of 6 N HCl, stirred for 4 h, followed by evaporation, providing the desired product. MS-ESI m/z 307 [MH]+.

Example 7. Preparation of 5-(4-methoxy-benzyloxymethyl)-3-hydroxy-4-methyl-pyridine-2-carboxylic acid (Compound 7)

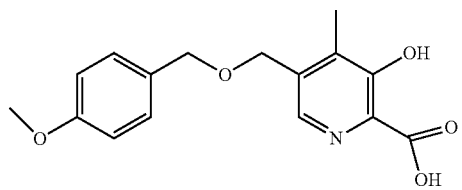 [SMILES: COc1ccc(COCc2cnc(C(=O)O)c(O)c2C)cc1]

0.05 g (0.15 mmol) of Compound 8 was dissolved in dry THF. 2 equiv (0.3 mmol) of potassium trimethylsilanoate was added and the mixture warmed forming a slurry. Rapid stirring overnight at 75° C. showed complete conversion. Concentration of the solution, resolution in 25 mL EtoAc and acidification with 1.0 N HCl was done with the extraction of the compound into the organic phase. The organic phase was dried over brine then evaporated to dryness giving the desired compound.

Example 8. Preparation of 5-(4-methoxy-benzyloxymethyl)-3-hydroxy-4-methyl-pyridine-2-carboxylic acid methyl ester (Compound 8)

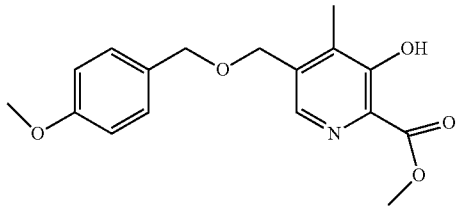 [SMILES: COC(=O)c1ncc(COCc2ccc(OC)cc2)c(C)c1O]

0.5 g (1.5 mmol) of methyl 3-hydroxy-4-(hydroxymethyl)-5-((4-ethoxybenzyloxy)methyl)picolinate was dissolved in 2 mL Ac$_2$O and stirred for 2 h. 5 mL MeOH was added and the solvent was evaporated to dryness. The residue was dissolved in 50 mL degassed, N$_2$ flushed EtOAc. 0.25 g 10% Pd/C was added. H$_2$ gas was bubbled in for 4 h and the mixture left to stir overnight. N$_2$ was bubbled in and the solution filtered over a pad of silica gel. The clear solution was then evaporated to dryness and the resulting syrup crystallized to give the desired product quantitatively.

Example 9. Preparation of 5-((4-methoxybenzyloxy)methyl)-2,2,8-trimethyl-4H-[1,3]dioxino[4,5-c]pyridine (Compound 9)

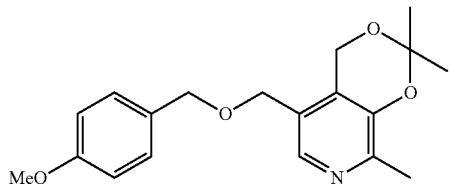 [SMILES: COc1ccc(COCc2cnc(C)c3c2COC(C)(C)O3)cc1]

Anhydrous THF (200 mL) was added to NaH (60%, 24 g, 600 mmol) at 0° C. under a nitrogen atmosphere. To this suspended mixture a solution of 2,2,8-trimethyl-4H-[1,3]dioxino[4,5-c]pyridin-5-yl)methanol (32.0 g, 150 mmol) in 400 mL of THF (J. Med. Chem., 1977, 20, 745) was added. The resulting mixture was refluxed for 30 min; a significant amount of precipitate accumulated during the reflux. After cooling to room temperature, p-methoxybenzyl chloride (23.5 g, 150 mmol) was introduced drop-wise and the resulting mixture was refluxed for another 8 h. The reaction was quenched carefully by adding ice-cold water to the viscous mixture at 0° C. and diluted with a saturated ammonium chloride solution followed by extraction with methylene chloride. The combined organic extracts were washed with brine, dried (Na$_2$SO$_4$), and concentrated yielding a brown oil. The crude product was purified by chromatography (10% ethyl acetate/petroleum ether) yielding 25.0 g of Compound 9 (50% yield); LC-MS (M+H)$^+$ m/z 331.

Example 10. Preparation of methyl 5-((4-methoxybenzyloxy)methyl)-2,2-dimethyl-4H-[1,3]dioxino[4,5-c]pyridine-8-carboxylate (Compound 10)

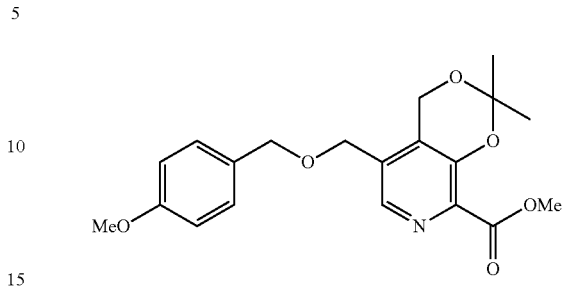

Step 10a. 5-((4-Methoxybenzyloxy)methyl)-2,2,8-trimethyl-4H-[1,3]dioxino[4,5-c]pyridine 7-oxide

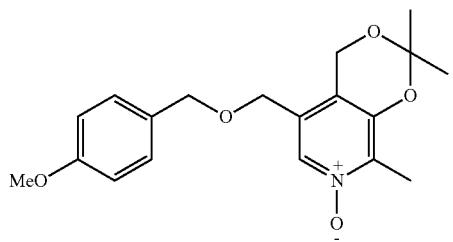

5-((4-Methoxybenzyloxy)methyl)-2,2,8-trimethyl-4H-[1,3]dioxino[4,5-c]pyridine (50.0 g, 152 mmol, 1.0 equiv) was dissolved in dry CH$_2$Cl$_2$ (500 mL) and the solution was cooled to 0° C. To this solution was added m-chloroperbenzoic acid (85% purity of the reagent, 37.0 g, 182 mmol, 1.2 equiv). After being stirred at 23° C. for 12 h, the reaction mixture was extracted with Na$_2$SO$_3$ (10%, 2×200 mL), NaHCO$_3$ (5%, 2×200 mL), H$_2$O, dried (Na$_2$SO$_4$), filtered and the solvent was removed under reduced pressure. The crude product was purified by chromatography (10% methanol/ethyl acetate) to afford the title compound as pale-yellow solid (35 g, 68%); LC-MS (M+H)$^+$ m/z 346.

Step 10b. (5-((4-Methoxybenzyloxy)methyl)-2,2-dimethyl-4H-[1,3]dioxino[4,5-c]pyridin-8-yl)methanol

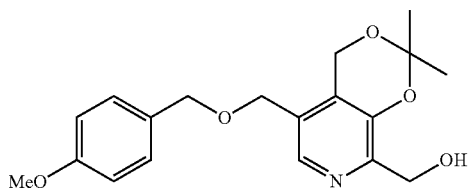 [SMILES: COc1ccc(COCc2cnc(CO)c3c2COC(C)(C)O3)cc1]

Trifluoroacetic anhydride (4.5 mL, 32 mmol) was added to a solution of 5-((4-methoxybenzyloxy)methyl)-2,2,8-trimethyl-4H-[1,3]dioxino[4,5-c]pyridine 7-oxide (21.2 g, 61 mmol) in dry CH$_2$Cl$_2$ (200 mL) at 0° C. and stirred for 5 min. An additional amount of trifluoroacetic anhydride (11.5 mL, 82.7 mmol) was added and the reaction mixture was stirred overnight at 23° C. Then, the reaction mixture was cooled to 0° C. and MeOH (150 mL) was added while stirring was continued. The solvents were evaporated and the resulting residue was dissolved in CH$_2$Cl$_2$ and washed with Na$_2$CO$_3$ (20% aqueous) and H$_2$O until pH was neutral. The organic phase was dried (Na$_2$SO$_4$), filtered and concentrated in vacuo. The residue was crystallized from EtOH—CH$_2$Cl$_2$ to afford the title compound (17.5 g, 83%); LC-MS (M+H)+ m/z 346.

Step 10c. 5-((4-Methoxybenzyloxy)methyl)-2,2-dimethyl-4H-[1,3]dioxino[4,5-c]pyridine-8-carbaldehyde

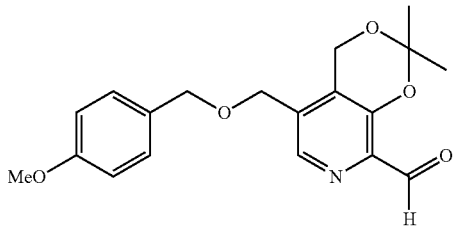 [SMILES: COc1ccc(COCc2cnc(C=O)c3c2COC(C)(C)O3)cc1]

To a solution of (5-((4-methoxybenzyloxy)methyl)-2,2-dimethyl-4H-[1,3]dioxino[4,5-c]pyridin-8-yl)methanol (14.60 g, 42.3 mmol) in ethyl acetate (500 mL) was added IBX (35.5 g, 128 mmol) and the suspension was heated to reflux for 4 h. The precipitate was removed by filtration and the filtrate was concentrated under reduced pressure to afford the title compound (14.0 g, 95%). The crude material was used for the next step without further purification: LC-MS (M+H)$^+$ m/z 344.

Step 10d. Methyl 5-((4-methoxybenzyloxy)methyl)-2,2-dimethyl-4H-[1, 3]dioxino[4,5-c]pyridine-8-carboxylate To the solution of 5-((4-methoxybenzyloxy)methyl)-2,2-dimethyl-4H-[1,3]dioxino[4,5-c]pyridine-8-carbaldehyde (10.3 g, 30 mmol) in anhydrous MeOH (120 mL), KOH (85%, 5.3 g, 78 mmol) and iodine (9.9 g, 39 mmol) were added at 0° C. The reaction mixture was kept at 23° C. and stirred for 12 h until no starting material was detected by TLC. Then, the solution was treated with Na$_2$SO$_3$ (solid) and the pH was adjusted to 7. The solid was filtered and solvent was removed under reduced pressure. The residue was dissolved in EtOAc and washed with water. The combined organic extracts were dried (Na$_2$SO$_4$), filtered and concentrated in vacuo. The crude residue was purified by chromatography (SiO$_2$) with petroleum ether:ethyl acetate (5:1) as eluent to afford the title compound as pale-yellow solid (8.8 g, 78%): LC-MS (M+H)$^+$ m/z 374.

Example 11. Preparation of 5-(4-methoxybenzyloxymethyl-3-hydroxy-4-methyl-pyridine-2-carboxylic acid hydroxyamide (Compound 11)

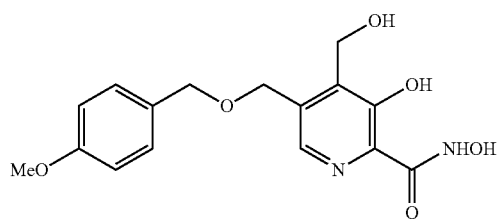

Step 11a. Methyl 3-hydroxy-4-(hydroxymethyl)-5-((4-methoxybenzyloxy)methyl)picolinate

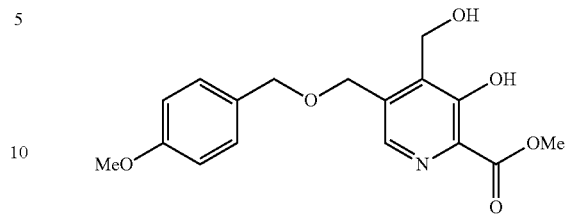

The solution of methyl 5-((4-methoxybenzyloxy)methyl)-2, 2-dimethyl-4H-[1,3]dioxino[4,5-c]pyridine-8-carboxylate (8.8 g, 23.6 mmol) in 200 mL of HCl/MeOH was stirred at 23° C. for 24 h. MeOH (500 mL) was added to dissolve the suspension and NaHCO$_3$ (solid) was added to neutralize the reaction mixture. The excess solid was filtered and the solvent was removed under reduced pressure. The residue was dissolved in EtOAc and washed with water. The combined organic extracts were dried (Na$_2$SO$_4$), filtered and concentrated in vacuo to afford the title compound as a light yellow solid (6.0 g, 100%): LC-MS (M+H)$^+$ m/z 334.

Step 11b. N,3-Dihydroxy-4-(hydroxymethyl)-5-((4-methoxybenzyloxy)methyl)picolinamide To a solution of methyl 3-hydroxy-4-(hydroxymethyl)-5-((4-methoxybenzyloxy)methyl)picolinate (0.050 g, 0.15 mmol) in MeCOH (3 mL) was added hydroxylamine hydrochloride (0.042 g, 0.60 mmol) and N,N-diisopropylethylamine (0.13 mL, 0.75 mmol). The resulting mixture was placed in the microwave and heated to 80° C. for 1.5 h. The crude mixture was diluted with EtOAc and washed with saturated aqueous ammonium chloride solution and brine. The organic extract was dried (Na$_2$SO$_4$), filtered and concentrated in vacuo to afford the title compound (0.039 g, 78%): LC-MS (M+H)$^+$ m/z 335.

Example 12. Preparation of methyl 5-((4-fluorophenylamino)methyl)-3-hydroxy-4-(hydroxymethyl) picolinate (Compound 12)

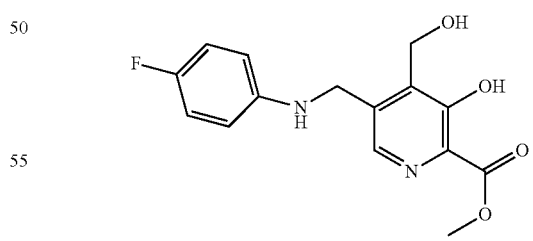

Formic acid (2 mL) was added to methyl 5(4-fluorophenylamino)methyl)-2,2-dimethyl-4H-[1,3]dioxino[4,5-c] pyridine-8-carboxylate (180 mg, 0.5 mmol) at 0° C. and stirred at room temperature for 2 h. Evaporation under reduced pressure afforded a residue 5-((4-fluorophenylamino)methyl)-3-hydroxy-4-(hydroxymethyl) picolinate, which was triturated in acetonitrile. MS-ESI m/z 307 [MH]$^+$.

Example 13. Preparation of N[5]-(2-N-methylcarboxamide-4-fluorobenzyl)-N[2],3-hydroxy-4-(hydroxymethyl)pyridine-2-methylcarboxylate, 5-carboxamide (Compound 13)

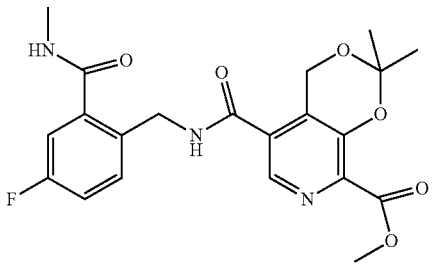 [SMILES: CNC(=O)c1cc(F)ccc1CNC(=O)c1cnc(C(=O)OC)c2c1COC(C)(C)O2]

100 mg of 5-carboxyl-2,2-dimethyl-4H-[1,3]dioxino[4,5-c]pyridine-8-carboxylic acid methyl ester was dissolved in 2 mL DMF and 0.2 mL N-methylmorpholine was added with about 300 mg HBTU. 100 mg 2-N-methylcarboxamide-4-fluorobenzylamine was added to the solution after approximately 30 min. The mixture was stirred overnight after which it was quenched by addition to 20 mL 10% citric acid. 25 mL EtOAc was added and the organic phase was washed with citric acid (2×), $K_2CO_3$ (2×), and brine. Yield was 101 mg. LCMS (100%) MS-ESI m/z 432[MH]$^+$.

Example 14. Preparation of methyl 3-(benzyloxy)-5-((4-fluorophenoxy)methyl)-4-methylpicolinate (Compound 14)

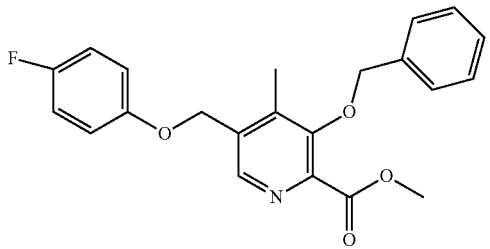 [SMILES: COC(=O)c1ncc(COc2ccc(F)cc2)c(C)c1OCc1ccccc1]

Using a procedure similar to that described in the Example 2, step 2a, Compound 14 was prepared as a colorless oil: 72% yield. LC-MS (M+H)F m/z 382.

Example 15. Preparation of methyl 5-((4-fluorophenoxy)methyl)-2,2-dimethyl-4H-[1,3]dioxino[4,5-c]pyridine-8-carboxylate (Compound 15)

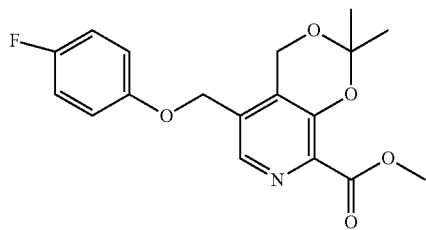 [SMILES: COC(=O)c1ncc(COc2ccc(F)cc2)c2c1OC(C)(C)OC2]

Triphenylphosphine (0.105 g, 0.40 mmol), followed by diethyl azodicarboxylate (DEAD) (0.06 mL, 0.40 mmol) were added to a solution of methyl 5-(hydroxymethyl)-2,2-dimethyl-4H-[1,3]dioxino[4,5-c]pyridine-8-carboxylate (0.102 g, 0.40 mmol) in 10 mL of THF, at room temperature under Ar. The resulting mixture was stirred at room temperature for 6 h and then concentrated. The crude residue was purified by chromatography ($SiO_2$) with hexanes/ethyl acetate (1:1) as eluent to afford the title compound with a contaminant. LC-MS (M+H)$^+$ m/z 348.

Example 16. Preparation of methyl 5-((4-fluorophenoxy)methyl)-3-hydroxy-4-(hydroxymethyl) picolinate (Compound 16)

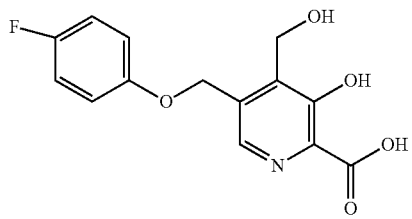 [SMILES: O=C(O)c1ncc(COc2ccc(F)cc2)c(CO)c1O]

A solution of methyl 5-((4-fluorophenoxy)methyl)-2,2-dimethyl-4H-[1,3]dioxino[4,5-c]pyridine-8-carboxylate (0.129 g, 0.37 mmol) in 3 mL of formic acid was stirred at 23° C. for 2 h and then it was concentrated. The crude residue was purified by chromatography ($SiO_2$) with hexanes/ethyl acetate (3:7) as eluent to afford the title compound as a white solid. LC-MS (M+H)$^+$ m/z 308; $^1$H NMR (ppm, DMSO-d6): 1.39 (s, 6H), 4.80 (s, 2H), 4.89 (s, 2H), 5.01 (s, 2H), 7.39-7.46 (m, 55 5H), 8.38 (s, 1H), 10.04 (s, 1H).

The solid was then dissolved in THF containing 1 mmol KOTMS and refluxed for 1 h. The resulting slurry was dropped in cold hexanes and filtered off. The hygroscopic filtrated was dissolved in water and acidified with 90% formic acid to form the carboxylic acid. This was filtered off and dried in vacuo. Yield: 40 mg off-white powder (blue fluorescence under UV).

Example 17. Preparation of methyl 5-((4-fluorophenoxy)methyl)-3-hydroxy-4-methylpicolinate (Compound 17)

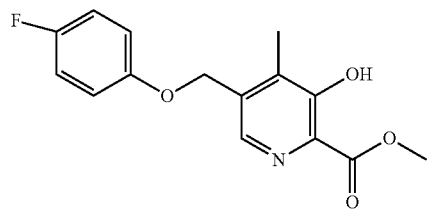 [SMILES: COC(=O)c1ncc(COc2ccc(F)cc2)c(C)c1O]

A solution of methyl 3-(benzyloxy)-5-((4-fluorophenoxy)methyl)-4-methylpicolinate (0.245 g, 0.64 mmol) in ethyl acetate (10 mL) was hydrogenated under 1 atm of hydrogen at 23° C. over 10% palladium on activated carbon for 1 h. The reaction mixture was filtrated and the solution was concentrated in vacuo to afford Compound 17 as a white solid (0.171 g, 92%). LC-MS (M+H)$^+$ m/z 292.

Example 18. Preparation of (3-chloro-4-fluoro-benzyl)-(5-hydroxy-6-hydroxycarbamoyl-4-hydroxymethyl-pyridin-3-ylmethyl)-carbamic acid benzyl ester (Compound 18)

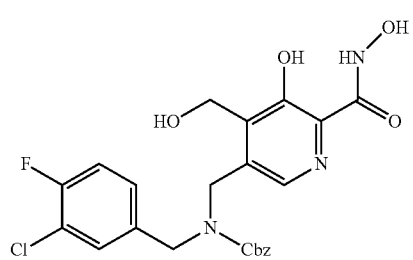 [SMILES: O=C(NO)c1ncc(CN(Cc2ccc(F)c(Cl)c2)C(=O)OCc2ccccc2)c(CO)c1O]

70 mg of Compound 5 was dissolved in DCM (20 mL). Triethylamine (100 µL) was then added followed by benzylchloroformate (~60 mg). The mixture was stirred for 4 h after which 20 mL 10% citric acid was added. The DCM phase was removed and further washed with $K_2CO_3$, dried over $Mg_2SO_4$ and evaporated to dryness. 1 mL formic acid (90%) was added and the solution warmed to 75° C. for 4 h. The solution was diluted with water forming a precipitate which was filtered and dried. The precipitate was taken up in 1 mL pyridine and 250 µL of 50% aq. hydroxylamine was added. The yellow solution was warmed to 80° C. for 8 h, after which the pyridine was removed in vacuo. Careful addition of cold 5% acetic acid yielded a precipitate which was filtered and washed with cold 5% acetic acid. Yield: 51 mg product. LC-MS $(M+H)^F$ m/z 490.1.

Example 19. Preparation of 4-hydroxymethyl-3-methoxy-pyridine-2,5-dicarboxylic acid 5-(4-fluoro-benzylamide) 2-hydroxyamide (Compound 19)

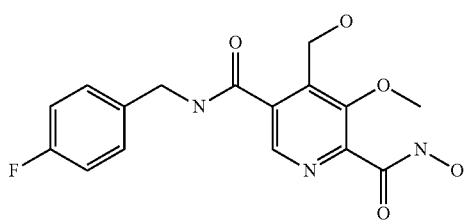 [SMILES: COc1c(C(=O)NO)ncc(C(=O)NCc2ccc(F)cc2)c1CO]

3-hydroxy-4-hydroxymethyl-pyridine-2,5-dicarboxylic acid 5-cyclohexylmethyl-amide 2-hydroxyamide (0.060 g, 0.137 mmol, 1 equiv) and 10% Pd/C (5 mg) in methanol (4.0 mL) were stirred under an atmosphere of hydrogen 1 h. The catalyst was filtered and reaction mixture was concentrated under vacuum to give 0.040 g of 53 (85%) as a white solid. MS-ESI m/z 350 [MH]⁺.

Example 20. Preparation of 3-hydroxy-4-hydroxymethyl-pyridine-2,5-dicarboxylic acid 5-dibenzylamide 2-hydroxyamide (Compound 20)

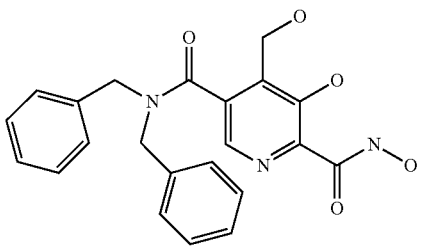 [SMILES: O=C(NO)c1ncc(C(=O)N(Cc2ccccc2)Cc2ccccc2)c(CO)c1O]

Procedure as described in U.S. Pat. No. 8,742,123 B2 Example 55.

Example 21. Preparation of 5-benzenesulfonylmethyl-3-hydroxy-4-hydroxymethyl-pyridine-2-carboxylic acid hydroxyamide (Compound 21)

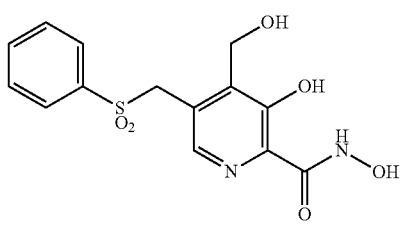 [SMILES: O=C(NO)c1ncc(CS(=O)(=O)c2ccccc2)c(CO)c1O]

550 mg of Compound I, of FIG. 1, was dissolved in 30 mL DCM was reacted with 2.5 equiv of methane sulfonyl chloride in the presence of 5 equiv triethylamine. Extraction was done with 5% citric acid, drying with $Na_2SO_4$, and evaporation yielded 500 mg of desired mesylate. This mesylate was immediately reacted with 400 mg of benzene sulfinic acid in DMF (2 mL). The product was isolated by precipitation in water and filtration. The crude was dissolved in CHCl₃ (30 mL) and 400 mg mCPBA (70%) was added. After 1 h stirring, the reaction was extracted using $K_2CO_3$ and the organic phase dried over $CaCO_3$ the evaporated. The residue was dissolved in 3 mL DCM and 3 mL trifluoroacetetic anhydride was added. Stirring at reflux 45° C. for 20 h affording the rearranged product, isolated through evaporation of solvent. The residue was then added to a solution of $MnO_2$ 2 g in CHCl₃ (30 mL) and stirred at reflux 1 h. Filtration and evaporation afforded the aldehyde (250 mg). This was placed in 10 mL MeOH with 1.2 equiv 12 and 3 equiv KOTMS. Stirring at room temperature for 1 h gave the ester in quantitative conversion. The product was purified on silica gel. 100 mg of the ester was reacted with excess (hydroxylamine 50% aquiv) in pyridine to give the hydroxamate. Dilution in EtOAc and extraction with 5% citric acid gave the desired intermediate. The final product was obtained by adding 50 mg of the above acetonide to neat 70% formic acid. After 15 min the reaction is complete, the formic acid is evaporated off and the residue triturated with water to give Compound 21 as a white powder. MS-ESI m/z 339 [MH]⁺.

Example 22. Preparation of 5-((3-chloro4-fluorobenzylamino)methyl)-4-(hydroxymethyl)picolinhydroxamide (Compound 22)

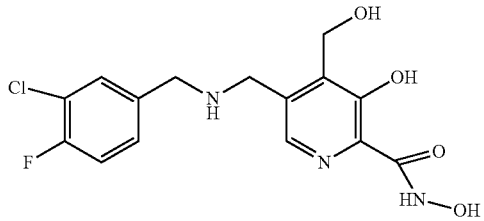 [SMILES: O=C(NO)c1ncc(CNCc2ccc(F)c(Cl)c2)c(CO)c1O]

25 mg of Compound 18 and 10% Pd/C catalyst (5 mg) were stirred in 4 mL of methanol under an atmosphere of hydrogen for 12 h. The catalyst was filtered and reaction mixture was concentrated under vacuum yielding 0.018 g of Compound 22 as a white solid; MS-ESI m/z 356 [MH]$^+$.

Example 23. Preparation of 3-hydroxy-4-hydroxymethyl-pyridine-2,5-dicarboxylic acid 5-(4-fluoro-benzylamide)2-(methoxy-amide) (Compound 23)

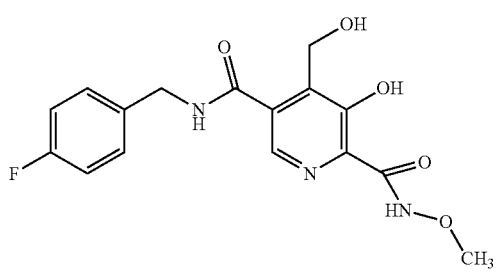 [SMILES: CONC(=O)c1ncc(C(=O)NCc2ccc(F)cc2)c(CO)c1O]

Formic acid (2 mL) was added to 2-dimethyl-4H-[1,3]dioxino[4,5-c]pyridine-5,8-dicarboxylic acid 5-(4-fluoro-benzyla-mide)8-(methoxy-amide) (0.048 g, 0.123 mmol, 1 equiv). The reaction mixture was stirred at room temperature 10 min. Formic acid was concentrated under vacuum and solid was triturated with diethyl ether under to give 0.030 g of Compound 23 (71%) as a white solid. MS-ESI m/z 350 [MH]$^+$.

Example 24. Preparation of 5-(4-fluoro-benzyloxymethyl)-3-hydroxy-4-hydroxymethyl-pyridine-2-carboxylic acid hydroxyamide (Compound 24)

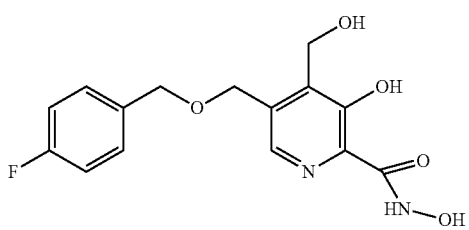 [SMILES: O=C(NO)c1ncc(COCc2ccc(F)cc2)c(CO)c1O]

Procedure as described in U.S. Pat. No. 8,742,123 B$_2$, Example 34, or as in Compound 11, using 4-fluorobenzyl bromide in the initial step.

Example 25. Preparation of 2,2-dimethyl-4H-[1,3]dioxino[4,5-c]pyridine-5,8-dicarboxylic acid 5-(3-chloro-4-fluoro-benzylamide)-8-(methyl ester) (Compound 25)

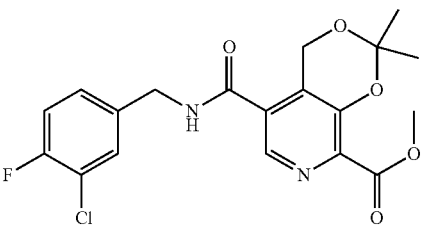 [SMILES: COC(=O)c1ncc(C(=O)NCc2ccc(F)c(Cl)c2)c2c1OC(C)(C)OC2]

Prepared as in Example 13a using 3-chloro-4fluorobenzyl amine in the initial step.

Example 26. Preparation of 5-((4-fluorophenoxy)methyl)-2,2-dimethyl-4H-[1,3]dioxino[4,5-c]picoline (Compound 26)

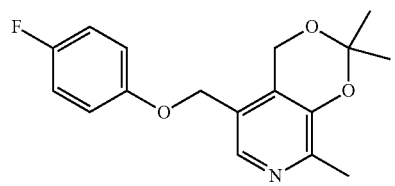 [SMILES: Cc1ncc(COc2ccc(F)cc2)c2c1OC(C)(C)OC2]

2.09 g (3.5 mmol) of 5-hydroxymethyl2,2-dimethyl-4H-[1,3]dioxino[4,5-c]picoline was dissolved in 50 mL EtOAc then cooled to 0° C. 1 mL triethylamine was added followed by 1.15 g pf methane sulfonyl chloride. The mixture was stirred for 30 min. A solution of 1.12 g 4-fluorophenol in 5 mL DMF was cooled to 0° C. and 1.12 g potassium tert-butanoate was added to form a phenol salt. This solution was added to the other at which point a gel formed. This was stirred and allowed to warm to room temperature for 1 h. The solution was then quenched by addition of water and adjusting the pH to 4 with acetic acid. The organic phase was evaporated. The residue was then adsorbed on silica gel then washed over a pad of silica gel with DCM. The DCM was evaporated to yield 2.4 g of a clear oil which spontaneously crystallized.

Example 27. Preparation of 5-((4-fluorophenoxy)methyl)-3-hydroxy-4-(hydroxymethyl)picoline (Compound 27)

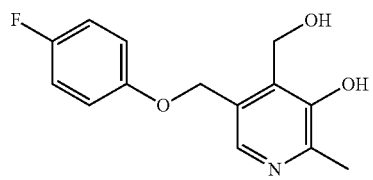 [SMILES: Cc1ncc(COc2ccc(F)cc2)c(CO)c1O]

50 mg of the compound from Example 26 was dissolved in 1 mL of 90% formic acid. The mixture was warmed to 75° C. for 4 h. The formic acid was removed by vaccum and the residue triturated in water to give an off-white powder suspension. This was filtered to give 26 mg of the desired compound.

Example 28. Cell Culture and Treatments

Figure 19:
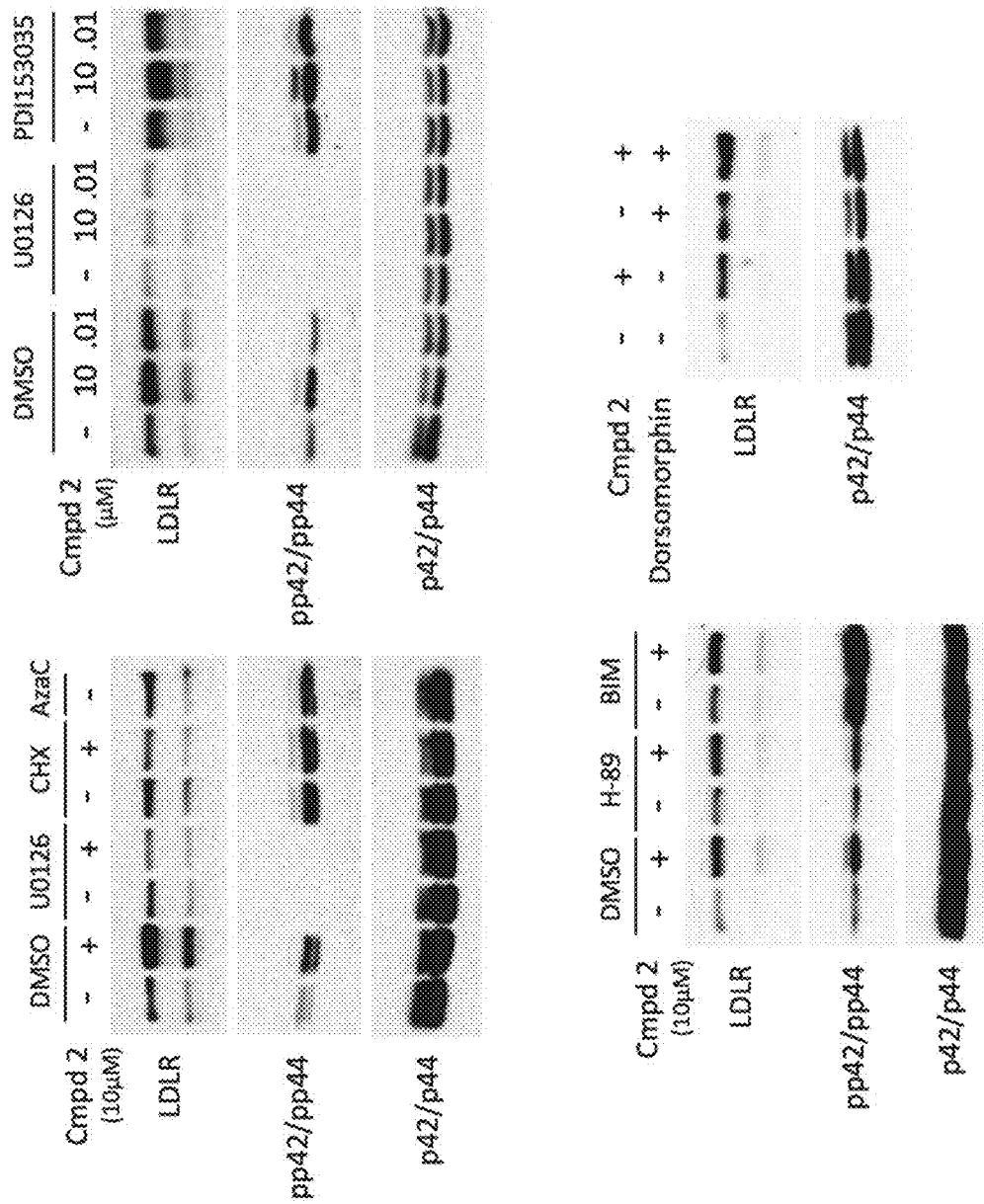
FIG. 19 is a series of graphs showing the effects of Compound 2 and different combined inhibitors on LDLR protein levels by Western blot analyses in HepG2 cells.

Human hepatoma cell lines HepG2 and Huh-7 were routinely cultivated in Dulbecco's modified Eagle's medium (DMEM; catalog no. 319-005-CL, Wisent) supplemented with 10% fetal bovine serum (FBS; catalog no. 080-350, Wisent). For phenotypic screening of LDLR small molecule inducers Examples 1-27, cells were incubated overnight in conditioned media containing giving chemical compounds 1-27 resuspended in DMSO at concentration ranging from 100 μM to 10 μM. For sterol-regulated conditions, HepG2 cells were incubated in 5% LPDS, 50 μM mevastatin, and 50 μM mevalonolactone in the absence (−sterols) or presence of 1 μg/ml 25-hydroxycholesterol and 10 μg/ml cholesterol (+sterols). For inhibitor treatments HepG2 cells were treated with DMSO or 10 μM compounds 2 in combination with U0126 (25 μM, catalog no. 9903, Cell Signaling Technology), Cycloheximide (CHX; 20 μg/ml, catalog no. C7698, Sigma-Aldrich), PD153035 (20 μM, catalog no. 14879, Cayman Chemical), bisindolylmaleimide I (BIM; 10 μM, catalog no. 13298, Cayman Chemical), H-89 (10 μM, catalog no. 10010556, Cayman Chemical), Dorsomorphin (5 μM, catalog no. 11967, Cayman Chemical) or 5-Azacytidine (10 μM, catalog no. A2385, Sigma-Aldrich). FIG. 19 shows that CHX and U0126, and no other tested inhibitor, block increase of LDLR by Compound 2.

Human embryonic kidney 293 (HEK-293, catalog no. CRL-1573; ATCC) cells were cultivated in complete DMEM without sodium pyruvate (catalog no. 319-015-CL, Wisent) and human umbilical vein/vascular endothelium cells (HUVEC; catalog no CRL-1730, ATCC) in F12 K media (catalog no. 312-250-CL, Wisent) both supplemented with 10% fetal bovine serum (FBS; catalog no. 080-350, Wisent).

Example 29. Western Blot Analysis

Figure 13B:
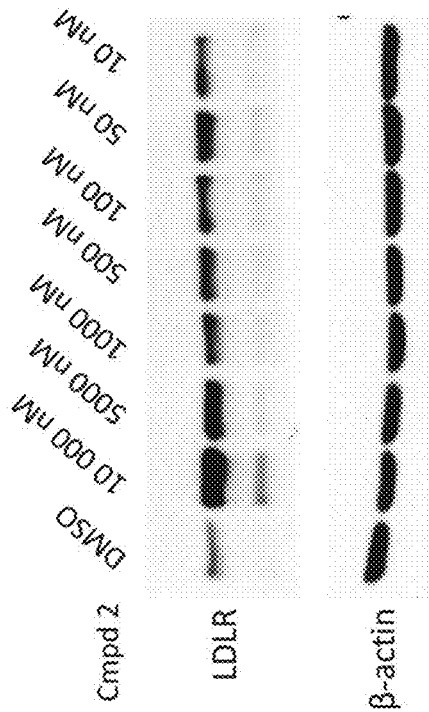
FIG. 13A to FIG. 13C are a series of images and graphs showing: (A and B) Western blot analysis and relative quantitation of LDLR protein of Compounds 1, 2, 3, and 21, in the HepG2 cell line, (C) dose response effect of Compound 2 in HepG2 cells.
Figure 13C:
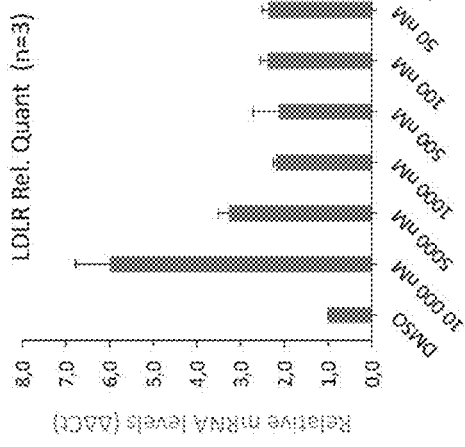
Figure 13A:
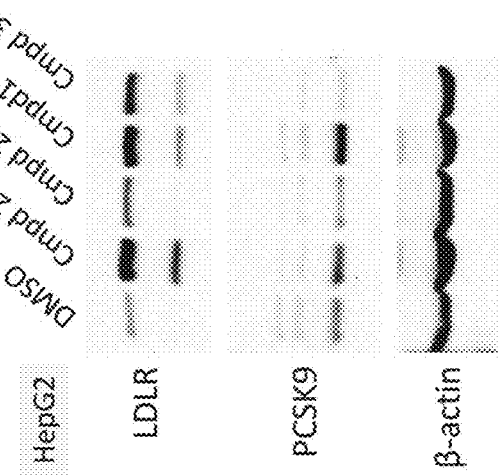

Treated cells from Example 28 were washed three times in phosphate-buffered saline (PBS) and lysed in radioimmune precipitation assay buffer (50 mM Tris/HCl, pH 8.0, 1% (v/v) Nonidet P-40, 0.5% sodium deoxycholate, 150 mM NaCl, and 0.1% (v/v) SDS) supplemented with a complete protease inhibitor mixture (catalog no. 11 697 498 001, Roche Applied Science). Proteins were separated by 8% SDS polyacrylamide gel electrophoresis, blotted on nitrocellulose membranes (Bio-Rad), and blocked for 1 h in Tris-buffered saline-Tween 20 (TBS-T; 50 mM Tris-HCl, pH 7.5, 150 mM NaCl, 0.1% Tween 20) containing 5% nonfat dry milk. Membranes were then incubated overnight in TBS-T supplemented with 1% nonfat milk and the indicated antibodies; goat anti-human LDLR (1:1000; catalog no. AF2148, R&D Systems), rabbit anti-actin (1:5000; catalog no. A2066, Sigma-Aldrich). Appropriate HRP-conjugated secondary antibodies (1:10,000; GE healthcare) were used for detection using the Western Lightning Ultra chemiluminescence kit (catalog no. NEI112001EA, PerkinElmer Life Sciences) and BioFlex EC Films (catalog no. CLEC810, InterScience). Unsaturated films were numerized using the high resolution CanoScan 9000F scanner and corresponding bands were quantified using the ImageJ software (NIH). Relative quantification of LDLR protein levels were normalized to that of actin and compared to vehicle (DMSO) herein determined as 1. Results are described in Table 2 and illustrated in FIG. 13A to FIG. 13C.

TABLE 2

Result of compound efficacy and cytotoxicity

| Ex. No. | Chemical Name | CC50 (μM) (MTT) | LDLR Fold Change 10 μM | LDLR Fold Change 10 nM |
|---|---|---|---|---|
| 1 | 5-[(4-fluoro-phenylamino)-methyl]-3-hydroxy-4-hydroxymethyl-pyridine-2-carboxylic acid hydroxyamide | 120 | 6.9 | |
| 2 | 5-(4-fluoro-phenoxymethyl)-3-hydroxy-4-hydroxymethyl-pyridine-2-carboxylic acid hydroxyamide | 50 | 6.3 | 2 |
| 3 | 5-(3-chloro-4-fluoro-phenoxymethyl)-3-hydroxy-4-hydroxymethyl-pyridine-2-carboxylic acid hydroxyamide | 11 | 5.6 | |
| 4 | $N^5$-(3-chloro-4-fluorobenzyl)-$N^2$,3-dihydroxy-4-(hydroxymethyl)pyridine-2,5-dicarboxamide | | 2.7 | |
| 5 | 5-{(1-3-chloro-4-fluoro-phenyl)aminomethyl}-2,2-dimethyl-4H-[1,3]dioxino[4,5-c]pyridine-8 carboxylic acid hydroxamide | | 2.4 | |
| 6 | 5-[2-(4-fluoro-phenyl)-ethyl]-3-hydroxy-4-hydroxymethyl-pyridine-2-carboxylic acid hydroxyamide | 39 | 2.3 | 1.5 |
| 7 | 5-(4-methoxy-benzyloxymethyl)-3-hydroxy-4-methyl-pyridine-2-carboxylic acid | | 1.9 2-3 | 1.7 |
| 8 | 5-(4-Methoxy-benzyloxymethyl)-3-hydroxy-4-methyl-pyridine-2-carboxylic acid methyl ester | | 1.7 | 1.7 |
| 9 | Methyl 5-((4-methoxybenzyloxy)methyl)-2,2-dimethyl-4H-[1,3]dioxino[4,5-c]pyridine-8-carboxylate | | 1.4 | |
| 10 | 5-((4-methoxybenzyloxy)methyl)-2,2,8-trimethyl-4H-[1,3]dioxino[4,5-c]pyridine | | 1.2 | 1.7 |
| 11 | 5-(4-methoxybenzyloxymethyl-3-hydroxy-4-methyl-pyridine-2-carboxylic acid hydroxyamide | | 2-3 | |
| 12 | 5-((4-fluorophenylamino)methyl)-3-hydroxy-4-(hydroxymethyl)picolinate | | | |
| 13 | 5-(4-fluoro-benzyloxymethyl)-3-hydroxy-4-hydroxymethyl-pyridine-2-carboxylic acid methoxy-amide | | | |
| 14 | Methyl 5-((4-fluorophenoxy)methyl)-3-hydroxy-4-methylpicolinate | | | |

TABLE 2-continued

Result of compound efficacy and cytotoxicity

| Ex. No. | Chemical Name | CC50 (µM) (MTT) | LDLR Fold Change 10 µM | LDLR Fold Change 10 nM |
|---|---|---|---|---|
| 15 | Methyl 5-((4-fluorophenoxy)methyl)-3-hydroxy-4-(hydroxymethyl) picolinic acid | | | |
| 16 | Methyl 5-((4-fluorophenoxy)methyl)-2,2-dimethyl-4H-[1,3]dioxino[4,5-c]pyridine-8-carboxylate | | | |
| 17 | Methyl 3-(benzyloxy)-5-((4-fluorophenoxy)methyl)-4-methylpicolinate | | | |
| 18 | (3-chloro-4-fluoro-benzyl)-(5-hydroxy-6-hydroxycarbamoyl-4-hydroxymethyl-pyridin-3-ylmethyl)-carbamic acid benzyl ester | | | |
| 19 | 4-hydroxymethyl-3-methoxy-pyridine-2,5-dicarboxylic acid 5-(4-fluoro-benzylamide) 2-hydroxyamide | 6.6 | | |
| 20 | 5-benzenesulfonylmethyl-3-hydroxy-4-hydroxymethyl-pyridine-2-carboxylic acid hydroxyamide | | | |
| 21 | 3-hydroxy-4-hydroxymethyl-pyridine-2,5-dicarboxylic acid 5-dibenzylamide-2-hydroxyamide | | | |
| 22 | N,3-bis(benzyloxy)-5-((3-chloro4-fluorobenzylamino)methyl)-4-(hydroxymethyl) picolinamide | | | |
| 23 | 3-hydroxy-4-hydroxymethyl-pyridine-2,5-dicarboxylic acid 5-(4-fluoro-benzylamide)2-(methoxy-amide) | | | |
| 24 | 5-(4-fluoro-benzyloxymethyl)-3-hydroxy-4-hydroxymethyl-pyridine-2-carboxylic acid hydroxyamide | | | |
| 25 | 2,2-dimethyl-4H-[1,3]dioxino[4,5-c]pyridine-5,8-dicarboxylic acid 5-(3-chloro4-fluoro-benzylamide)-8-(methyl ester) | | 1.9 | |
| 26 | 5-((4-fluorophenoxy)methyl)-2,2-dimethyl-4H-[1,3]dioxino[4,5-c]pi coline | | 1.5 | 1 |
| 27 | 5-((4-fluorophenoxy)methyl)-3-hydroxy-4-(hydroxymethyl)picoline | | 1.2 | 0.6 |

Figure 15:
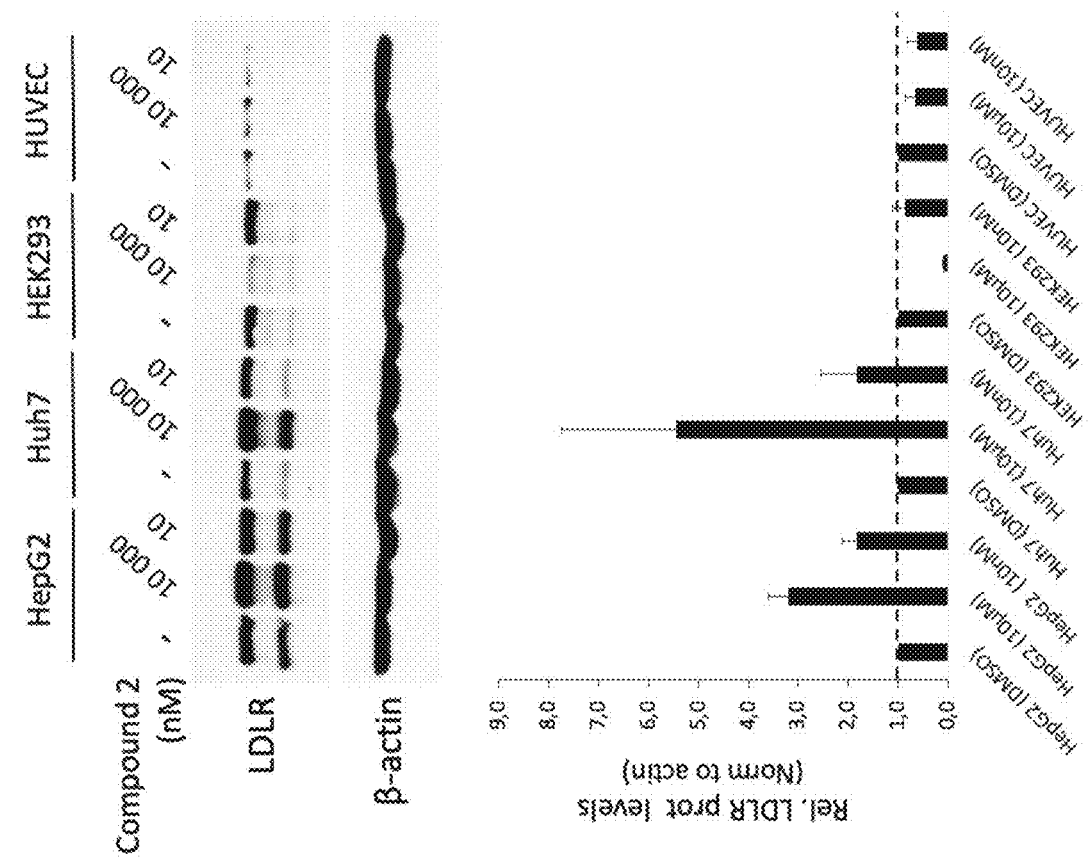
FIG. 15 is a series of graphs showing the effects of Compound 2 on LDLR protein levels by Western blot analyses in various cell types.

FIG. 15 shows the effects of Compound 2 on LDLR protein levels by Western blot analyses in HepG2, Huh7, HEK293, and HUVEC cells.

Example 30. Immunocytochemistry

Figure 14:
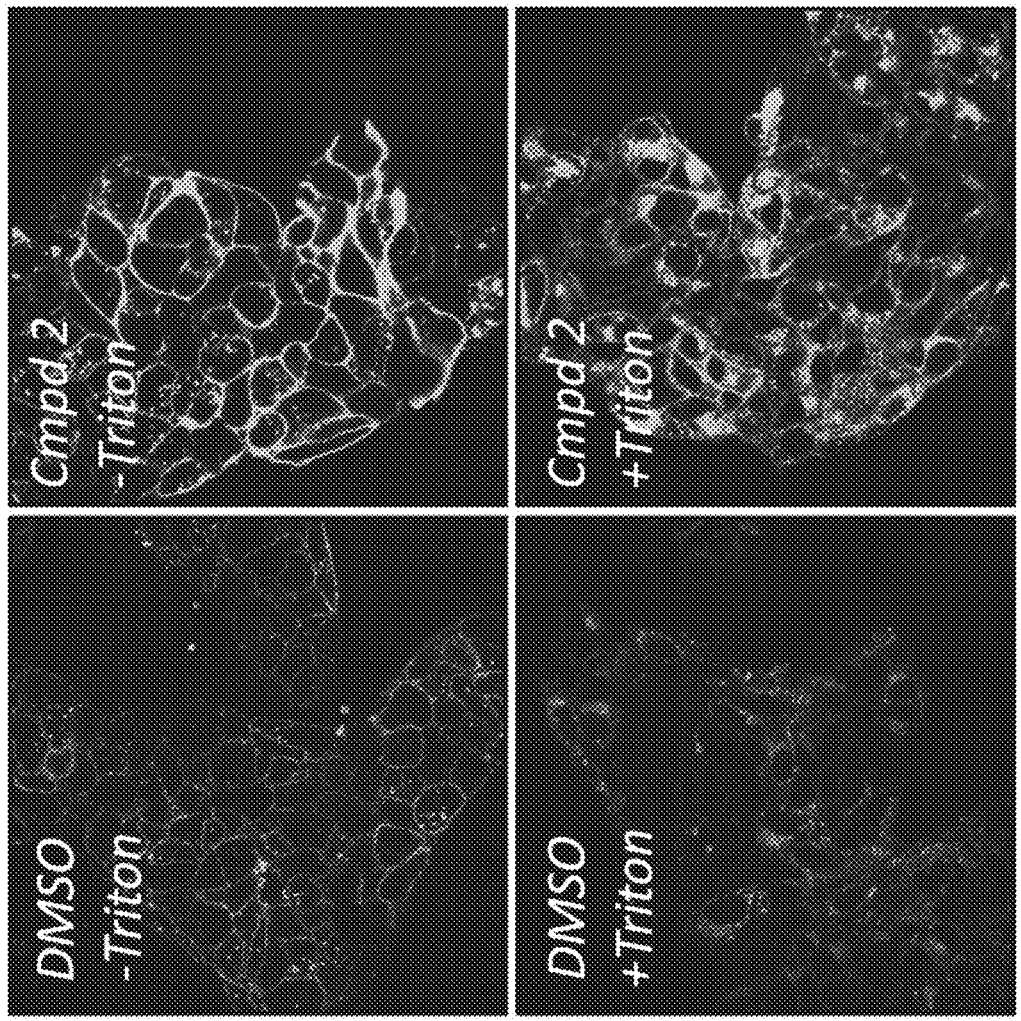
FIG. 14 is a series of images showing the immunofluorescence analysis of LDLR protein using confocal microscopy.

Cells were permeabilized or not with 0.1% Triton X-100/PBS for 10 min, and incubated with 150 mM glycine (to stabilize the aldehydes), incubated for 30 min with 1% BSA (Fraction V, Sigma) containing 0.1% Triton X-100 or not, followed by overnight incubation at 4° C. with goat anti-human LDLR (1:100; R&D Systems, catalog no. AF2148). Afterward, cells were incubated for 60 min with corresponding Alexa Fluor-conjugated secondary antibodies (Molecular Probes) and mounted in 90% glycerol containing 5% 1,4-diazabicyclo[2.2.2]octane (Sigma). Immunofluorescence analyses were performed with an Olympus FluoView FV10i confocal microscope. The visualization of increased expression of the Low density lipoprotein receptor can be seen in FIG. 14.

Example 31. Reverse Transcription and Quantitative Real-Time PCR

Figure 16:
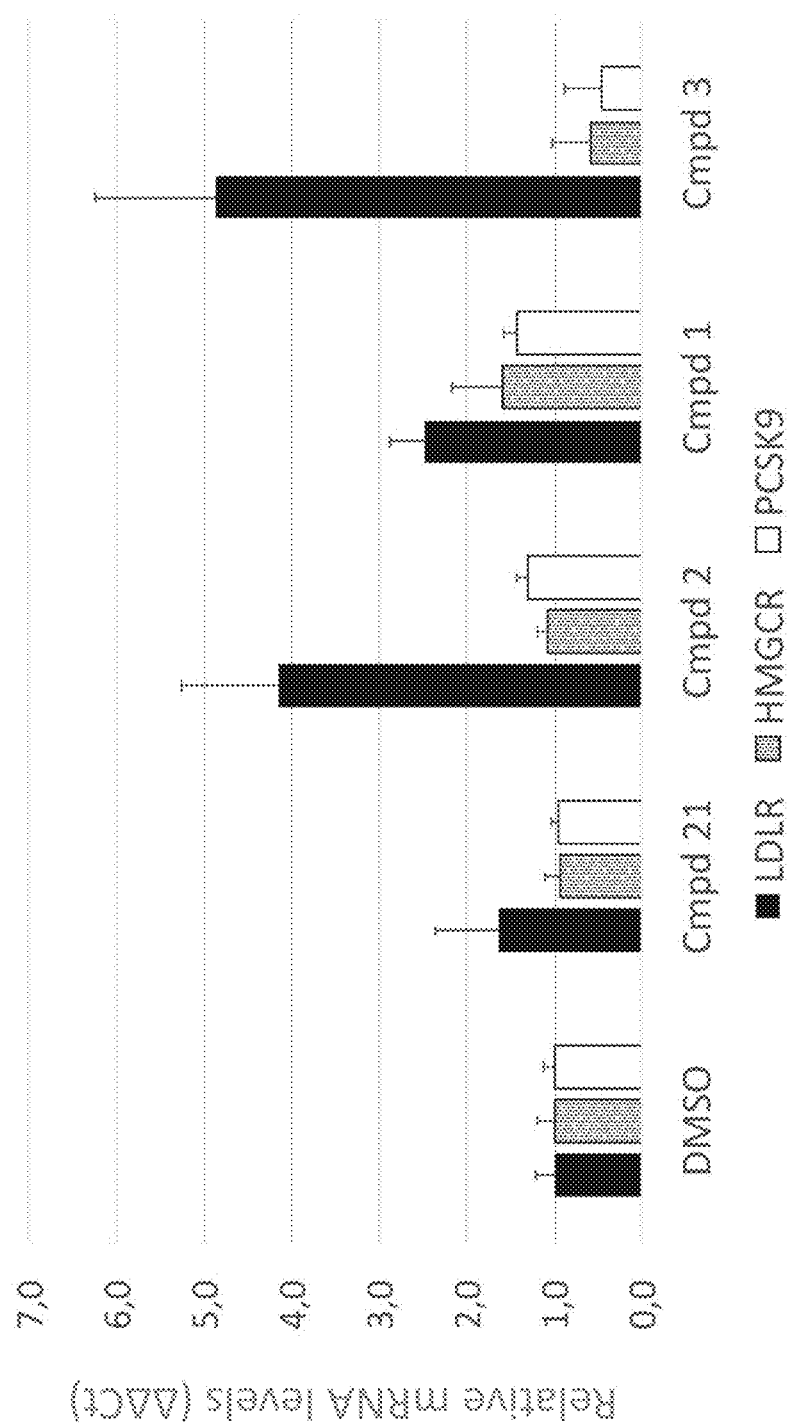
FIG. 16 is a graph showing the relative quantities of LDLR, HMGCR, and PCSK9 mRNA in cells treated with Compounds 1, 2, 3, and 21.

The integrity of total RNA samples, isolated using Ribozol RNA Extraction Reagent (catalog no. N580-100, Amresco), was verified by agarose gel electrophoresis or using an Agilent 2100 BioAnalyzer. cDNA was prepared using iScript cDNA Synthesis Kit according the manufacturer's instructions (catalog no. 1708891, Bio-Rad Laboratories). Quantitative Real-Time PCR was performed in a MX3000p real-time thermal cycler (Agilent) using the iTaq Universal SYBR Green Supermix, (catalog no. 1725121, Bio-Rad Laboratories). For each gene of interest, dissociation curves and agarose gel electrophoresis were performed to ensure unique PCR product. Arbitrary units were determined from PCR duplicates for each sample using the Homo sapiens TATA-box binding protein (hTBP) as a normalizer. Oligonucleotides sequences used were: Homo sapiens low-density lipoprotein receptor (hLDLR; SEQ ID NO 1: 5'-AGGAGACGTGCTTGTCTGTC, SEQ ID NO 2: 5'-CTGAGCCGTTGTCGCAGT), Homo sapiens 3-hydroxy-3-methylglutaryl-Coenzyme A reductase (hHMGCR; SEQ ID NO 3: 5'-GTCACATGATTCACAACAGG, SEQ ID NO 4: 5'-GTCCTTTAGAACCCAATGC), Homo sapiens glyceraldehyde-3-phosphate dehydrogenase (GAPDH; SEQ ID NO 5: 5'-GGTGTGAACCATGAGAAGTATGA, SEQ ID NO 6: 5'-GAGTCCTTCCACGATACCAAAG. Homo sapiens proprotein convertase subtilisin-kexin 9 (hPCSK9) mRNA expression was evaluated on total cDNA using the TaqMan gene expression assay Hs00545399_m1 (catalog no. 4331182, ThermoFisher Scientific) and the TaqMan Fast Advanced Master Mix (catalog no. 4444557, ThermoFisher Scientific). Results of QPCR LDLR mRNA increase is illustrated in FIG. 16.

Example 32. Cell Viability Assay

Cells were seeded into 96-well plates and incubated at confluency overnight with 1, 5, 10, 50, 100 or 500 µM of given compounds in phenol red-free conditioned media (catalog no. 319-051-CL, Wisent). Following incubation, media was replaced and cells incubated for 4 h with 100 µL of phenol red-free DMEM containing 0.5 mg/mL of MTT (3-[4,5-dimethylthiazol-2-yl]-2,5-diphenyltetrazolium bromide; thiazolyl blue; catalog no. M5655, Sigma-Aldrich). Afterwards, media was removed and converted dye solubilized with 100 µL acidic isopropanol (0.06 N) and absorbance measured at a wavelength of 570 nm with background subtraction at 650 nm. Arbitrary units of cell viability of a given example were determined relative to equal volume of DMSO (vehicle) for each concentration used. Results are shown in Table 2.

Example 33. *Gaussia* Luciferase Assay

Figure 17:
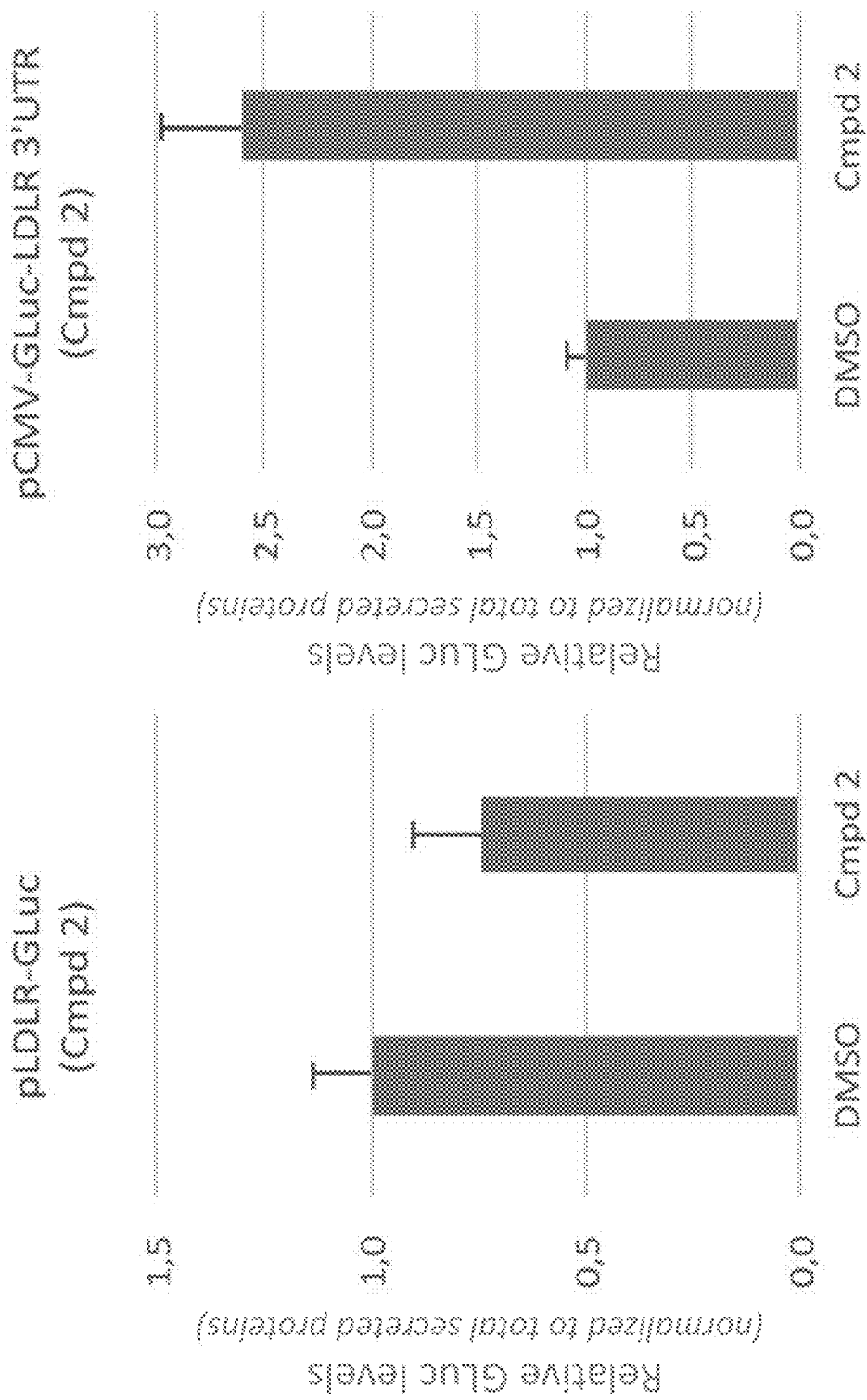
FIG. 17 is a series of graphs showing the effects of Compound 2 on LDLR promoter or LDLR 3'UTR of the Human LDLR gene.

Human LDLR (−1020 bp) proximal promoter and partial 3'UTR (nt 11131317-11132220 chromosome 9) were generated by PCR using genomic DNA from HepG2 cells as template and subcloned into pCMV-GLuc vector (catalog no. $N^{8081}$ S, New England Biolabs) in order to replace the CMV promoter or the 3'UTR region of the vector. Selected clones were verified by DNA sequencing. Oligonucleotides used were: hLDLR promoter (SEQ ID NO 7: 5'-TGTACTAGTCTTATTCCTGGGGGAACCGC, SEQ ID NO 8: 5'-GCAAAGCTTGCTCG-CAGCCTCTG-CCAGGCAGTG and hLDLR 3'UTR (SEQ ID NO 9: 5'-TACGCGGCCGCACATCTGCCTGGAGTCCCGTC, SEQ ID NO 10: 5'-ACTTCTAGACCCATCCC-AACACACACGACAG). For transient experiments, HepG2 cells were seeded in 24-well plates at a density of 1.5 $10^5$/well. 24 h later, cells were transfected in duplicate with the corresponding pGLuc construct using Lipofectamine 3000 (catalog no. L3000008, Thermo Fisher Scientific). After overnight incubation, cells were washed twice with DMEM and incubated in 0.5 mL of DMEM without or with given examples at various concentration for 24 h. 20 μL of conditioned media was loaded into black 96-well plates, and relative activity of secreted *Gaussia* luciferase was assessed by luminescence measurements using the BioLux kit (catalog no. E3300L, New England Biolabs) and the BioTek Synergy 2 microplate reader. High quality of HepG2 cells stability expressing pGLuc-LDLR-3'UTR were also generated following selection with 0.75 mg/mL G418 Sulfate antibiotic (catalog. 400-130-IG, Wisent). Results are displayed in FIG. 17.

Example 34. Measurements of mRNA Decay

Figure 18:
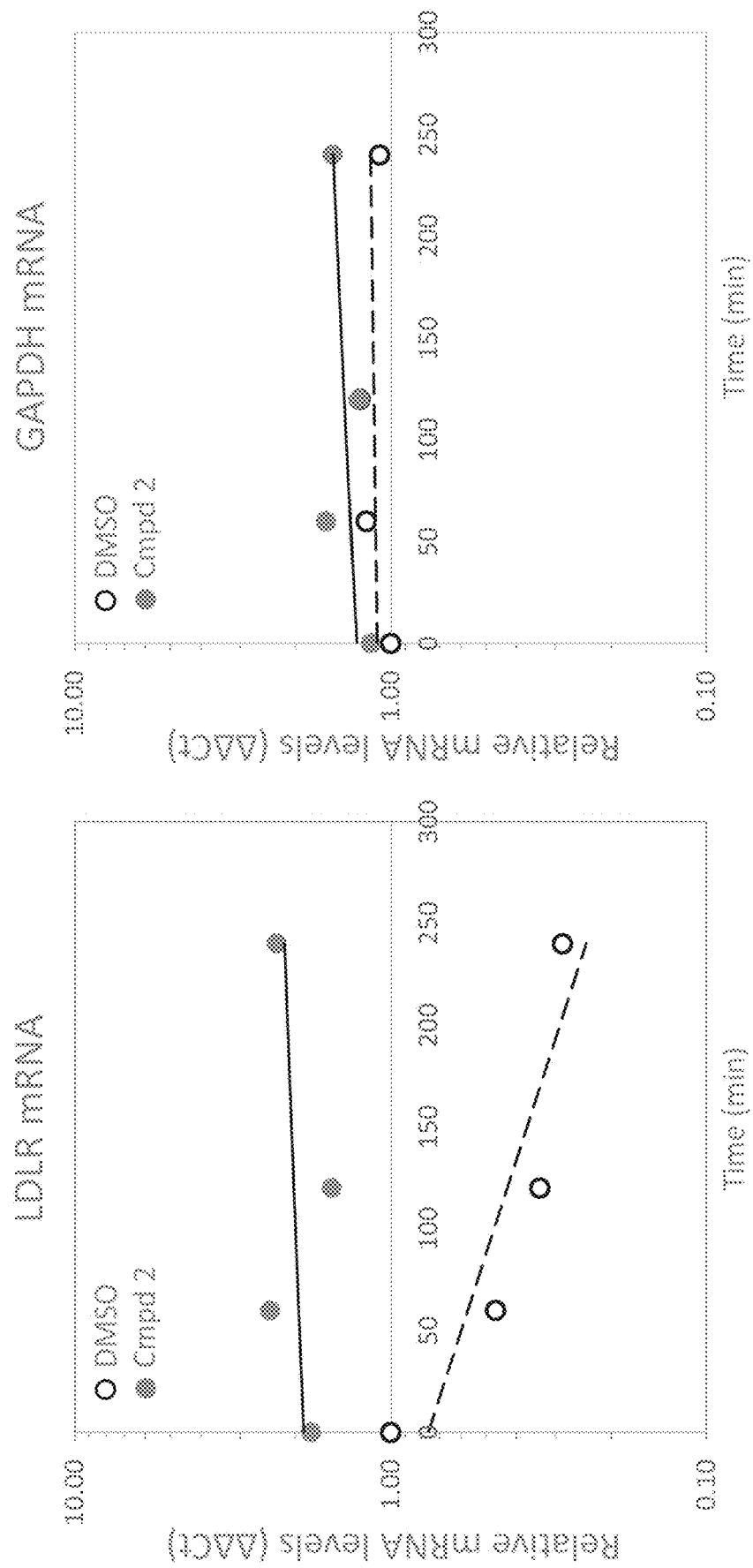
FIG. 18 is a series of graphs showing the effects of Compound 2 on mRNA decay or the Human LDLR and Human GAPDH genes.

HepG2 cells were incubated with DMSO or 10 μM of Compound 2 for 24 h. Following incubation, cells were washed twice with DMEM and incubated with 5 μg/ml actinomycin D for 0, 60, 120 and 240 min. LDLR and GAPDH relative mRNA levels were analyzed by Quantitative Real-Time PCR as described in Example 31. Results of QPCR LDLR mRNA stabilization is illustrated in FIG. 18.

Example 35. Microsomal Stability Assay

Pooled human liver microsomes (HLM; Cat #X008067 lot IHG) and pooled male Sprague Dawley rat liver microsomes (RLM; Cat #M00001 Lot NNK) were purchased from BioreclamationIVT, Baltimore, Maryland. NADPH (Cat #$N^{1630, 95}$% HPLC) and DMSO (GC grade) were purchased from Sigma-Aldrich, Canada. Potassium phosphate buffer (100 mM) with magnesium chloride pH 7.4 was prepared freshly. Potassium phosphate buffer (100 mM, pH 7.4, +2 mM MgCl2) containing human or rat liver microsomes (0.50 mg/ml) was pre-incubated separately with Compound 2 (1 μM) or positive control (loperamide, 1 μM) in a water bath with the temperature set at 37° C. for 5 min (N=2). Reactions were initiated by adding NADPH (final concentration 1 mM) in all the wells. Reactions without NADPH were also incubated (final point only) to rule out non-NADPH metabolism or chemical instability in the incubation buffer. Reactions were terminated at each time point (0, 5, 10, 20, 30, 45 and 60 min) by transferring 50 μL in a new 96 well plate and adding 100 μl of acetonitrile containing an internal standard (labetalol at 2 μM). The plates were centrifuged at 4000 rpm for 5 min, and an aliquot of supernatant was diluted with one volume of water+0.1% formic acid before analysis by LC-MS/MS. Reference samples were also prepared at concentrations between 0.002 and 2 μM in buffer containing microsomes, by adding the diluted solutions of the compound to the buffer containing microsomes quenched with 2 volume of acetonitrile containing the internal standard (whereas the incubation T0 is obtained by quenching the microsomes containing the compound, then adding NADPH). Samples were monitored for parent compound disappearance in Multi Reaction Monitoring (MRM) mode using LC-MS/MS. The peak area ratios of analyte versus internal standard compared to the calibration curve were used to calculate concentration at each time point. The elimination constant (ke, min-1) was obtained from the log-linear regression of the concentration (y) versus time (t). The half-life was calculated as T1/2 (min)=0.693/ke. The microsomal intrinsic clearance (Clint, μL/min/mg of protein) was calculated by the following equation:

$$\text{Clint} \,(\mu L/\text{min/mg of protein}) = \frac{V \times 0.693}{T1/2} = V \times Ke$$

$$\text{Where } V(\mu L/mg) = \frac{\text{Volume of incubation } (\Box L)}{\text{Protein in the incubation (mg)}}$$

Results are shown in Table 3.

TABLE 3

| Microsomal stability assay | −k | half life (min) | Clint uL/min/mg pro |
|---|---|---|---|
| Cmpd 2 (HLM) | 7,03E-04 ± 1.9E-05 | 986 ± 27 | 1.17 ± 0.03 |
| Cmpd 2 (RLM) | 1,26E-03 ± 1.9E-04 | 404 ± 28 | 6.19 ± 0.42 |
| Loperamide (HLM) | 3.25E02 | 21 ± 1 | 54.07 ± 1.73 |
| Loperamide (RLM) | 7.53E-02 | 9 ± 0 | 270.99 ± 2.98 |

Example 36. Animal Studies

Figure 20:
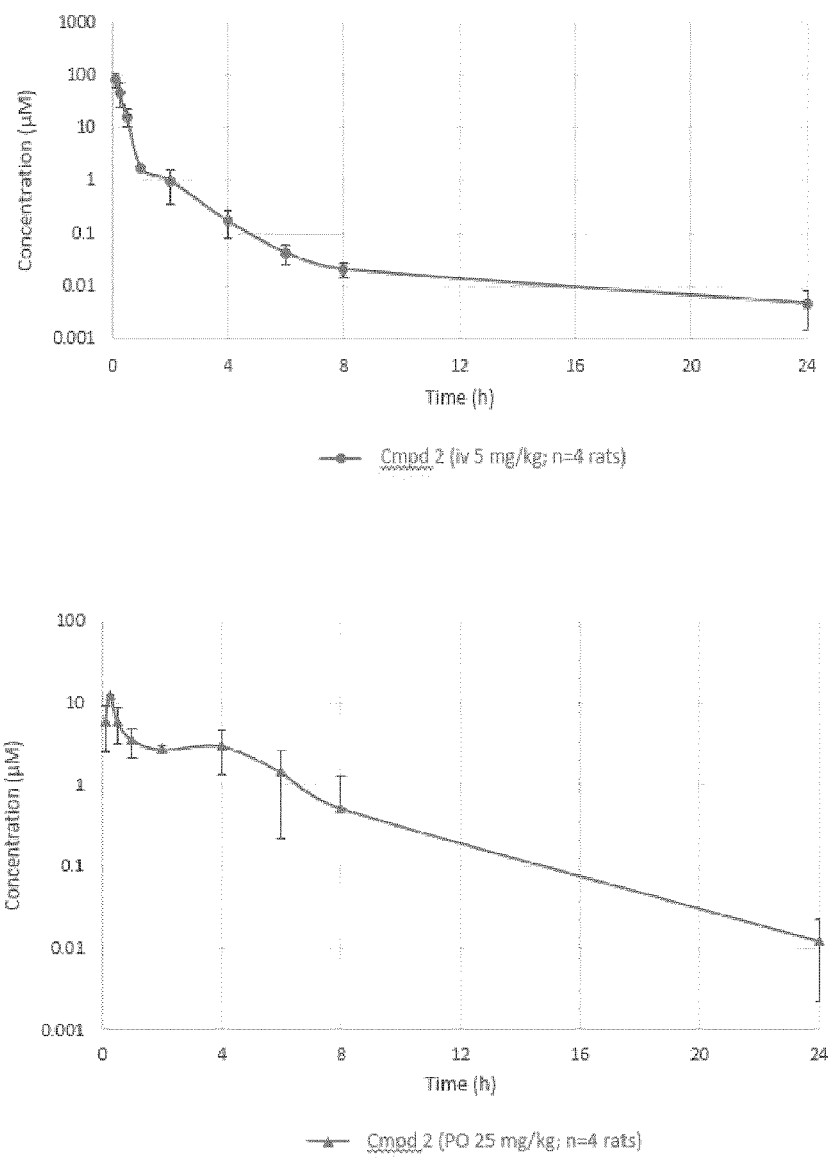
FIG. 20 is a series of graphs showing Pharmacokinetics of Compound 2 in adult Sprague-Dawley rats.

All animal studies were approved by the Montreal Heart Institute (MHI) Animal Care and Ethical committee. Pharmacokinetic experiments were performed in collaboration at the Montreal Heart Institute in collaboration with the Platform of Biopharmacy at Universite de Montreal. Briefly, Compound 2 (formulation PG:$H_2O$; 50:50 stock solution 2.5 mg/ml) was administered intravenously (iv) at 5 mg/kg (n=4) or by oral gavage (PO) at 25 mg/kg (n=4) in adult Sprague-Dawley male rats (~200 g). Blood samples were collected at 5, 15, 30, 60, 120, 240, 360, 480, 1440 min for which 125 μL of precipitation solution (80% acetonitrile and 20% methanol containing IS Loperamide at 0.1 μM) were added. Samples were mixed and centrifuged at 15000 rpm for 5 min. 50 μL of supernatant were transferred to an HPLC plate, and 100 μL of water+0.1% formic acid were added. A 16-point calibration curve with example 2 was prepared in blank rat blood, ranging from 0.002 to 15 μM. Samples were analyzed in MRM mode using LC-MS/MS. The calibration curve was plotted using the ratio of the analyte peak area and the IS peak area, using a quadratic regression. Pharmacokinetic (PK) parameters were calculated using Kinetica Software for PK/PD Data Analysis, Simulation and Reporting (Thermo Fisher), based on the blood concentrations of each animal. Results are described in Table 4 and illustrated in FIG. 20.

TABLE 4

Pharmacokinetic parameters

Compound 2 (iv 5 mg/kg)

| Parameter | Unit | Average (n = 4) | StDev (n = 4) |
|---|---|---|---|
| AUClast | µM*h | 31.84 | 12.78 |
| AUCtot | µM*h | 31.90 | 12.83 |
| MRT | h | 0.55 | 0.08 |
| Lz | 1/h | 0.12 | 0.06 |
| thalf | h | 6.60 | 2.67 |
| Tmax | h | 0.08 | 0.00 |
| Cmax | µMolar | 81.12 | 24.53 |
| Clearance | mL/min | 2.20 | 0.88 |
| Vss | L | 0.08 | 0.04 |

Compound 2 (PO 25 mg/kg)

| Parameter | Unit | Average (n = 4) | StDev (n = 4) |
|---|---|---|---|
| AUClast | µM*h | 24.23 | 9.26 |
| AUCtot | µM*h | 24.28 | 9.29 |
| MRT | h | 3.44 | 1.42 |
| Lz | 1/h | 0.24 | 0.02 |
| thalf | h | 2.97 | 0.28 |
| Tmax | h | 0.33 | 0.20 |
| Cmax | µMolar | 7.09 | 3.46 |
| Clearance | mL/min | 13.44 | 6.26 |
| Vss | L | 2.43 | 0.55 |
| % F | % | 15% | 6% |

For in vivo proof-of-concept animal studies, wild-type C57BL/6 male mice (~25 g; obtained from Charles River Laboratories) or Golden Syrian (~120 g obtained from Envigo++) were housed in the 12 hour light/12 hour dark cycle, temperature and humidity controlled MHI animal facility. Following 5 days of acclimatization, animals were fed a chow or Western diet containing 48.5% w/w carbohydrate, 21.2% w/w fat, 17.3% w/w protein and 0.2% w/w cholesterol (catalog no. TD.88137, Envigo) for 14 days. Example 1, 2, and 6 were mixed in either ethanol/propylene glycol/water; 1:7:8 or 1:2:1 (v/v), or in phosphate-buffered saline (PBS; catalog no. 311-010-CL, Wisent) containing 0.01% Tween 20 and administered by oral gavage at 5, 25 or 40 mg/kg/day for 3 or 10 days in mice maintained on chow or Western diet. Equivalent volume of vehicle containing corresponding formulations were orally administered to mice daily and designated as placebo (vehicle). Plasma lipoprotein cholesterol profiles were obtained from 100 µL of pooled plasma injected on a Superose 6 10/300 GL (catalog no. 17-5172-01, GE Life Sciences) and eluted with PBS at a flow rate of 0.1 mL per min at 4° C. mounted on a ÄKTA explorer system (GE Healthcare). Total cholesterol (catalog no. 439-17501, Wako) was quantified in total plasma and in each 0.3 mL collected fractions or in-line (Lipidomics Core of The Group on Molecular and Cell Biology of Lipids, University of Alberta) according to the manufacturer's instructions. Relative quantitation of AUC of total cholesterol corresponding to non-HDL lipoprotein positive fractions obtained from FPLC profiles are included in Table 3. Serum aspartate aminotransferase (AST) and alanine transaminase (ALT) were measured by the Montreal Heart Institute biochemical clinical chemistry platform according to manufacturer's recommendations. Results are described in Table 5.

TABLE 5

Efficacy and Safety of Compound 2 in hypercholesterolemic animal models

| Model | n | Diet | Dosage (mpk/d) | Duration (days) | LDL-C (%) (FPLC TC) (pooled plasma) | ALT (3 × ULN) | AST (3 × ULN) |
|---|---|---|---|---|---|---|---|
| C57BL/6 | 3 | Chow | 25 | 3 | −31 | | |
| C57BL/6 | 4 | HFD | 40 | 10 | −35 ± 2 | 0/4 | 0/4 |
| C57BL/6 | 4 | HFD | 25 | 10 | −28 ± 8 | | |
| C57BL/6 | 4 | HFD | 5 | 10 | −3 ± 8 | | |
| Golden Syrian | 3 | HFD | 40 | 10 | −47 (n = 1) | 0/3 | 0/3 |
| Golden Syrian | 3 | Chow | 40 | 10 | −12 | | |
| Golden Syrian | 3 | HFD | 40 | 10 | −26 ± 12 | | |
| Golden Syrian | 3 | HFD | 20 | 10 | −40 ± 7 | | |
| Golden Syrian | 3 | HFD | 10 | 10 | −15 ± 16 | | |
| Golden Syrian | 3 | HFD | 5 | 10 | −21 ± 10 | | |

OTHER EMBODIMENTS

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A method of lowering low-density lipoprotein (LDL)-cholesterol level in the bloodstream of a subject, the method comprising administering to the subject a LDL-lowering amount of 5-(3-chloro-4-fluoro-phenoxymethyl)-3-hydroxy-4-hydroxymethyl-pyridine-2-carboxylic acid hydroxyamide
or
a pharmaceutically acceptable salt thereof.

2. The method of claim 1, wherein the subject has been diagnosed with atherosclerosis, hypercholesterolemia, hypertriglyceridemia, diabetic complications, dyslipidemia, hyperlipidemia, hypoalphalipoproteinemia, metabolic syndrome, stroke, vascular dementia, chronic kidney disease, coronary heart disease, coronary artery disease, retinopathy, inflammation, thrombosis, peripheral vascular disease or congestive heart failure.

3. The method of claim 2, wherein the hypercholesterolemia is heterozygous familial hypercholesterolemia.

4. The method of claim 2, wherein the hypercholesterolemia is homozygous familial hypercholesterolemia.

5. The method of claim 1, wherein a pharmaceutical composition comprising the compound or the salt is administered to the subject.

6. A method of treating atherosclerosis, hypercholesterolemia, dyslipidemia, or hyperlipidemia, the method comprising administering to a subject in need thereof, a therapeutically effective amount of 5-(3-chloro-4-fluoro-phenoxymethyl)-3-hydroxy-4-hydroxymethyl-pyridine-2-carboxylic acid hydroxyamide; or
a pharmaceutically acceptable salt thereof.

7. The method of claim 6, wherein a pharmaceutical composition comprising the compound or the salt is administered to the subject.

8. A method of inducing low density lipoprotein receptor (LDLR) expression in a cell, the method comprising contacting the cell with an effective amount of 5-(3-chloro-4-fluoro-phenoxymethyl)-3-hydroxy-4-hydroxymethyl-pyridine-2-carboxylic acid hydroxyamide; or a pharmaceutically acceptable salt thereof.

9. The method of claim 8, wherein a pharmaceutical composition comprising the compound or the salt is administered to the subject.

10. A method of modulating LDLR mRNA activity in a cell, the method comprising contacting the cell with an effective amount of 5-(3-chloro-4-fluoro-phenoxymethyl)-3-hydroxy-4-hydroxymethyl-pyridine-2-carboxylic acid hydroxyamide; or a pharmaceutically acceptable salt thereof.

11. The method of claim 10, wherein a pharmaceutical composition comprising the compound or the salt is administered to the subject.

12. The method of claim 1, further comprising administering a second cholesterol lowering agent to the subject.

13. The method of claim 12, wherein the second cholesterol lowering agent is a lipase inhibitor, a 3-hydroxy-3-methyl-glutaryl-coenzyme A (HMG CoA) reductase inhibitor, a HMG CoA synthase inhibitor, a cholesterylester transfer protein (CETP) inhibitor, a bile acid absorption inhibitor, a cholesterol absorption inhibitor, a cholesterol synthesis inhibitor, a squalene synthetase inhibitor, a squalene epoxidase or cyclase inhibitor or a combination of both, a microsomal triglyceride transfer protein (MTP)/Apolipoprotein B (ApoB) secretion inhibitor, a fibrate, niacin alone or in combination with lovastatin, an ion-exchange resin, an antioxidant, an acyl-coenzyme A:cholestero acyl-transferase (ACAT) inhibitor and a bile acid sequestrant, an HMG-CoA reductase gene expression inhibitor, an HMG-CoA synthase gene expression inhibitor, or a proprotein convertase subtilisin kexin type 9 (PCSK9) inhibitor.

14. The method of claim 13, wherein the cholesterol synthesis inhibitor is a statin.

15. The method of claim 14, wherein the statin is atorvastatin.

16. The method of claim 1, wherein the subject, prior to administration of the compound of Formula 1, was treated with a lipase inhibitor, a 3-hydroxy-3-methyl-glutaryl-coenzyme A (HMG CoA) reductase inhibitor, a HMG CoA synthase inhibitor, a cholesterylester transfer protein (CETP) inhibitor, a bile acid absorption inhibitor, a cholesterol absorption inhibitor, a cholesterol synthesis inhibitor, a squalene synthetase inhibitor, a squalene epoxidase or cyclase inhibitor or a combination of both, a microsomal triglyceride transfer protein (MTP)/Apolipoprotein B (ApoB) secretion inhibitor, a fibrate, niacin alone or in combination with lovastatin, an ion-exchange resin, an antioxidant, an acyl—coenzyme A:cholesterol acyltransferase (ACAT) inhibitor and a bile acid sequestrant, an HMG-CoA reductase gene expression inhibitor, an HMG-CoA synthase gene expression inhibitor, or a proprotein convertase subtilisin kexin type 9 (PCSK9) inhibitor.

17. The method of claim 16, wherein the prior administration did not effectively lower the cholesterol level in the bloodstream of the subject.

* * * * *

UNITED STATES PATENT AND TRADEMARK OFFICE
CERTIFICATE OF CORRECTION

PATENT NO. : 11,931,348 B2
APPLICATION NO. : 17/750698
DATED : March 19, 2024
INVENTOR(S) : Steve Poirier et al.

Page 1 of 1

It is certified that error appears in the above-identified patent and that said Letters Patent is hereby corrected as shown below:

In the Claims

Column 54, Claim 13, Line 66, replace "cholestero" with --cholesterol--.

Signed and Sealed this
Fifth Day of November, 2024

Katherine Kelly Vidal
*Director of the United States Patent and Trademark Office*

SEQUENCE LISTING

<160> NUMBER OF SEQ ID NOS: 10

<210> SEQ ID NO 1
<211> LENGTH: 20

```
<212> TYPE: DNA
<213> ORGANISM: Artificial Sequence
<220> FEATURE:
<223> OTHER INFORMATION: Synthetic Construct

<400> SEQUENCE: 1
aggagacgtg cttgtctgtc                                              20

<210> SEQ ID NO 2
<211> LENGTH: 18
<212> TYPE: DNA
<213> ORGANISM: Artificial Sequence
<220> FEATURE:
<223> OTHER INFORMATION: Synthetic Construct

<400> SEQUENCE: 2
ctgagccgtt gtcgcagt                                                18

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct

<400> SEQUENCE: 3
gtcacatgat tcacaacagg                                              20

<210> SEQ ID NO 4
<211> LENGTH: 19
<212> TYPE: DNA
<213> ORGANISM: Artificial Sequence
<220> FEATURE:
<223> OTHER INFORMATION: Synthetic Construct

<400> SEQUENCE: 4
gtcctttaga acccaatgc                                               19

<210> SEQ ID NO 5
<211> LENGTH: 23
<212> TYPE: DNA
<213> ORGANISM: Artificial Sequence
<220> FEATURE:
<223> OTHER INFORMATION: Synthetic Construct

<400> SEQUENCE: 5
ggtgtgaacc atgagaagta tga                                          23

<210> SEQ ID NO 6
<211> LENGTH: 22
<212> TYPE: DNA
<213> ORGANISM: Artificial Sequence
<220> FEATURE:
<223> OTHER INFORMATION: Synthetic Construct

<400> SEQUENCE: 6
gagtccttcc acgataccaa ag                                           22

<210> SEQ ID NO 7
<211> LENGTH: 29
<212> TYPE: DNA
<213> ORGANISM: Artificial Sequence
<220> FEATURE:
<223> OTHER INFORMATION: Synthetic Construct

<400> SEQUENCE: 7
```

```
tgtactagtc ttattcctgg gggaaccgc                                            29

<210> SEQ ID NO 8
<211> LENGTH: 33
<212> TYPE: DNA
<213> ORGANISM: Artificial Sequence
<220> FEATURE:
<223> OTHER INFORMATION: Synthetic Construct

<400> SEQUENCE: 8
gcaaagcttg ctcgcagcct ctgccaggca gtg                                       33

<210> SEQ ID NO 9
<211> LENGTH: 32
<212> TYPE: DNA
<213> ORGANISM: Artificial Sequence
<220> FEATURE:
<223> OTHER INFORMATION: Synthetic Construct

<400> SEQUENCE: 9
tacgcggccg cacatctgcc tggagtcccg tc                                        32

<210> SEQ ID NO 10
<211> LENGTH: 31
<212> TYPE: DNA
<213> ORGANISM: Artificial Sequence
<220> FEATURE:
<223> OTHER INFORMATION: Synthetic Construct

<400> SEQUENCE: 10
acttctagac ccatcccaac acacacgaca g                                         31
```